(12) United States Patent
Connors et al.

(10) Patent No.: US 11,197,981 B2
(45) Date of Patent: *Dec. 14, 2021

(54) PRESSURE ATTENUATION DEVICE

(71) Applicant: Solace Therapeutics, Inc., Framingham, MA (US)

(72) Inventors: Kevin G. Connors, Wellesley, MA (US); Albert Chun-Chi Chin, Newton, MA (US); Roy H. Sullivan, III, Uxbridge, MA (US); Matthew J. Whitney, Upton, MA (US); William H. Gruber, Southborough, MA (US)

(73) Assignee: Solace Therapeutics, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/857,057

(22) Filed: Apr. 23, 2020

(65) Prior Publication Data

US 2020/0324091 A1 Oct. 15, 2020

Related U.S. Application Data

(63) Continuation of application No. 16/784,045, filed on Feb. 6, 2020.

(60) Provisional application No. 62/802,622, filed on Feb. 7, 2019.

(51) Int. Cl.
*A61M 25/10* (2013.01)

(52) U.S. Cl.
CPC ..... *A61M 25/10* (2013.01); *A61M 2205/0216* (2013.01); *A61M 2205/3331* (2013.01); *A61M 2210/1085* (2013.01)

(58) Field of Classification Search
CPC .......... A61M 25/10; A61M 2205/0216; A61M 2210/1085; A61F 2/0013; A61F 2/0027; A61F 2/004

See application file for complete search history.

(56) References Cited

U.S. PATENT DOCUMENTS

| 2,638,093 A | 5/1953 | Kulick |
| 2,668,538 A | 2/1954 | Baker |
| 2,849,001 A | 8/1958 | Oddo |

(Continued)

FOREIGN PATENT DOCUMENTS

| DE | 19819432 | 11/1999 |
| EP | 0 101 012 | 2/1984 |

(Continued)

OTHER PUBLICATIONS

U.S. Appl. No. 16/443,654, filed Jun. 17, 2019, Cahill et al.

(Continued)

*Primary Examiner* — Thaddeus B Cox
(74) *Attorney, Agent, or Firm* — Knobbe, Martens, Olson & Bear, LLP

(57) ABSTRACT

An pressure attenuation device for use in a body can include a balloon comprising an outer wall and defining an interior chamber therein. The balloon can be configured to elastically deform up to at least to an internal pressure of 90 cm H2O. A high vapor pressure media having a vapor pressure of between 155 cm-185 cm H2O at 37 degrees Celsius can be positioned within the interior chamber. The balloon can have a minimum wall thickness of between 0.001 inches-0.00175 inches.

22 Claims, 34 Drawing Sheets

(56) References Cited

U.S. PATENT DOCUMENTS

| | | | |
|---|---|---|---|
| 3,411,534 A | 11/1968 | Rose | |
| 3,477,454 A | 11/1969 | Fields | |
| 3,768,102 A | 10/1973 | Kwan-Gett et al. | |
| 3,797,478 A | 3/1974 | Walsh et al. | |
| 3,812,841 A | 5/1974 | Isaacson | |
| 3,834,394 A | 9/1974 | Hunter et al. | |
| 3,841,304 A | 10/1974 | Jones | |
| 3,863,622 A | 2/1975 | Buuck | |
| 3,939,821 A | 2/1976 | Roth | |
| 3,964,484 A | 6/1976 | Reyolds et al. | |
| 4,043,323 A | 8/1977 | Komiya | |
| 4,044,401 A | 8/1977 | Guiset | |
| 4,197,835 A | 4/1980 | Reinicke | |
| 4,204,282 A | 5/1980 | Bolt | |
| 4,213,461 A | 7/1980 | Pevsner | |
| 4,222,377 A | 9/1980 | Burton | |
| 4,246,893 A | 1/1981 | Berson | |
| 4,300,557 A | 11/1981 | Refojo et al. | |
| 4,311,146 A | 1/1982 | Wonder | |
| 4,341,218 A | 7/1982 | Ü | |
| 4,346,712 A | 8/1982 | Handa et al. | |
| 4,364,392 A | 12/1982 | Strother et al. | |
| 4,408,597 A | 10/1983 | Tenney, Jr. | |
| 4,416,267 A | 11/1983 | Garren et al. | |
| 4,416,663 A | 11/1983 | Hall | |
| 4,441,495 A | 4/1984 | Hicswa | |
| 4,470,407 A | 9/1984 | Hussein | |
| 4,517,979 A | 5/1985 | Pecenka | |
| 4,545,367 A | 10/1985 | Tucci | |
| 4,551,862 A | 11/1985 | Haber | |
| 4,554,533 A | 11/1985 | Leighton | |
| 4,567,880 A | 2/1986 | Goodman | |
| 4,587,955 A | 5/1986 | Gengler | |
| 4,598,699 A | 7/1986 | Garren et al. | |
| 4,607,618 A | 8/1986 | Angelchik | |
| 4,669,478 A | 6/1987 | Robertson | |
| 4,679,546 A | 7/1987 | Van Wallwijk et al. | |
| 4,694,827 A | 9/1987 | Weiner et al. | |
| 4,705,518 A | 11/1987 | Baker et al. | |
| 4,716,901 A | 1/1988 | Jackson et al. | |
| 4,723,547 A | 2/1988 | Kullas et al. | |
| 4,731,083 A | 3/1988 | Fischell | |
| 4,739,758 A | 4/1988 | Lai et al. | |
| 4,773,393 A | 9/1988 | Haber et al. | |
| 4,773,908 A | 9/1988 | Hilton | |
| 4,784,660 A | 11/1988 | Fischell | |
| 4,802,479 A | 2/1989 | Haber et al. | |
| 4,819,637 A | 4/1989 | Dormandy, Jr. et al. | |
| 4,832,680 A | 5/1989 | Haber | |
| 4,846,784 A | 7/1989 | Haber | |
| 4,850,963 A | 7/1989 | Sparks | |
| 4,878,889 A | 11/1989 | Polyak | |
| 4,899,747 A | 2/1990 | Garren et al. | |
| 4,908,011 A | 3/1990 | Jacobsen et al. | |
| 4,923,461 A | 5/1990 | Caspari et al. | |
| 4,925,446 A | 5/1990 | Garay et al. | |
| 4,929,214 A | 5/1990 | Liebermann | |
| 4,930,535 A | 6/1990 | Rinehold | |
| 4,938,766 A | 7/1990 | Jarvik | |
| 4,945,895 A | 8/1990 | Takai et al. | |
| 4,968,294 A | 11/1990 | Salama | |
| 4,974,811 A | 12/1990 | Ishida | |
| 4,994,019 A | 2/1991 | Fernandez et al. | |
| 5,002,556 A | 3/1991 | Ishida et al. | |
| 5,012,822 A | 5/1991 | Schwarz | |
| 5,013,303 A * | 5/1991 | Tamari | A61M 5/1483 128/DIG. 12 |
| 5,019,032 A | 5/1991 | Robertson | |
| 5,041,092 A | 8/1991 | Barwick | |
| 5,064,434 A | 11/1991 | Haber | |
| 5,082,025 A | 1/1992 | DeVries | |
| 5,084,061 A | 1/1992 | Gau et al. | |
| 5,088,980 A | 2/1992 | Leighton | |
| 5,097,848 A | 3/1992 | Schwartz | |
| 5,123,428 A | 6/1992 | Schwartz | |
| 5,140,999 A | 8/1992 | Ardito | |
| 5,144,708 A | 9/1992 | Pekar | |
| 5,179,963 A | 1/1993 | Berger | |
| 5,181,921 A | 1/1993 | Makita et al. | |
| 5,197,984 A | 3/1993 | Kedem | |
| 5,222,970 A | 6/1993 | Reeves | |
| 5,248,275 A | 9/1993 | McGrath et al. | |
| 5,295,956 A | 3/1994 | Bales et al. | |
| 5,295,960 A | 3/1994 | Aliahmad et al. | |
| 5,304,123 A | 4/1994 | Atala et al. | |
| 5,308,327 A | 5/1994 | Heaven et al. | |
| 5,322,501 A | 6/1994 | Mahmud-Durrani | |
| 5,328,469 A | 7/1994 | Coletti | |
| 5,347,992 A | 9/1994 | Pearlman et al. | |
| 5,356,430 A | 10/1994 | Nadol, Jr. | |
| 5,389,217 A | 2/1995 | Singer | |
| 5,403,123 A | 4/1995 | Walters | |
| 5,411,475 A | 5/1995 | Atala et al. | |
| 5,417,667 A | 5/1995 | Tennican et al. | |
| 5,423,212 A | 6/1995 | Manaka | |
| 5,433,216 A | 7/1995 | Sugrue et al. | |
| 5,437,603 A | 8/1995 | Cerny et al. | |
| 5,437,604 A | 8/1995 | Kulisz et al. | |
| 5,476,434 A | 12/1995 | Kalb et al. | |
| 5,479,945 A | 1/1996 | Simon | |
| 5,490,838 A * | 2/1996 | Miller | A61M 25/10 604/103.11 |
| 5,501,669 A | 3/1996 | Conway et al. | |
| 5,509,889 A | 4/1996 | Kalb et al. | |
| 5,513,659 A | 5/1996 | Buuck et al. | |
| 5,564,143 A | 10/1996 | Pekar et al. | |
| 5,588,438 A | 12/1996 | McKnown et al. | |
| 5,588,556 A | 12/1996 | Sancoff et al. | |
| 5,603,685 A | 2/1997 | Tutrone, Jr. | |
| 5,617,876 A | 4/1997 | van Duyl | |
| 5,618,257 A | 4/1997 | Kulisz et al. | |
| 5,634,878 A | 6/1997 | Grundei | |
| 5,637,074 A | 6/1997 | Andino et al. | |
| 5,651,765 A | 7/1997 | Schulman et al. | |
| 5,667,520 A | 9/1997 | Bonutti | |
| 5,674,230 A | 10/1997 | Tovey et al. | |
| 5,695,741 A | 12/1997 | Schutt et al. | |
| 5,701,916 A | 12/1997 | Kulisz | |
| 5,711,314 A | 1/1998 | Ardito | |
| 5,720,938 A | 2/1998 | Schutt et al. | |
| 5,728,112 A | 3/1998 | Yoon | |
| 5,755,239 A | 5/1998 | Baltierra | |
| 5,770,627 A | 6/1998 | Inoue et al. | |
| 5,779,672 A | 7/1998 | Dormandy, Jr. | |
| 5,782,812 A | 7/1998 | Hart et al. | |
| 5,782,916 A | 7/1998 | Pintauro et al. | |
| 5,785,640 A | 7/1998 | Kresch et al. | |
| 5,795,288 A | 8/1998 | Cohen | |
| 5,800,339 A | 9/1998 | Salama | |
| 5,830,228 A | 11/1998 | Knapp et al. | |
| 5,830,780 A | 11/1998 | Dennison et al. | |
| 5,836,951 A | 11/1998 | Rosenbluth et al. | |
| 5,843,126 A | 12/1998 | Jameel | |
| 5,846,180 A | 12/1998 | Kulisz et al. | |
| 5,868,141 A | 2/1999 | Ellias | |
| 5,885,204 A | 3/1999 | Vergano | |
| 5,908,379 A | 6/1999 | Schaefer et al. | |
| 5,916,198 A | 6/1999 | Dillow | |
| 5,964,806 A | 10/1999 | Cook et al. | |
| 5,989,180 A | 11/1999 | Norton | |
| 5,989,288 A | 11/1999 | Pintauro et al. | |
| 5,992,419 A | 11/1999 | Sterzer et al. | |
| 5,992,700 A | 11/1999 | McGlothlin et al. | |
| 6,013,102 A | 1/2000 | Pintauro et al. | |
| 6,021,781 A | 2/2000 | Thompson et al. | |
| 6,027,442 A | 2/2000 | Von Iderstein | |
| 6,042,535 A | 3/2000 | Porter | |
| 6,045,498 A | 4/2000 | Burton et al. | |
| 6,060,639 A | 5/2000 | Petrick | |
| 6,063,119 A | 5/2000 | Pintauro et al. | |
| 6,095,969 A | 8/2000 | Karram et al. | |
| 6,102,848 A | 8/2000 | Porter | |
| 6,119,697 A | 9/2000 | Engel et al. | |
| 6,127,010 A | 10/2000 | Rudy | |

(56) References Cited

U.S. PATENT DOCUMENTS

| | | | |
|---|---|---|---|
| 6,143,037 A | 11/2000 | Goldstein et al. | |
| 6,171,298 B1 | 1/2001 | Matsuura et al. | |
| 6,183,520 B1 | 2/2001 | Pintauro et al. | |
| 6,240,968 B1 | 6/2001 | Bigonzi-Jaker et al. | |
| 6,251,138 B1 | 6/2001 | Nadol, Jr. et al. | |
| 6,261,312 B1 | 7/2001 | Dobak, III et al. | |
| 6,287,290 B1 | 9/2001 | Perkins et al. | |
| 6,293,923 B1 | 9/2001 | Yachia et al. | |
| 6,311,689 B1 | 11/2001 | Tihon | |
| 6,312,405 B1 | 11/2001 | Meyer et al. | |
| 6,358,200 B1 | 3/2002 | Grossi | |
| 6,372,195 B1 | 4/2002 | Schutt et al. | |
| 6,379,378 B1 | 4/2002 | Werneth et al. | |
| 6,398,718 B1 | 6/2002 | Yachia et al. | |
| 6,398,738 B1 | 6/2002 | Miller | |
| 6,443,947 B1 | 9/2002 | Marko et al. | |
| 6,461,332 B1 | 10/2002 | Mosel et al. | |
| 6,463,332 B1 | 10/2002 | Aldrich | |
| 6,464,999 B1 | 10/2002 | Huo et al. | |
| 6,503,264 B1 | 1/2003 | Birk | |
| 6,527,761 B1 | 3/2003 | Soltesz et al. | |
| 6,544,224 B1 | 4/2003 | Steese-Bradley | |
| 6,544,287 B1 | 4/2003 | Johnson et al. | |
| 6,547,804 B2 | 4/2003 | Porter et al. | |
| 6,579,225 B2 | 6/2003 | Pregenzer et al. | |
| 6,602,276 B2 | 8/2003 | Dobak, III et al. | |
| 6,635,267 B1 | 10/2003 | Myoshi et al. | |
| 6,656,194 B1 | 12/2003 | Gannoe et al. | |
| 6,682,473 B1 | 1/2004 | Matsuura et al. | |
| 6,685,671 B1 | 2/2004 | Oishi et al. | |
| 6,706,069 B2 | 3/2004 | Berger | |
| 6,736,793 B2 | 5/2004 | Meyer et al. | |
| 6,746,421 B2 | 6/2004 | Yachia et al. | |
| 6,840,995 B2 | 1/2005 | Lin et al. | |
| 6,849,061 B2 | 2/2005 | Wagner | |
| 6,852,095 B1 | 2/2005 | Ray | |
| 6,974,463 B2 | 12/2005 | Magers et al. | |
| 6,976,950 B2 | 12/2005 | Connors et al. | |
| 6,976,951 B2 | 12/2005 | Connors et al. | |
| 6,988,983 B2 | 1/2006 | Connors et al. | |
| 6,997,871 B2 | 2/2006 | Sonnenchein et al. | |
| 7,014,860 B1 | 3/2006 | Kawata et al. | |
| 7,074,178 B2 | 7/2006 | Connors et al. | |
| 7,083,626 B2 | 8/2006 | Hart et al. | |
| 7,112,185 B2 | 9/2006 | Hart et al. | |
| 7,150,853 B2 | 12/2006 | Lee et al. | |
| 7,229,475 B2 | 6/2007 | Glazier | |
| 7,232,445 B2 | 6/2007 | Kortenbach et al. | |
| 7,374,532 B2 | 5/2008 | Connors et al. | |
| 7,390,317 B2 | 6/2008 | Taylor et al. | |
| 7,470,228 B2 | 12/2008 | Connors et al. | |
| 7,484,510 B2 | 2/2009 | Connors et al. | |
| 7,527,605 B2 | 5/2009 | Evans | |
| 7,540,876 B2 | 6/2009 | Connors et al. | |
| 7,632,291 B2 | 12/2009 | Stephens | |
| 7,641,643 B2 | 1/2010 | Michal et al. | |
| 7,691,051 B2 | 4/2010 | Connors et al. | |
| 7,766,814 B2 | 8/2010 | Walsh | |
| 7,771,395 B2 | 8/2010 | Hart et al. | |
| 7,811,221 B2 | 10/2010 | Gross | |
| 7,857,827 B2 | 12/2010 | Measamer | |
| 8,016,740 B2 | 9/2011 | Connors et al. | |
| 8,025,064 B2 | 9/2011 | Connors et al. | |
| 8,057,537 B2 | 11/2011 | Zilla et al. | |
| 8,062,205 B2 | 11/2011 | Timm et al. | |
| 8,298,132 B2 | 10/2012 | Connors et al. | |
| 8,574,146 B2 | 11/2013 | Gillespie, Jr. et al. | |
| 8,882,653 B2 | 2/2014 | Gillespie et al. | |
| 8,721,520 B2 | 5/2014 | Caira et al. | |
| 8,858,460 B2 | 10/2014 | Connors et al. | |
| 8,864,649 B2 | 10/2014 | Cahill et al. | |
| 8,894,563 B2 | 11/2014 | Connors et al. | |
| 8,961,392 B2 | 2/2015 | Cao et al. | |
| 8,992,412 B2 | 3/2015 | Cahill et al. | |
| 9,044,209 B2 | 6/2015 | Dayton et al. | |
| 9,427,295 B2 | 8/2016 | Connors et al. | |
| 9,498,195 B2 | 11/2016 | Schutt et al. | |
| 9,615,911 B2 | 4/2017 | Connors et al. | |
| 9,801,658 B2 | 10/2017 | Connors et al. | |
| 10,327,880 B2 | 6/2019 | Connors et al. | |
| 10,383,510 B2 | 8/2019 | Schutt et al. | |
| 10,531,894 B2 | 1/2020 | Connors et al. | |
| 10,543,071 B2 | 1/2020 | Cahil et al. | |
| 10,799,268 B2 | 10/2020 | Connors et al. | |
| 2001/0044595 A1 | 11/2001 | Reydel et al. | |
| 2002/0026226 A1 | 2/2002 | Ein | |
| 2002/0055730 A1 | 5/2002 | Yachia et al. | |
| 2002/0082551 A1 | 6/2002 | Yachia et al. | |
| 2002/0107490 A1 | 8/2002 | Butterfield et al. | |
| 2002/0120200 A1 | 8/2002 | Brockway et al. | |
| 2002/0165427 A1 | 11/2002 | Yachia et al. | |
| 2004/0111006 A1 | 6/2004 | Alferness et al. | |
| 2004/0143319 A1 | 7/2004 | Schwartz et al. | |
| 2004/0215177 A1 | 10/2004 | Swanson | |
| 2004/0260272 A1 | 12/2004 | Friedman et al. | |
| 2005/0070995 A1 | 3/2005 | Zilla et al. | |
| 2006/0252983 A1 | 11/2006 | Lembo et al. | |
| 2006/0264697 A1 | 11/2006 | Timm et al. | |
| 2007/0093857 A1 | 4/2007 | Rogers et al. | |
| 2007/0106233 A1 | 5/2007 | Huang et al. | |
| 2007/0202151 A1 | 8/2007 | Lee et al. | |
| 2007/0213660 A1 | 9/2007 | Richards et al. | |
| 2007/0225803 A1 | 9/2007 | Connors et al. | |
| 2008/0027304 A1 | 1/2008 | Pardo et al. | |
| 2008/0086082 A1 | 4/2008 | Brooks | |
| 2008/0086149 A1 | 4/2008 | Diamant et al. | |
| 2008/0275428 A1 | 11/2008 | Tegg et al. | |
| 2009/0171241 A1 | 7/2009 | Garcia et al. | |
| 2010/0152654 A1 | 6/2010 | Tilson et al. | |
| 2010/0222802 A1* | 9/2010 | Gillespie, Jr. | A61F 2/2481 606/192 |
| 2010/0249701 A1 | 9/2010 | Goebel | |
| 2010/0251837 A1 | 10/2010 | Bouasaysy et al. | |
| 2011/0276041 A1 | 11/2011 | Nobis et al. | |
| 2012/0305329 A1 | 12/2012 | Keady et al. | |
| 2013/0211440 A1 | 8/2013 | Schwab et al. | |
| 2014/0228871 A1 | 8/2014 | Cohen et al. | |
| 2014/0309679 A1* | 10/2014 | Maisano | A61B 17/3478 606/170 |
| 2017/0021128 A1 | 1/2017 | Erbey, II et al. | |
| 2017/0065160 A1 | 3/2017 | Connors et al. | |
| 2017/0354491 A1 | 12/2017 | Connors et al. | |
| 2018/0228512 A1 | 8/2018 | Connors et al. | |
| 2019/0008443 A1* | 1/2019 | O'Dea | A61B 5/1076 |
| 2020/0121342 A1 | 4/2020 | Sullivan, III | |
| 2020/0146799 A1 | 5/2020 | Connors et al. | |
| 2020/0163543 A1 | 5/2020 | Schutt et al. | |
| 2020/0253636 A1 | 8/2020 | Connors | |
| 2020/0254226 A1 | 8/2020 | Connors | |
| 2021/0128197 A1 | 5/2021 | Connors | |
| 2021/0138556 A1 | 5/2021 | Cahill | |

FOREIGN PATENT DOCUMENTS

| | | |
|---|---|---|
| EP | 1 813 303 | 12/2008 |
| FR | 2788224 | 7/2000 |
| FR | 2774579 | 8/2000 |
| GB | 2023405 | 7/1982 |
| JP | 01-285263 | 11/1989 |
| JP | 5049690 | 3/1993 |
| JP | H08-252321 | 10/1996 |
| JP | 2000-325328 | 11/2000 |
| JP | 2007-190430 | 8/2007 |
| WO | WO 90/13321 | 11/1990 |
| WO | WO 91/03267 | 3/1991 |
| WO | WO 95/019200 | 7/1995 |
| WO | WO 96/02214 | 2/1996 |
| WO | WO 99/24106 | 5/1999 |
| WO | WO 00/27405 | 7/2000 |
| WO | WO 00/54701 | 9/2000 |
| WO | WO 00/54702 | 9/2000 |
| WO | WO 01/02042 | 1/2001 |
| WO | WO 01/57093 | 8/2001 |
| WO | WO 01/64145 | 9/2001 |

(56) References Cited

FOREIGN PATENT DOCUMENTS

| | | |
|---|---|---|
| WO | WO 01/66052 | 9/2001 |
| WO | WO 01/78576 | 10/2001 |
| WO | WO 02/38038 | 5/2002 |
| WO | WO 02/065894 | 8/2002 |
| WO | WO 02/100300 | 12/2002 |
| WO | WO 03/015673 | 2/2003 |
| WO | WO 03/022164 | 3/2003 |
| WO | WO 04/030518 | 4/2004 |
| WO | WO 04/091592 | 10/2004 |
| WO | WO 04/096071 | 11/2004 |
| WO | WO 05/058203 | 6/2005 |
| WO | WO 06/086627 | 8/2006 |
| WO | WO 07/050546 | 5/2007 |
| WO | WO 07/059160 | 5/2007 |
| WO | WO 07/103809 | 9/2007 |
| WO | WO 08/100433 | 8/2008 |
| WO | WO 09/149108 | 12/2009 |
| WO | WO 10/068467 | 6/2010 |
| WO | WO 14/026028 | 2/2014 |
| WO | WO 20/047402 | 3/2020 |

OTHER PUBLICATIONS

U.S. Appl. No. 16/503,405, filed Jul. 3, 2019, Schutt et al.
U.S. Appl. No. 16/557,555, filed Aug. 30, 2019, Sulivan, III et al.
U.S. Appl. No. 16/741,563, filed Jan. 13, 2020, Connors et al.
U.S. Appl. No. 17/025,945, filed Sep. 18, 2020, Connors et al.
International Preliminary Report on Patentability for International Application No. PCT/US 20/17052, dated Aug. 10, 2021.
Abbar et al., "Une revolution tranquille: I endoprothese urethrale . . . ", Progres en Urologie, 3.771-777 (1993). (w/Google Translation).
AMS Sphincter 800, "Brochure: AMS Sphincter 800, Urinary Prosthesis, Dry Facts of Incontinence Treatment, Pfizer American Medical Systems®" Jun. 1, 1991.
Barbalias et al., "Interstital Cystitus. Bladder Training with Intravesical Oxybutynin," The Journal of Urology, vol. 163, pp. 1818-1822, Jun. 2000.
Bloom et al., "Abstract, Barometers and bladders: a primer on pressures," Website PubMed, Mar. 2000 in 1 page.
Boston Scientific Target Detachable Silicone Balloon, Product Information, (Part No. ES-05827 Rev. A); published by Boston Scientific and Target Therapeutics at Fremont, CA or Natick.MA; relevant pages consist of the entire document (total of 24 pages); print-out in 2 pages from the USPTO's Trademark Electronic Search System identifying the date of first used in commerce of on or about Aug. 1998.
Brash et al., "Development of Block Copolyether-Urethane Intra-Aortic Balloons and Other Medical Devices," Journal of Biomedical Materials Research, vol. 7, pp. 313-334, Jul. 1973.
Colin et al., "Abstract, New data on the diagnosis and treatment of urinary stress incontinence in women," WebSite PubMed, Feb. 2000 in 1 page.
Craggs et al., "A preliminary report on a new hydraulic sphincter for controlling urinary incontenace," Journal of Medical Engineering & Technology, 15:58-62 (1991).
Damasar et al., "The Effect of Urinary Bladder Shape on its Mechanics During Filling," Pergamon, vol. 6, pp. 725-732, 1995.
Damaser et al., "Abstract, Whole bladder mechanics during filling," Website PubMed, Oct. 1999 in 1 page.
Dass et al., "Elastic fibres in the vesicourethral junction and urethra of the guinea pig: quantification with computerised image analysis," Journal of Anatomy, Molecular, Cellular and Experimental Morphology, vol. 195, Part 3, pp. 447-453, Oct. 1999.
Djavan et al., "Decreased Elastin Gene Expression in Noncompliant Human Bladder Tissue. A Competitive Reverse Transcriptase-Polymerase Chain Reaction Analysis," Journal of Urology, vol. 160, pp. 1658-1662, Nov. 1998.

Gilmour et al., "A New Technique for Dynamic Analysis of Bladder Compliance," The Journal of Urology, vol. 150, pp. 1200-1203, Oct. 1993.
Gleeson et al., "Abstract, Experimental development of a fixed volume, gravity draining, prosthetic urinary bladder," Website PubMed, Jul. 1990 in page.
Gorton et al., "Abstract, Ambulatory urodynamics: do they help clinical management," Website PubMed, Mar. 2000.
Gruneberger et al., Entwicklung eines magnetischen Urethralverschlusses . . . , Zentralblatt fur Gynokologie 115:328-331 (1993).
Gundian et al., "Mayo Clinic Experience With the AS800 Artificial Urinary Sphincter for Urinary Incontinence After Transurethral Resection of Prostate or Open Prostatectomy," Urology, 41:318-321, (1993).
HK Medical, "Brochure: HK Medical Technologies Incorporated, Autocath™ 100," 1994.
Janknegt, et al. "Electrically Stimulated gracilis Sphincter for treatment of . . . ", Lancet, 340:1129-1130 (1992).
Jonas et al., "Abstract, Urodynamics of normal and disordered miction," Website PubMed, Oct. 1979 in 1 page.
Kohan et al., "Effect of aging on bladder function and the response to Outlet obstruction in female rats," Urol Res, 2000, 28: pp. 33-37.
Koo et al., "Temporal Expression of Elastic Fiber Components in Bladder Development," Connective Tissue Research, vol. 3701-20, pp. 1-11, 1998.
Kowalczyk et al., "Abstract, Office evaluation of the patient with an overactive Bladder," Website PubMed, Mar. 2000 in 1 page.
LabView Function and VI Reference Manual, National Instruments, Jan. 1998 Edition.
Lemack et al., "Abstract, Identifying patients who require urodynamic testing before Surgery for Stress incontinence based on questionnaire information and Surgical history," Website PubMed, Apr. 2000.
Lewis et al., "Abstract, Urodynamic protocol and central review of data for clinical trials in lower urinary tract dysfunction," Website PubMed, Mar. 2000 in 1 page.
Lonsway et al., "Abstract, Surgical and medical treatment options for urge incontinence," Website PubMed, Mar. 2000 in 1 page.
Lukkarinen et al., Treatment of Urinary Incotinence with an Implantable Prosthesis, Scand J. Urol Nephrol, 23:85-88 (1989).
Martan et al., "Abstract, The effect of bladder filling on changes in ultrasonography parameters of the lower urinary tract in women with urinary stress incontinence," Website PubMed, Jan. 2000 in 1 page.
Mikuma et al., "Voiding Dysfunction in Ileal Neobladder," The Journal of Urology, vol. 158 pp. 1365-1367, Oct. 1997.
Olsfanger et al., "Effect of Spinal Versus General Anesthesia on Bladder Compliance and Intraabdominal Pressure During Transurethral Procedures," Journal of Clinical Anesthesia, vol. 11, pp. 328-331, 1999.
Petrican et al., "Design of Miniaturized Bladder Volume Monitor and Subsequent Preliminary Evaluation on 41 Enuretic Patients," IEEE Transactions on Rehabilitation Engineering, vol. 6, No. 1, pp. 66-74, Mar. 1998.
Rosenbloom et al., "Elastic Fibers and Their Role in Bladder Extracellular Matrix," Muscle, Matrix and Bladder Function, vol. 385, pp. 161-184, 1995.
Scelsi et al., "Structure of the Lymphatic Microcirculation in the Human Urinary Bladder with Different Intraluminal Pressure and Distension," Lymphology, pp. 60-66, 1996.
Serels et al., "Abstract, Surgical treatment for Stress urinary incontinence associated with valsalva induced detrusor instability," Website MedPub, Mar. 2000.
Shekarriz et al., "Surgical Complications of Bladder Augmentation: Comparison Between Various Enterocystoplasties in 133 Patients," Elsevier Science Inc., Pediatric Urology 55, pp. 123-128, 2000.
Stanton et al., "The Mechanism of Continence", Surgery of Female Incontinence, 2d Ed. pp. 1-21, 1986.
Stöhrer et al., "Die DetrusOrmyektomie (Autoaugmentation) in der Dehandlung der Hyperreflexiven Low-compliance-Blasé," Der Urologe A), pp. 30-37, 1999.
Summary of Dialog/Derwent World Pat. computer search, Mar. 17, 1995.

(56) References Cited

OTHER PUBLICATIONS

Summary of Dialog/Medline/Biosis/SciSearch/Embase computer search, Mar. 17, 1995.

Ukimura et al., "Noninvasive Evaluation of Bladder Compliance in Children Using Ultrasound Estimated Bladder Weight," The Journal of Urology, vol. 160 pp. 1459-1462, Oct. 1998.

Urge Incontinence and the Unstable Bladder, Practical Urogynecology, Chapter 8—Incontinence and the Unstable Bladder, pp. 191-214.

UroMed, "Preliminary Prospectus: UroMed Corporation, Paine Webber Incorporated Vector Securities International, Inc." Jan. 24, 1994.

Valentini et al., "Abstract, A mathematical micturition to restore simple flow recordings in healthy and Symptomatic individuals and enhance uroflow interpretation," Website PubMed, 2000 in 1 page.

Wagg et al., "Visco-elastic Properties of Isolated Detrusor Smooth Muscle," Scandinavian Journal of Urology Nephoral, Suppl. 201, pp. 12-18, 1999.

Weld et al., "Difference in Bladder Compliance with Time and Associations of Bladder Management with Compliance in Spinal Cord Injured Patients," The Journal of Urology, vol. 163, pp. 1228-1233, Apr. 2000.

Wylie et al., "Fluid Transients in Systems," Prentice Hall, (1993) pp. 59-70.

Winkler, et al., "Twelve-Month Efficacy and Safety Data for the "Stress Incontinence Control, Efficacy and Safety Study": A Phase III, Multicenter, Prospective, Randomized, Controlled Study Treating Female Stress Urinary Incontinence Using the Vesair Intravesical Balloon," Female Pelvic Medicine & Reconstructive Surgery, vol. 24, No. 3, pp. 222-231 dated May/Jun. 2018.

Statement of Relevance regarding Vesair Intravesical Balloon by Kevin Connors, signed Oct. 18, 2021 in 3 pages.

Rovner, et al., "A Randomized, Controlled Clinical Trial of a Novel Intravesical Pressure Attenuation Device for the Treatment of Stress Urinary Incontinence," The Journal of Urology, vol. 190, pp. 2243-2250, dated Dec. 2013.

Statement of Relevance regarding Pressure Attenuation Device by Kevin Connors, signed Oct. 18, 2021, in 3 pages.

\* cited by examiner

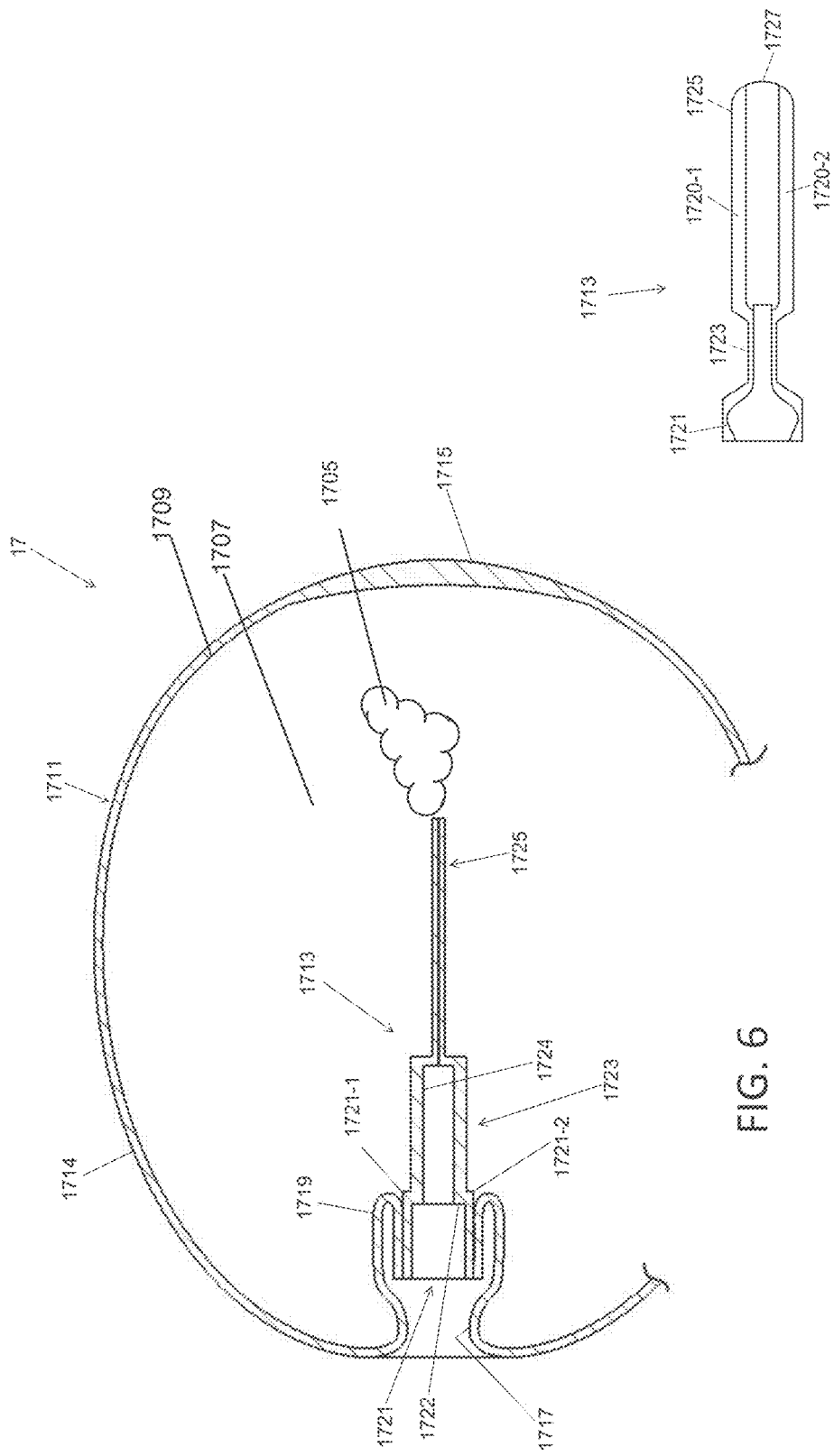

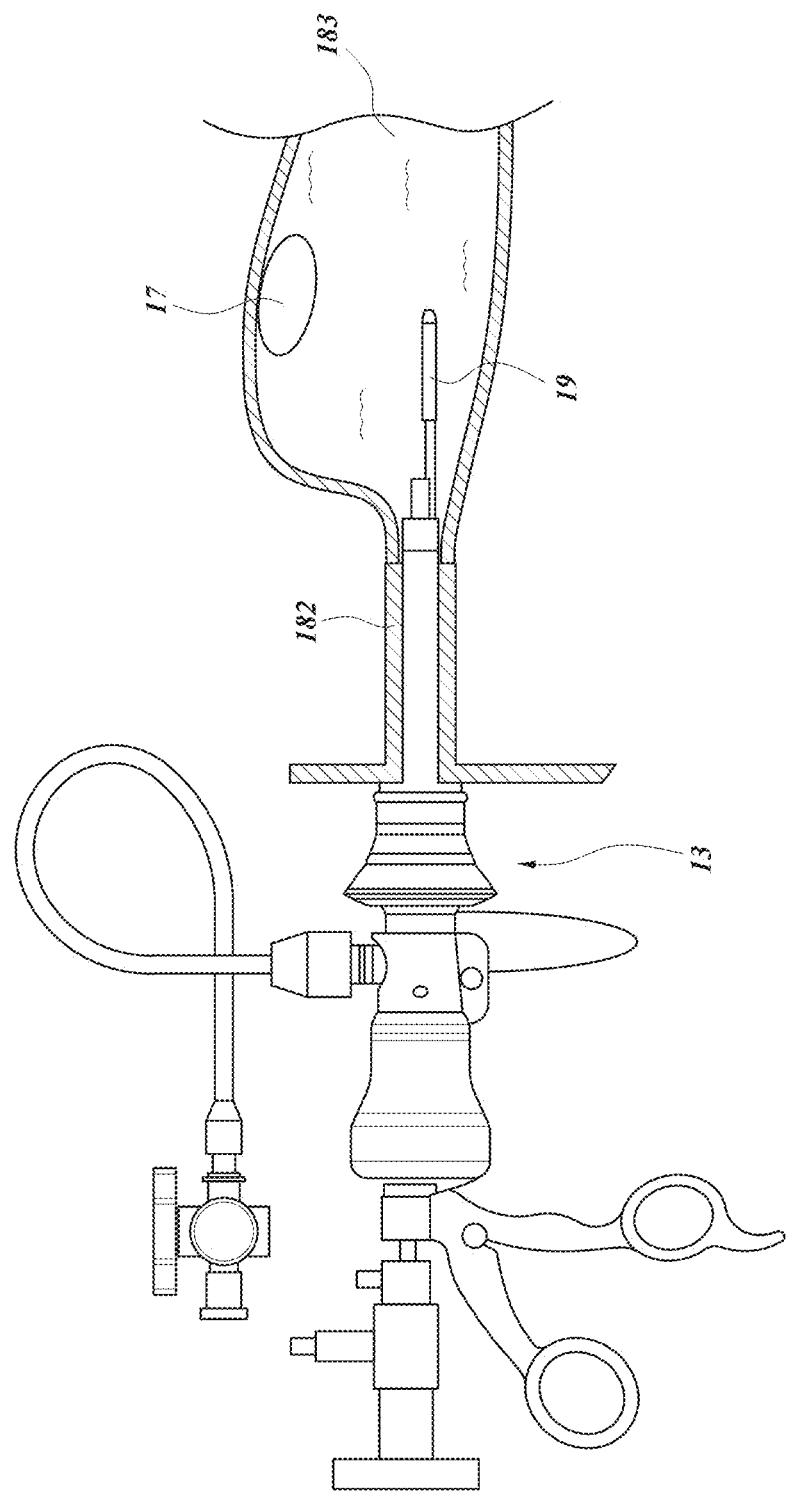

PRESSURE ATTENUATION DEVICE

CROSS-REFERENCE TO RELATED APPLICATIONS

This application is a continuation of U.S. patent application Ser. No. 16/784,045, filed on Feb. 6, 2020, which claims priority to U.S. Provisional Application No. 62/802,622, filed on Feb. 7, 2019, the entire contents of all of the above applications are incorporated by reference herein and made a part of this specification for all purposes. Any and all applications for which foreign or domestic priority claim is identified in the Application Data Sheet as filed with the present application are hereby incorporated.

BACKGROUND

Field

The present disclosure relates to methods and systems for performing medical procedures on anatomical structures of the body. Such medical procedures may involve, for example, attenuating transient pressure waves in anatomical structures of the body, for example, by implanting a pressure attenuation device in anatomical structure of the body that is subjected to such pressure waves.

Description of the Related Art

Pressure waves are known to propagate through incompressible fluids in various anatomical structures of the body. These pressure waves may be caused by normally-occurring events within the body, such as a beating heart, breathing in the lungs, peristalsis actions in the GI tract, and movement of the muscles of the body. Alternatively, these pressure waves may be caused by sudden events, such as coughing, laughing, external trauma to the body, and movement of the body relative to gravity. As the elasticity of the surrounding tissues and organs, sometimes referred to as compliance, decreases, the propagation of these pressure waves increases. These pressure waves have many undesirable effects ranging from discomfort to stress on the organs and tissue to fluid leakage to renal failure to stroke to heart attack to blindness.

Urinary tract disorders, such as frequency, urgency, incontinence, and cystitis, are a widespread problem in the United States and throughout the world, affecting people of all ages, both physiologically and psychologically. Urine is primarily composed of water and is a virtually incompressible fluid in the typical pressure ranges that are present within the human bladder. The relationship between the maximum urethral pressure and the intravesical pressure for normal voiding of the bladder is well-defined. During normal voiding, relaxation of the urethra occurs before the detrusor muscle contracts to cause the intravesical pressure to exceed the urethral pressure.

Intravesical pressure spikes often result from volumetric tissue displacement in response to gravity, muscular activity or rapid acceleration. The lack of compliance of the bladder and the urine contained in the bladder with respect to events of high frequency, high intensity and short wavelength results in minimal fluidic pressure attenuation of the higher frequency pressure wave(s) and results in high intravesical pressures that are directly transmitted to the bladder neck and urethra, which may or may not cause detrusor contractions. Under these conditions, the urethra may act as a volumetric pressure relief mechanism, allowing a proportional volume of fluid to escape the bladder, thereby lowering the intravesical pressure to a tolerable level. The urethra has a maximum urethral pressure value, and when the intravesical pressure exceeds the maximum urethral pressure, fluid will escape the bladder. Under these conditions, nerve receptors in the bladder and/or bladder neck and/or trigone trigger a detrusor contraction that may lead to matriculation (frequency) or may subside without matriculation (urgency) or may lead to the intravesical pressure exceeding the maximum urethral pressure resulting in fluid escaping the bladder (stress incontinence).

For the vast majority of patients suffering from problems of urinary tract disorders, such as frequency, urgency, stress and urge incontinence and cystitis, the cause and/or contributor to bladder dysfunction is a reduction of overall dynamic bladder compliance, as opposed to a reduction of steady-state bladder compliance. These patients may often have bladders that are compliant in steady-state conditions but that become non-dynamically compliant when subjected to external pressure events having a short duration of, for example, less than 5 seconds or, in some cases, less than 0.5 seconds. Reduction in dynamic compliance of the bladder is often caused by aging, use, distention, childbirth and trauma. In addition, the anatomical structure of the bladder in relation to the diaphragm, stomach, and uterus (for women) causes external pressure to be exerted on the bladder during physical activities, such as talking, walking, laughing, sitting, moving, turning, and rolling over. For a patient suffering from stress incontinence due to lack of dynamic compliance in the bladder, when the intravesical pressure exceeds the maximum urethral pressure, leakage occurs.

In light of the foregoing, a number of attempts have been made to combat urinary tract disorders. One such attempt has been to implant a compressible, pressure-attenuating device in the bladder in order to lower the intravesical pressure. This approach is disclosed, for example, in the following documents, all of which are incorporated herein by reference: U.S. Pat. No. 6,682,473, Matsuura et al., issued Jan. 27, 2004; U.S. Pat. No. 7,074,178, Connors et al., issued Jul. 11, 2006; and U.S. Patent Application Publication No. 2010/0222802, Gillespie, Jr. et al., published Sep. 2, 2010. According to one aspect of the foregoing approach, a compressible device is inserted, in a compacted state, into the bladder of a patient through the patient's urethra, and, then, once in the bladder, the compressible device is expanded, for example, by inflation with atmospheric air. A delivery system may be used to deliver the compressible device through the urethra and into the bladder and also may be used to expand the compressible device from its compacted state to its expanded state and to deploy the compressible device, once expanded, from the delivery system. If removal or replacement of the compressible device is desired, a removal system may be used to remove the compressible device from the bladder through the urethra.

SUMMARY

The systems, methods and devices of this disclosure each have several innovative aspects, no single one of which is solely responsible for the desirable attributes disclosed herein.

In an aspect, the present disclosure improves upon prior pressure attenuation devices for use in the bladder. Accordingly, it is an object of certain embodiments of the disclosure to provide a method and system for performing a medical procedure on an anatomical structure, such as a bladder, of a body. The medical procedure may be performed, for example, to attenuate transient pressure waves in the anatomical structure and may involve, for example, implanting a pressure attenuation device in the anatomical structure, such as a bladder, subject to such pressure waves. Such a method and system may be used in, but is not limited to use in, treating urinary tract disorders.

Certain embodiments comprise a method of treating a condition affecting the bladder. The method can include the steps of implanting a pressure attenuation device into a human or animal body. The condition affecting the bladder can comprise: urinary incontinence, urinary tract cancer, an infection affecting the bladder, or an inflammatory, condition affecting the bladder.

In certain embodiments, a pressure attenuation device for use in a body can include a balloon comprising an outer wall and defining an interior chamber therein. The outer wall of the balloon can have a minimum wall thickness of between 0.001 inches and 0.00175 inches. The balloon can be configured to elastically deform up to at least to an internal pressure of 90 cm $H_2O$. In some embodiments, the pressure attenuation device can also include one or more of the following features in any combination: (a) a high vapor pressure media having a vapor pressure of between 155 cm $H_2O$-185 cm $H_2O$ at 37 degrees Celsius; (b) a high vapor pressure media media having a vapor pressure of between 155 cm $H_2O$-165 cm $H_2O$ at 37 degrees Celsius; (c) wherein the high vapor pressure media is positioned within the interior chamber; (d) wherein the high vapor pressure media comprises a PFC; (e) wherein the balloon elastically deforms and increases in volume by at least 10% but less than 90% when the internal pressure within the balloon is increased from 2.5 cm $H_2O$ to 90 cm $H_2O$; (f) wherein the balloon elastically deforms and increases in volume by at least 75% but less than 90% when the internal pressure within the balloon is increased from 2.5 cm $H_2O$ to 90 cm $H_2O$; (g) wherein the balloon elastically deforms to at least an internal pressure of 120 cm $H_2O$; (h) wherein the balloon has a natural volume of between 1 and 180 cc, between 10 and 60 cc, between 24 ml and 40 ml, or between 25 ml and 29 ml; (i) wherein the balloon elastically deforms between internal pressures of 2.5 cm $H_2O$ to 90 cm $H_2O$ for at least 15 cycles; (j) wherein the balloon elastically deforms between internal pressures of 2.5 cm $H_2O$ to 90 cm $H_2O$ for at least 25 cycles; (k) wherein the balloon elastically deforms between internal pressures of 2.5 cm $H_2O$ to 90 cm $H_2O$ for at least 50 cycles; and/or (l) wherein the balloon elastically deforms between internal pressures of 2.5 cm $H_2O$ to 90 cm $H_2O$ for at least 100 cycles.

In certain embodiments, a pressure attenuation device for use in a body can include a balloon comprising an outer wall and defining an interior chamber therein. The device can include a high vapor pressure media. The balloon can be configured to deform elastically at least up to an internal pressure within the chamber of 90 cm $H_2O$.

In certain embodiments, a pressure attenuation device can include a balloon comprising an outer wall and defining an interior chamber therein. The balloon can be configured to elastically deform up to at least to an internal pressure of 90 cm $H_2O$. A high vapor pressure media having a vapor pressure of between 155 cm-185 cm $H_2O$ at 37 degrees Celsius can be within the balloon. In some embodiments, the pressure attenuation device can also include one or more of the following features in any combination: (a) wherein the high vapor pressure media has a vapor pressure of between 155 cm $H_2O$-165 cm $H_2O$ at 37 degrees Celsius; (b) wherein the high vapor pressure media is positioned within the interior chamber (c) wherein the high vapor pressure media comprises a PFC; (d) wherein the balloon elastically deforms between internal pressures of 2.5 cm $H_2O$ to 90 cm $H_2O$ for at least 15 cycles, 25 cycles, 50 cycles or 100 cycles; and/or (e) wherein the balloon has a natural volume of between 1 and 180 cc, between 10 and 60 cc, between 24 ml and 40 ml, or between 25 ml and 29 ml.

In certain embodiments, a pressure attenuation device for use in a body includes a balloon comprising an outer wall and defining an interior chamber therein. The balloon can be configured to elastically deform and increase in volume by at least 50% but less than 190% when an internal pressure within the balloon is increased from 2.5 cm $H_2O$ to 90 cm $H_2O$. In some embodiments, the pressure attenuation device can also include one or more of the following features in any combination: (a) wherein the balloon is configured to elastically deform and increase in volume by at least 65% but less than 100% when a pressure within the balloon is increased from 2.5 cm $H_2O$ to 90 cm $H_2O$; (b) wherein the balloon is configured to elastically deform and increase in volume by at least 75% but less than 90% when a pressure within the balloon is increased from 2.5 cm $H_2O$ to 90 cm $H_2O$; (c) wherein the balloon is configured to elastically deform and increase in volume by at least 20% but less than 150% when a pressure within the balloon is increased from 2.5 cm $H_2O$ to 70 cm $H_2O$; (d) wherein the balloon is configured to elastically deform and increase in volume by at least 30% but less than 100% when a pressure within the balloon is increased from 2.5 cm $H_2O$ to 70 cm $H_2O$; (e) wherein the balloon is configured to elastically deform and increase in volume by at least 45% but less than 60% when a pressure within the balloon is increased from 2.5 cm $H_2O$ to 70 cm $H_2O$; (f) wherein the balloon is configured to elastically deform and increase in volume by at least 10% but less than 45% when a pressure within the balloon is increased from 2.5 cm $H_2O$ to 40 cm $H_2O$; (g) wherein the balloon is configured to elastically deform and increase in volume by at least 18% but less than 30% when a pressure within the balloon is increased from 2.5 cm $H_2O$ to 40 cm $H_2O$; (h) wherein the balloon is configured to elastically deform and increase in volume by at least 19% but less than 27% when a pressure within the balloon is increased from 2.5 cm $H_2O$ to 40 cm $H_2O$; (i) comprising a high vapor pressure media having a vapor pressure of between 155 cm $H_2O$-185 cm $H_2O$ at 37 degrees Celsius; (j) comprising a high vapor pressure media having a vapor pressure of between 155 cm $H_2O$-165 cm $H_2O$ at 37 degrees Celsius; (k) wherein the high vapor pressure media is positioned within the interior chamber; (l) wherein the high vapor pressure media comprises a PFC; (m) wherein the balloon elastically deforms between internal pressures of 2.5 cm $H_2O$ to 90 cm $H_2O$ for at least 15 cycles, 25 cycles, 50 cycles or 100 cycles; (n) wherein the balloon has a natural volume of between 1 and 180 cc, between 10 and 60 cc, between 24 ml and 40 ml, or between 25 ml and 29 ml; and/or (o) wherein the balloon has a minimum wall thickness of between 0.001 inches and 0.00175 inches.

In several embodiments, a pressure attenuation device for use in a body comprise a balloon comprising an outer wall and defining an interior chamber therein; and a high vapor pressure media. The balloon is configured to deform elastically at least up to an internal pressure within the chamber of 90 cm $H_2O$. In some embodiments, the pressure attenuation device can also include one or more of the following features in any combination: (a) wherein the balloon elastically deforms between internal pressures of 2.5 cm $H_2O$ to 90 cm $H_2O$ for at least 15 cycles, 25 cycles, 50 cycles or 100 cycles; (b) wherein the balloon is configured to deform elastically at least up to an internal pressure within the chamber of 100 cm $H_2O$; (c) wherein the balloon elastically deforms between internal pressures of 2.5 cm $H_2O$ to 100 cm $H_2O$ for at least 15 cycles, 25 cycles, 50 cycles or 100 cycles; (d) wherein the balloon is configured to deform elastically at least up to an internal pressure within the chamber of 120 cm $H_2O$; (e) wherein the balloon elastically deforms between internal pressures of 2.5 cm $H_2O$ to 120 cm $H_2O$ for at least 15 cycles, 25 cycles, 50 cycles or 100 cycles; (f) wherein the balloon has a natural volume of between 1 and 180 cc, between 10 and 60 cc, between 24 ml and 40 ml, or between 25 ml and 29 ml; (g) wherein the balloon has a minimum wall thickness of between 0.001 inches- and 0.00175 inches; (h) wherein the high vapor pressure media has a vapor pressure of between 155 cm $H_2O$-185 cm $H_2O$ at 37 degrees Celsius; (i) wherein the high vapor pressure media has a vapor pressure of between 155 cm $H_2O$-165 cm $H_2O$ at 37 degrees Celsius; (j) wherein the high vapor pressure media is positioned within the interior chamber; (k) wherein the high vapor pressure media comprises a PFC; and/or (l) wherein the high vapor pressure media comprises a liquid at 37 degrees Celsius In certain embodiments, a pressure attenuation device comprises one or more features of the foregoing description. In certain embodiments, a pressure attenuation device comprises one or more features of the foregoing description and is configured to be placed within the bladder of a human.

Certain embodiments include a method of treating urinary incontinence in a human or animal body comprising implanting a pressure attenuation device comprising one or more features of the foregoing description within a bladder of the human or animal body and inflating the pressure attenuation device while in the bladder. In certain embodiments, the method also include removing the device from the bladder.

Certain embodiments include a pressure attenuation device comprising one or more features of the foregoing description configured to be implanted within a bladder of a human.

Certain embodiments include a pressure attenuation device comprising one or more features of the foregoing description configured to be implanted within a bladder of a human in an uninflated state and then inflated within the bladder.

Certain embodiments include a pressure attenuation device comprising one or more features of the foregoing description wherein the balloon comprises a bulb portion and a tail portion.

Certain embodiments include a pressure attenuation device comprising one or more features of the foregoing description wherein the balloon is seamless.

Further features and advantages will become apparent to those of skill in the art in view of the detailed description of preferred embodiments which follows, when considered together with the attached drawings and claims.

BRIEF DESCRIPTION OF THE DRAWINGS

In order to better understand the disclosure and to see how it may be carried out in practice, some preferred embodiments are next described, by way of non-limiting examples only, with reference to the accompanying drawings, in which like reference numerals denote corresponding though not necessarily identical features consistently throughout the embodiments in the attached drawings.

FIG. 6 is a fragmentary section view of the pressure attenuation device of FIGS. 5A through 5C.

FIG. 7 is a top view of the valve shown in FIGS. 5A through 5C.

DETAILED DESCRIPTION

Medical devices, methods, and apparatuses related thereto for use within the body are disclosed. The medical devices can include pressurized therapeutic devices, implants, implant delivery devices, implant retrieval devices, expandable membrane enclosures or balloons, sponges, attenuators, space occupying members, space creating devices, drug delivery devices, data collection devices, nerve stimulation devices, wave producing devices, vibration producing devices, pressure sensing devices, chemical sensing devices, volume sensing devices, and/or therapeutic devices. The medical devices can be used for many purposes and in many places within the body including, but not limited to the following systems of the human body: cardiovascular, pulmonary, renal/urological, gastrointestinal, hepatic/biliary, gynecological, neurological, musculoskeletal, otorhinolaryngological and ophthalmic, as well as in and around organs of the body and in intra- and inter-organ space. In particular, in many embodiments disclosed herein, the medical device is a pressure attenuation device which is configured to be placed within a patient's bladder. However, it should be appreciated that certain embodiments, aspects, and features of the pressure attenuation devices disclosed herein can find utility in other places in the body as outlined above and can be used as implants and medical devices that are not used for pressure attenuation and/or for pressure attenuation within the bladder and/or are used to provide other therapeutic benefits.

Embodiments of devices for treating one or more conditions of the bladder including devices that can be used for attenuating transient pressure waves propagating through the bladder, e.g., from coughing or laughing, to reduce and/or eliminate pressure spike-related incontinence are disclosed in one or more of U.S. Pat. Nos. 7,470,228, 7,074,178, 7,540,876, 8,574,146, 8,894,563 and U.S. Publication No. 2015/0216644. The entire contents of all of the above patents and patent publications are incorporated by reference herein for all purposes and are to be considered a part of this specification.

Figure 13A:
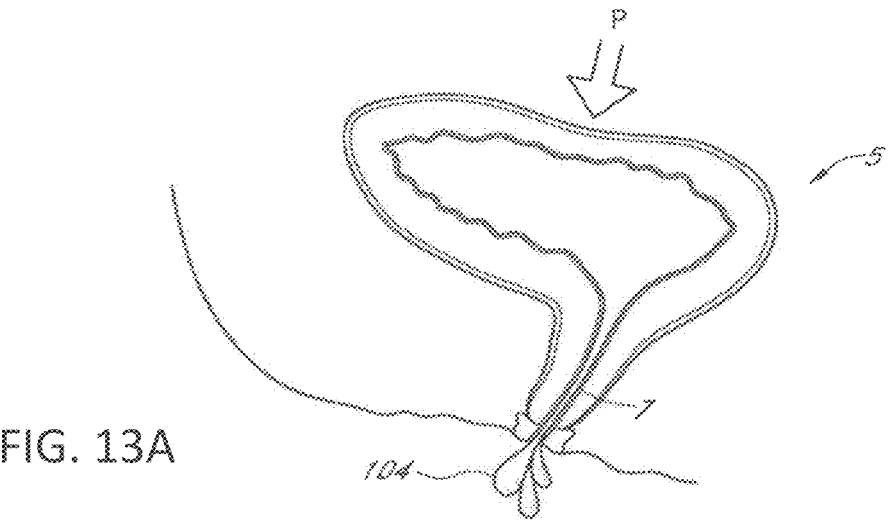
FIG. 13A illustrates a bladder experiencing pressure which causes urine leakage.
Figure 13B:
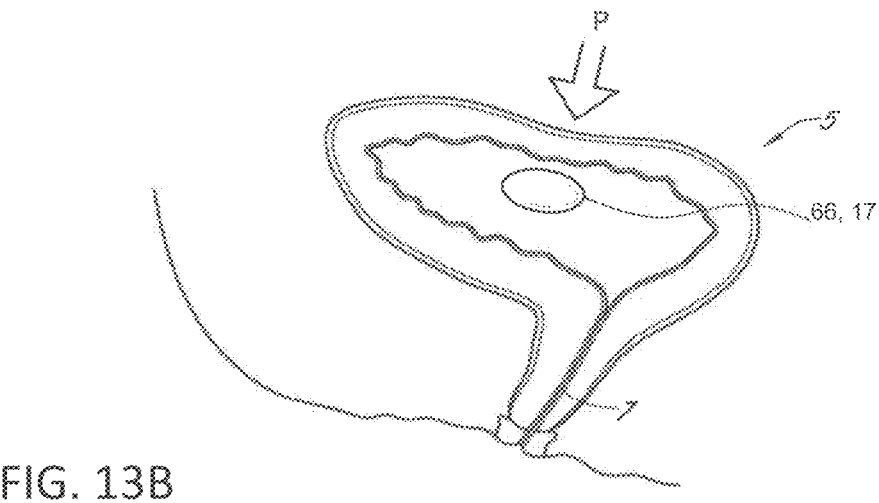
FIG. 13B shows the bladder of FIG. 13A with pressure attenuation device that absorbs the pressure so that there is no urine leakage.
Figure 14:
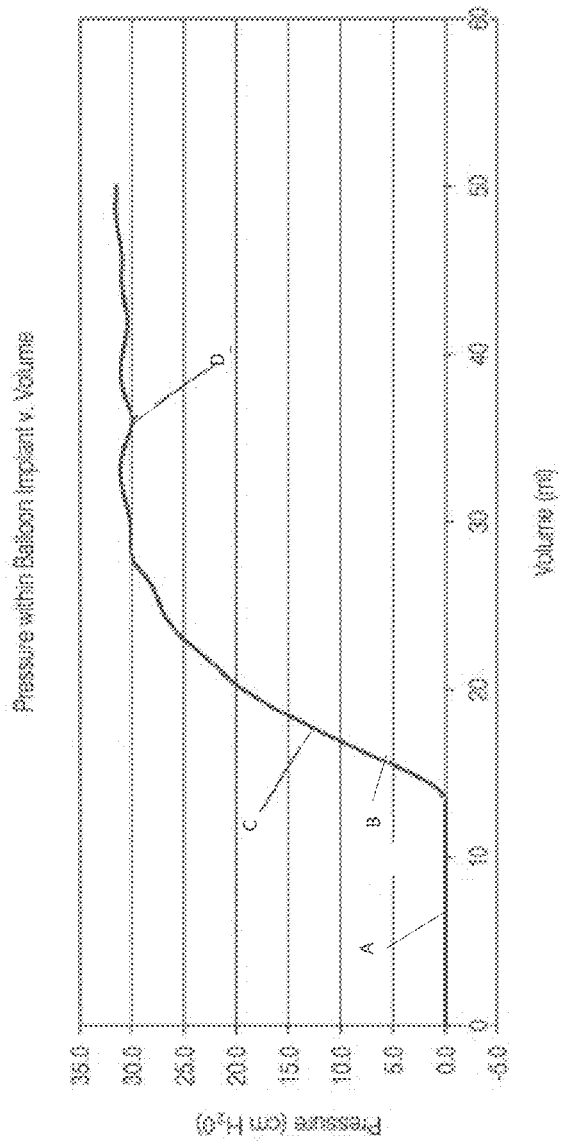
FIG. 14 charts the pressure within a pressure attenuation device verses the volume of the pressure attenuation device.

FIGS. 1-4 illustrate certain graphs of physiologic response to pressure, e.g., bladder response to transient pressure waves. FIGS. 5A-10B illustrate structural features which can be included in certain embodiments of a pressure attenuation device as disclosed herein. FIGS. 11A-12D illustrate graphs of various responses to pressure waves, including the response of a bladder, e.g., a model bladder, to transient pressure waves with and without a pressure attenuation device. FIGS. 13A-13B illustrates a cross section of a bladder with and without a pressure attenuation device which in certain embodiments can be configured according to certain embodiments disclosed herein. FIG. 14 illustrates a pressure versus volume curve for certain embodiments a pressure attenuation device disclosed herein, e.g., the pressure attenuation device's volumetric response to increases in interior pressure according to certain embodiments.

In one particular aspect, the disclosure relates generally to the field of urology and gynecology, and in particular to the treatment of disorders of the urinary tract caused by sudden fluctuations of intravesical pressure. More specifically, in this aspect methods and devices are provided for the diagnosis and treatment of urinary disorders such as incontinence, urgency, frequency, interstitial cystitis, irritable bladder syndrome, and neurogenic bladders.

Various embodiments of the pressure attenuation device can maintain a given pressure and or volume over time, despite gaseous exchange, are provided. Other embodiments can inflate or deflate over a given time period. Further embodiments can provide a constant force against, within or between a tissue, vessel, organ, or body cavity. Certain embodiments can be designed to maintain inflation in oxygen depleted environments.

Various instruments and implants are disclosed herein for the implantation of pressure attenuation device devices within the bladder via the urethra, open surgery, or percutaneously through the abdomen, back, vagina, bowel, rectum, or perineum. Certain embodiments of the implantable medical device can comprise one or more expandable membrane enclosures or balloon, sponge, attenuator, space occupying member, drug delivery device, data collection device, nerve stimulation device, wave producing device, vibration producing device, pressure sensing device, chemical sensing device, volume sensing device, or a therapeutic device. From this disclosure it will be appreciated that, although the examples provided deal primarily with intravesical applications, the methods and devices disclosed herein can be used to provide treatment at sites adjacent the bladder or between layers of bladder tissue. Further, the devices and methods herein can be used or applied within or proximal to other organs and sites in the body such as the heart, lung, cranium, cardiovascular system, breasts, abdominal area or cavity, eye, testicles, intestines, stomach, or other organs or tissues.

Some embodiments are directed to methods and apparatuses for measuring and/or attenuating and/or baffling transient pressure waves in relatively incompressible materials in organs of the body. Illustrative embodiments discussed herein relate generally to the fields of urology and gynecology, and in particular to the treatment of disorders of the urinary tract exacerbated by sudden fluctuations in intravesical pressure. However, the devices and methods are not limited to the fields of urology and gynecology and methods and apparatuses of embodiments disclosed herein can be used in other organs of the body, as well, to attenuate and/or baffle pressure transients or reversibly occupy intra- or inter-organ space.

Certain embodiments dampen transient intravesical pressure including pressure spikes experienced by the urinary tract. During a transient pressure event, the bladder becomes a relatively non-compliant environment due to a number of factors including the pelvic skeletal structure, the compressive loads of contracting tissues bounding the bladder, the decreased compliance of the musculature, or the incompressible behavior of urine, nerve, or connective tissue of the bladder. Factors contributing to the reduced compliance of the bladder are aging, anatomic abnormalities, or trauma to the structures of the pelvis and abdomen.

Figure 1:
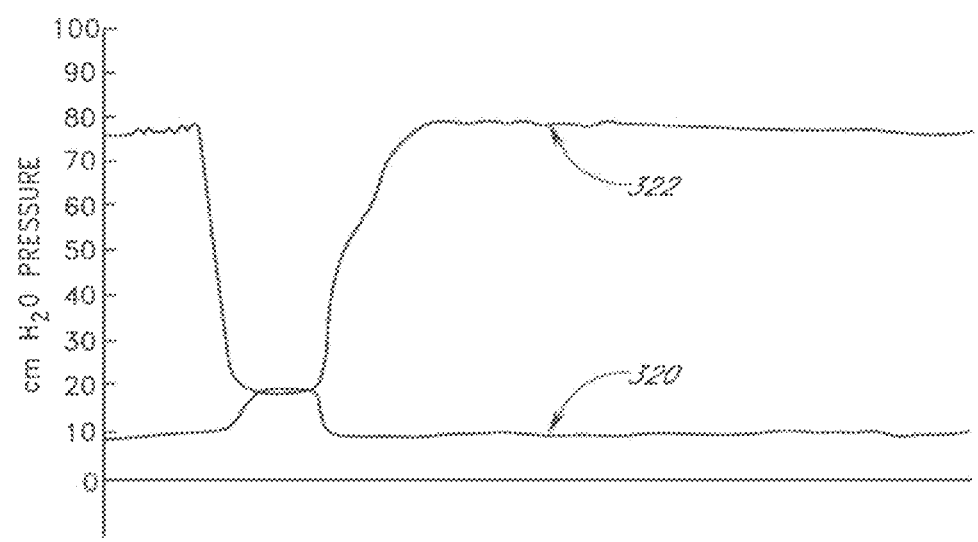
FIG. 1 illustrates maximum urethral pressure against intravesical pressure during normal voiding.

Urine is primarily composed of water and is virtually incompressible in the typical pressure ranges present within the human bladder. The relationship between the maximum urethral pressure and the intravesical pressure for normal voiding of the bladder is well defined. With reference to FIG. 1, relaxation of the urethra occurs before the detrusor muscle contracts to cause the intravesical pressure 320 to exceed the urethral pressure 322 during normal voiding. The pressures discussed herein are gauge or relative pressures except where absolute pressures and/or atmospheric pressures are specifically mentioned.

Figure 2:
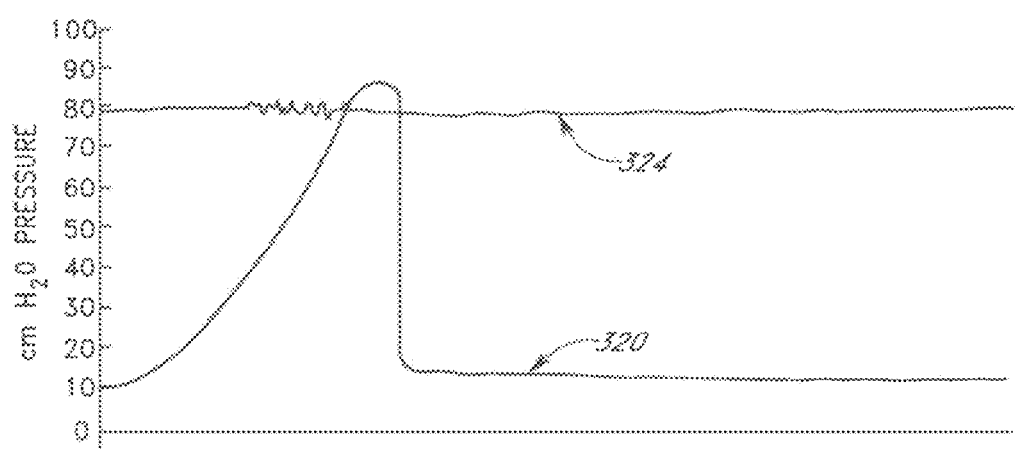
FIG. 2 illustrates the intravesical pressure exceeding the maximum urethral pressure in a noncompliant bladder.

The bladder serves two mechanical functions: 1) low-pressure storage and 2) high-pressure voiding. During the storage or filling phase, the bladder receives urine from the kidneys. Compliance of the bladder is defined as the ratio of the change in volume to the change in pressure, and the static compliance of the bladder is measured during a typical urodynamic evaluation. The static compliance index is measured by filling the bladder to cystometric capacity and allowing the pressures to equilibrate for a time period of approximately sixty seconds. The static compliance index is calculated by dividing the bladder capacity by the detrusor pressure at the end of filling. A normal bladder will typically exhibit static compliance between 15 and 30 ml/cm $H_2O$. A low static compliance bladder typically will have a compliance index of less than 10 ml/cm $H_2O$. With reference to FIG. 2 which illustrates different pressures for a non-compliant bladder, a low static compliance bladder typically is poorly distensible and has a high end-filling pressure. The intravesical pressure 320 increases to higher levels to exceed the maximum urethral pressure 324. The steady state or static compliance of the bladder is used to diagnose patients with neuropathic problems such as damage to the lower motor neurons, upper motor neurons, or multiple sclerosis. In addition, the steady state compliance of the bladder is also used, in some cases, to attempt to diagnose problems of incontinence, including urgency, frequency, and cystitis.

In general, intravesical pressure spikes result from volumetric tissue displacement in response to gravity, muscular activity, or rapid acceleration. The lack of compliance of the bladder and the urine contained in the bladder with respect to events of high frequency result in minimal fluidic pressure attenuation of the higher frequency pressure wave(s) and results in high intravesical pressures that are directly transmitted to the bladder neck and urethra, which may or may not cause detrusor contractions. Under these conditions, the urethra can act as a volumetric pressure relief mechanism allowing a proportional volume of fluid to escape the bladder, to lower the intravesical pressure to a tolerable level. The urethra has a maximum urethral pressure value, and when the intravesical pressure exceeds the maximum urethral pressure, fluid will escape the bladder. Under these conditions, nerve receptors in the bladder and/or bladder neck and/or trigone area trigger a detrusor contraction that can lead to micturition (frequency) or can subside without micturition (urgency) or can lead to the intravesical pressure exceeding the maximum urethral pressure resulting in fluid escaping the bladder (incontinence). Under these conditions, waves hitting and/or expanding the bladder wall can cause a patient with cystitis to exhibit significant pain.

Incontinence is common in males who have undergone radical prostatectomy, particularly where the sphincter has been compromised. In these patients, attenuation in the bladder reduces the intravesical peak pressures, resulting in less urine leakage. The attenuation requirements in these patients can include short duration pressure changes—such as, for example, 50 to 400 ms—and long duration pressure changes—such as, for example, greater than 500 ms—depending on the magnitude of damage to the urinary sphincter.

An aspect of certain embodiments of the present disclosure is the recognition that for the vast majority of patients suffering from problems of urinary tract disorders such as frequency, urgency, stress, and urge incontinence and cystitis, the cause and/or contributor to the bladder dysfunction is a reduction of overall dynamic bladder compliance rather than steady state bladder compliance. These patients can often have bladders that are compliant in steady state conditions, but have become non dynamically compliant when subjected to external pressure events having a short duration of, for example, less than 5 seconds or in some cases less than 2 seconds or even less than 0.01 seconds. Reduction in dynamic compliance of the bladder is often caused by some of the same conditions as reduction of steady state compliance including aging, use, distention, childbirth, and trauma. The anatomical structure of the bladder in relation to the diaphragm, viscera, and uterus (for women) causes external pressure to be exerted on the bladder during talking, walking, laughing, sitting, moving, turning, and rolling over.

Figure 3:
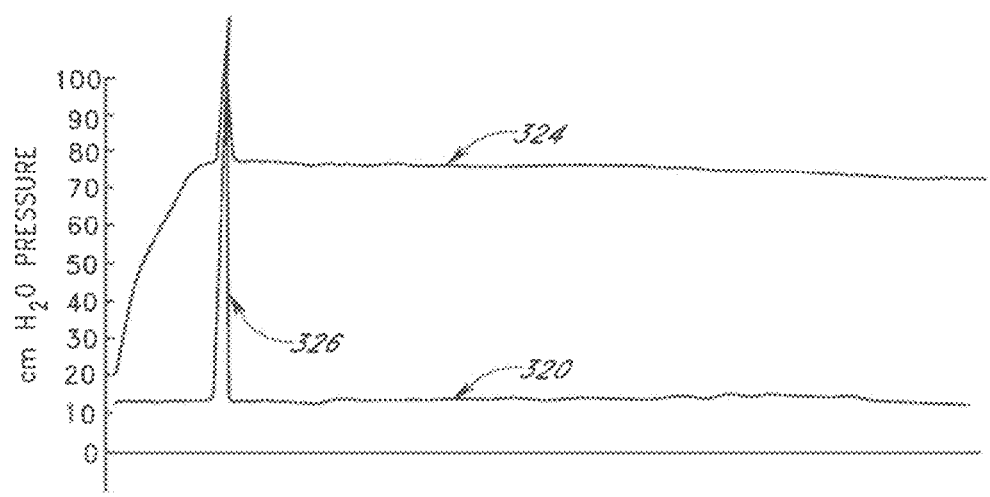
FIG. 3 illustrates an intravesical pressure spike exceeding the maximum urethral pressure during stress incontinence.

The relationship between intravesical pressure 320 and the maximum urethral pressure 324 for a patient suffering from stress incontinence due to lack of dynamic compliance in the bladder is illustrated in FIG. 3. When the patient coughs (or some other stress event occurs), a spike 326 will occur in the intravesical pressure. Intravesical pressure spikes in excess of 120 cm $H_2O$ have been urodynamically recorded during coughing, jumping, laughing, or sneezing. When the intravesical pressure exceeds the maximum urethral pressure value, leakage occurs. In order to retain urine during an intravesical pressure spike, the urinary retention resistance of the continent individual needs to exceed the pressure spike. Urinary retention resistance can be simplified as the sum total of the outflow resistance contributions of the urethra, bladder neck, and meatus. In female patients, it is generally believed that the largest resistance component is provided by the urethra. One measure of urinary resistance is the urodynamic measurement of urethral leak pressure. The incontinent individual typically has a urethral leak pressure less than 80 cm $H_2O$. The decline of adequate urinary retention resistance has been attributed to a number of factors including reduced blood flow in the pelvic area, decreased tissue elasticity, neurological disorders, deterioration of urethral muscle tone, and tissue trauma.

In practice, the urethral leak point pressure is determined by filling the bladder with a known amount of fluid and measuring the intravesical and abdominal pressures when there is a visible leak from the urethra while the patient is "bearing-down" (valsalva). With an attenuation device in the bladder, the measured intravesical leak point pressure typically increases due to the absorption of some the abdominal energy by the attenuation device. In this case, the patient has to push harder to achieve the same intravesical pressure. Since the abdominal muscles and muscles surrounding the urethra both contract simultaneously during a valsalva maneuver, the measured intravesical leak point pressure and urethral resistance increases when the attenuation device is in the bladder.

Figure 4A:
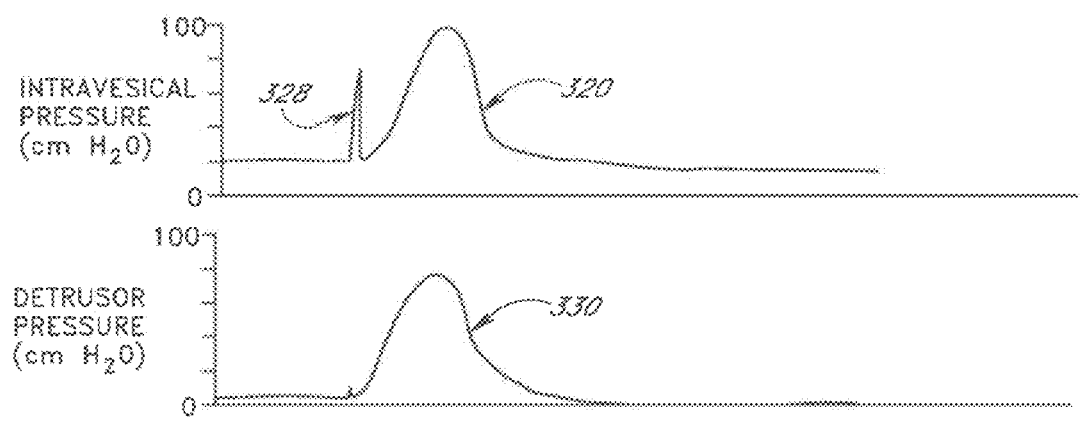
FIG. 4A illustrates the relationship between intravesical pressure and detrusor pressure during cough-induced urgency or frequency.
Figure 4B:
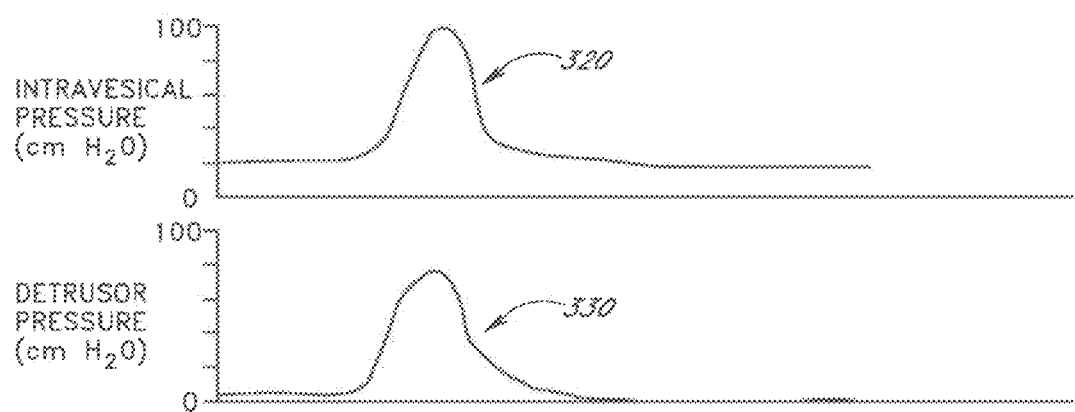
FIG. 4B illustrates the relationship between intravesical pressure and detrusor pressure during non-cough-induced urgency or frequency.

Urinary disorders, such as urgency, frequency, otherwise known as overactive bladder, and interstitial cystitis are caused or exacerbated when rapid pressure increases or rapid volume increases or other irritable conditions within the bladder cause motor neurons to send signals to the brain to begin the cascade of events necessary for urination. External pressure exerted on the bladder can result in a detrusor contraction that can result in urgency, frequency, or incontinence. See FIG. 4A (cough-induced urgency/frequency) and 4B (non-cough-induced urgency/frequency). With reference to FIG. 4A, a coughing event 328 induces increased intravesical pressure 320 which results in increased detrusor pressure 330. An increase in the detrusor pressure 330 generally is associated with increased urgency, frequency, or incontinence. Urinary disorders such as interstitial cystitis or irritable bladder conditions are a chronic inflammatory condition of the bladder wall, which includes symptoms of urgency and/or frequency in addition to pain. Therefore, the problem of a pressure spike in the functionally noncompliant bladder can be further exacerbated by a nearly simultaneous contraction of the bladder and a relaxation of the urethra.

Some embodiments provide methods and devices for treating and/or compensating for reduced dynamic compliance of the bladder. In some embodiments, an attenuation device having a compressible element is placed within the human urinary bladder in a manner that allows the compressible element to act as a pressure attenuator to attenuate transient pressure events. The term attenuator or pressure attenuation device can refer generally to devices that attenuate pressure, force, or energy by dissipating or dampening the pressure, force, or energy. Gases, such as atmospheric air, carbon dioxide, nitrogen, and certain perfluorocarbons (PFC) are very compressible in the pressure ranges typically encountered in the human bladder, and can be used in attenuation devices inserted in the bladder. Furthermore, when compared to the tissues encompassing urine, gases are significantly more compliant than the immediate environment. The addition of a volume of gas acts as a low rate spring in series with the native fluidic circuit of the urinary tract.

In accordance with some embodiments, a pressure attenuation device is placed within the human urinary bladder. The attenuation device can be a pressurized container. The container can take many forms including a sphere. The pressure attenuation device can be untethered in the bladder and can remain in the bladder for between several hours and one year, between one week and six months, or between one day and three months. In certain embodiments, the pressure attenuation device can include a balloon with a relaxed (unstretched or natural) volume of between 1 and 500 cc, more preferably between 10 and 180 cc, and, more preferably still, between 25 and 60 cc, and, more preferably still, between 25 and 29 cc. In certain embodiments, two or more discreet pressure attenuation devices are used. In such embodiments, the sum of the volumes of the pressure attenuation devices can equal the desired uncompressed displacement.

The pressure attenuation device can be a unitary component but can, in certain embodiments, be comprised of two or more subcomponents. The pressure attenuation device can be made with or without a seam. The pressure attenuation device can comprise a balloon having an average wall thickness between 0.0003 and 0.005 inches in certain embodiments, or between 0.0008 and 0.0025 inches in certain embodiments or between 0.002 and 0.0035 inches in certain embodiments, and between 0.001 and 0.00175 inches in certain embodiments. In some embodiments, the minimum wall thickness of the outer wall of the balloon is between 0008 and 0.00325 inches in certain embodiments, between 0.002 and 0.0035 inches in certain embodiments, and between 0.001 and 0.00175 inches in certain embodiments. In some embodiments, the minimum wall thickness location of the balloon is at the equator of the balloon. In some embodiments, the equator of a balloon is the widest diameter of the balloon along an axis that is perpendicular to the longitudinal axis of the balloon. In some embodiments, the equator of a balloon is the widest diameter along an axis that is perpendicular to the transverse axis of the balloon. In other embodiments, the balloon wall thickness could be varied from these ranges. In some embodiments described herein, pressure attenuation device is free-floating in the bladder as has been described. In other embodiments, the pressure attenuation devices could be surgically affixed to the bladder wall through the use of suture, staples and other accepted methods, or placed submucosally or intramuscularly within the bladder wall. Other embodiments could also include pressure attenuation devices with programmable, variable, and adjustable buoyancy by using ballasting, specific inflation/deflation solutions, alternative materials of construction, or by other means.

Pressure Attenuation Device

A pressure attenuation device (also referred to herein as "device") comprising a balloon can be placed within a body, such as the bladder. The balloon can form a compressible element that can act as a pressure attenuator to attenuate transient pressure events. In certain embodiments, gases, such as atmospheric air, carbon dioxide, nitrogen, and certain perfluorocarbons (PFC), can be used to inflate the pressure attenuation device and can act as a low or variable rate spring in series with the native fluidic circuit of the urinary tract. The pressure attenuation device can take many forms including a sphere, some examples of which are outlined herein.

In some embodiments, the balloon of the pressure attenuation device can include outer wall that defines a interior chamber within the outer wall. The device can also include a valve that can allow for the addition or removal of substances from within the balloon. In some embodiments, an pressure attenuation device for use in a body comprises a balloon having an outer wall defining an interior chamber therein. The balloon can be defined by a number of parameters, including, but not limited to, a natural volume, a maximum volume, wall material, wall stiffness, and wall thickness. Certain embodiments of constructing the balloon and pressure attenuation device will be described below FIGS. 5A-10B along with certain structural aspects of the balloon and pressure attenuation device, which can be utilized in the embodiments described herein.

Additional embodiments of an implantable pressure attenuation device are described in U.S. Pat. No. 6,682,473, incorporated by reference herein. See for example, FIGS. 5, 5A, 7A-C, 8A-E, 13-25, and 27-31, and the accompanying discussion, including at columns 9-12, 13-14, 17-20, and 21-24. See also the disclosure from U.S. Pat. No. 6,976,950, incorporated by reference herein, as well as, FIGS. 32A-33C, 36-38, 47A-C, 49 and the accompanying discussion, including at columns 15-18, 30-35, and 39-40.

U.S. Patent Application Publication No. 2010/0222802 (now U.S. Pat. No. 8,574,146) incorporated by reference herein discloses still additional embodiments of implantable pressure attenuation devices. See for example, FIGS. 5-5N, 8A-8B, 10A, 11C, 34A-35D, 37A-37B, 38A-51C, and the accompanying discussion, including paragraphs [0127]-[0152], [0167]-[0168], [0174], [0177], [0233]-[0242], [0354]-[0438], and [0466]-[0475].

Figure 5A:
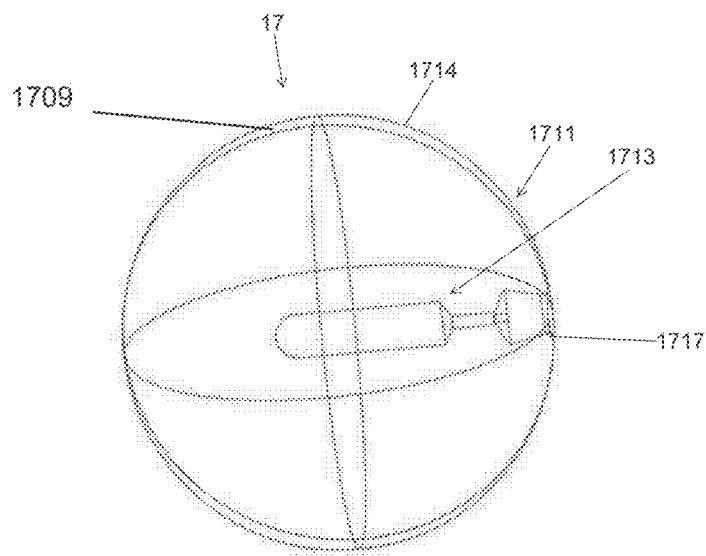
FIGS. 5A through 5C are perspective views of a pressure attenuation device in an inflated state, the fluids within the inflated device not being shown.
Figure 5B:
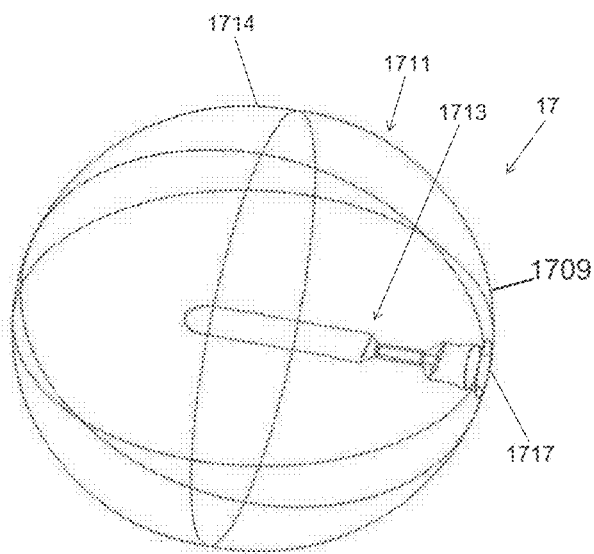
Figure 5C:
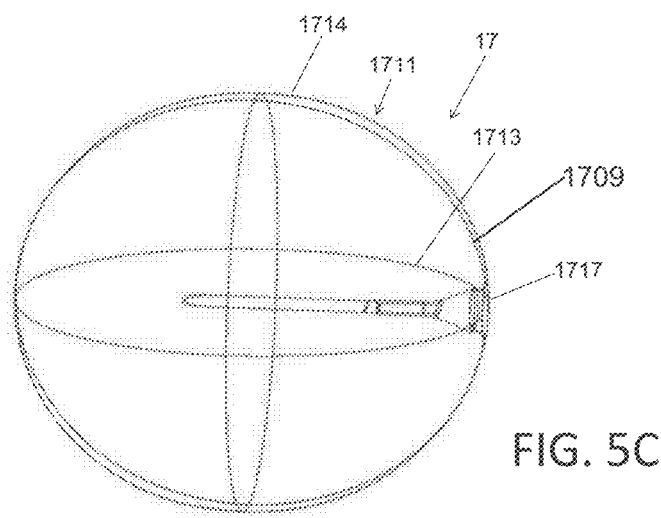

Referring now to FIGS. 5(A) through 6, various embodiments of a pressure attenuation device 17 (also referred to herein as "device 17" or "device") will now be described. As shown in these figures, in the illustrated embodiment, the device 17 can comprise a balloon 1711 and a valve 1713. The valve 1713 can serve to regulate the flow of fluid into and out of the balloon 1711. The balloon 1711 can comprise an outer wall 1709 that can define an interior chamber 1707 (see FIG. 6).

The balloon 1711 can be made of flexible material such as an elastomeric material. In some embodiments, the balloon 1711 e.g., the outer wall 1709 (all or most of the outer wall 1709) of the pressure-attenuating device 17 can be constructed out of flexible material such as an elastomeric material. Such elastomeric materials for the balloon 1711 and the outer wall 1709 include, but are not limited to, polyurethane, polyester, polyamide, polyester copolymer, polyamide copolymer, polyethylene, polypropylene, polystyrene/polybutadiene copolymer, thermoplastic polyurethanes, and combinations thereof.

Examples of polyesters include polyethylene terephthalate (PET) polymers and polybutylene terephthalate (PBT) polymers. Examples of commercially available PET polymers include the Selar PT family of PET polymers (e.g., Selar PT8307, Selar PT4274, Selar PTX280), which are commercially available from E. I. DuPont de Nemours (Wilmington, Del.), the Cleartuf family of PET polymers (e.g., Cleartuf 8006), which are commercially available from M&G Polymers (Apple Grove, W. Va.), the Traytuf family of PET polymers (e.g., Traytuf 1006), which are commercially available from the Shell Chemical Company (Houston, Tex.), and the Melinar family of PET polymers (e.g., Melinar 5922C), which are commercially available from E. I. DuPont de Nemours (Wilmington, Del.).

Examples of commercially available PBT polymers include the Celanex family of polymers, commercially available from Ticona (Summit, N.J.), the Riteflex family of polymers, commercially available from Ticona (Summit, N.J.), the Hytrel family of PBT copolymers (e.g., Hytrel 5556, Hytrel 7246, Hytrel 4056), commercially available from E. I. DuPont de Nemours (Wilmington, Del.), and the Arnitel family of PBT copolymers (e.g., Arnitel EM630), commercially available from DSM (Erionspilla, Ind.).

Examples of polyamides include the nylon family of polymers, such as, for example, aliphatic nylons and aromatic nylons. Examples of aliphatic nylons include nylon 12, nylon 6, nylon 6/10, nylon 6/12 and nylon 11. Nylon 12 is commercially available from, for example, Atofina (Philadelphia, Pa.). Nylon 12 is also commercially available as the Grilamid family of polymers from EMS (Sumter, S.C.) and as the Vestamid family of polymers from Daicel-Degussa Ltd. Nylon 6 is commercially available from, for example, HoneyWell (Morristown, N.J. Nylon 6/10 is commercially available from, for example, BASF (Mount Olive, N.J.). Nylon 6/12 is commercially available from, for example, Ashley Polymers (Cranford, N.J.). Nylon 11 is commercially available from EMS (Sumter, S.C.).

Examples of aromatic nylons include the Grivory family of polymers (commercially available from EMS (Sumter, S.C.)), nylon MXD-6 polymers (commercially available from Mitsubishi Gas Chemical (Tokyo, Japan)), and the Trogamid family of polymers (commercially available from Degussa AG (Germany).

Additional examples of polyamides include polyether block polyamide copolymers (commercially available, for example, as the Pebax family of polymers (e.g., Pebax 2533, Pebax 3533, Pebax 4033, Pebax, 5533, Pebax 6033, Pebax 7033, Pebax 7233) from Atofina (Philadelphia, Pa.)).

When inflated, the balloon 1711 can comprise a generally spherical bulb portion 1714 and an inverted tubular tail portion 1717 extending into bulb portion 1714, tail portion 1717 terminating in an opening 1719 (FIG. 6). The balloon can contain an inflation media also referred to herein as a pressure media. The inflation media 1705 can contain a high vapor pressure media such that the balloon can contain the high vapor pressure media 1705. In some embodiments, the balloon can be inflated with other gases in addition to the high vapor pressure media. In such embodiments, the inflation media can contain other gasses in addition to the high vapor pressure media such as air, nitrogen, oxygen, argon, hydrogen, oxygen, helium, carbon dioxide, neon, krypton, xenon, radon, and etc. In the illustrated embodiment, an area of increased wall thickness or retaining feature 1715 can be disposed on bulb portion 1714 opposite to tail portion 1717. The retaining feature 1715 can be a portion of the pressure attenuation device 17 that is used to retain the pressure attenuation device 17 into the window of a delivery system. The retaining feature 1715 can be an area of the balloon 1711 that is the same or higher wall thickness than adjacent areas of the balloon 1711, or a member that is more rigid than the balloon 1711, which can be integral to or adhered to the balloon 1711, as an example. In the certain embodiments, balloon 1711 can be made of a sufficiently transparent material to permit the contents housed by the balloon 1711 to be seen.

The balloon 1711 can be seamless and can be substantially arcuate, with the only exception being tail portion 1717, which is inverted and to which the valve 1713 can be welded or otherwise attached. To minimize the potential for encrustation, to maximize patient tolerability, or for other reasons, it is preferable that over 95% of the external surface area of balloon 1711 be continuously arcuate and that less than 5% of the surface area of the balloon the balloon 1711 not be arcuate. More preferably, over 97% of the external surface area of the balloon 1711 is continuously arcuate and less than 3% of the external surface area is not arcuate. Even more preferably, over 99% of the external surface area of the balloon 1711 is continuously arcuate and less than 1% of the surface area is not arcuate.

For example, some embodiments of the balloon 1711 can have an overall surface area of 4,586 mm$^2$. The external surface area of the continuously arcuate portion of the balloon 1711 can be 4,575 mm$^2$. The ratio of continuously arcuate surface area to non-arcuate surface area for this embodiment is 401:1. This ratio is preferably from 100:1 to 1500:1 and more preferably from 400:1 to 600:1. The diameter of the tail portion 1717 can be 0.15 inch, and the diameter of bulb portion 1714 is 1.58 inches. The ratio of the diameter of the bulb portion 1714 to the diameter of tail portion 1717 is 10.53:1. This ratio is preferably between 6:1 and 20:1 and more preferably greater than 8:1. Without limitation to any particularly theory or embodiment, it is believed that such a ratio can serve to keep tail portion 1717 inverted within bulb portion 1714.

The valve 1713, which is also shown in FIG. 7, can be formed from a pair of matching, appropriately shaped, flat sheets of elastomeric material. In certain embodiments, valve can be formed in a different manner or from a different component. In illustrated embodiment, the pair of matching flat sheets can be heat-sealed to one another along their respective sides to form a pair of seams 1720-1 and 1720-2 and can also be molded so as to define a proximal section 1721, an intermediate section 1723, and a distal section 1725. Proximal section 1721 can be generally flat or generally frusto-conical in shape and can include outer surfaces 1721-1 and 1721-2 that can be fixedly mounted within opening 1719 of the balloon 1711 (FIG. 6) by a flat weld (where proximal section 1721 is flat) or by a circumferential weld (where proximal section 1721 is frusto-conical.) The proximal section 1721 can include an end surface 1722, which can be a surface or mating surface, intended to interface the distal end 1527 of push-off member, thereby allowing push-off member to push the device 17 off a distal end of an inflation tube. In some embodiments, this surface 1722 is a 90 degree flat surface. Other surfaces, such as a concave or convex surface may also interact with the distal end of push-off member. The shape of the distal end of the pushoff member can be flat, concave, convex, or a shape that permits interaction with the end surface 1722. Intermediate section 1723 can be generally cylindrical and can be reduced in inner diameter and in outer diameter as compared to proximal section 1721. Moreover, intermediate section 1723 can be reduced in inner diameter as compared to the outer diameter of an inflation tube and can include an inner side surface 1724 that can be used to make a stretch interference fit with the inflation tube so as to seal against the inflation tube or to prop open valve 1713, which will close upon release, thereby enabling the balloon 1711 to be inflated under high pressure with minimal leaking. For example, where the outer diameter of the inflation tube can be in the range of about 0.001-5.00 inch, preferably about 0.005-0.50 inch, more preferably about 0.010-0.125 inch, the inner diameter of intermediate section 1723 can be correspondingly smaller, for example, in the range of about 0.0005-4.900 inch, preferably about 0.001-0.49 inch, more preferably about 0.005-0.120 inch. Moreover, the wall thickness of intermediate section 1723 can be in the range of about 0.0001-2.00 inch, preferably about 0.001-0.24 inch, more preferably about 0.005-0.050 inch. In certain applications, the nominal pressure exerted on the self-sealing valve 1725 is relatively low, e.g., below 3 psi. Therefore the surface area of the contact area of the two surfaces must be sufficient to resist flow during use. This is can be accomplished with a structure 1725 that has a width typically less than 1 inch, more preferably less than 0.5 inches, and more preferably less than 0.25 inches. To maintain valve function, the length of the structure 1725 can be greater than the width of structure 1725, more preferably the length is greater than 1.5 times the width of the structure 1725, and more preferably greater than two times the width of the structure 1725. Distal section 1725 can be a generally elongated, flattened structure that is self-sealing (i.e., biased, independently of its environment, towards a closed state) and that has a distal end 1727 through which fluid inputted to valve 1713, in the manner discussed herein, can exit valve 1713 to occupy the space defined by the balloon 1711. Preferably, distal section 1725 is made sufficiently long to minimize the escape of fluid from within the balloon 1711 through valve 1713.

Figure 8:
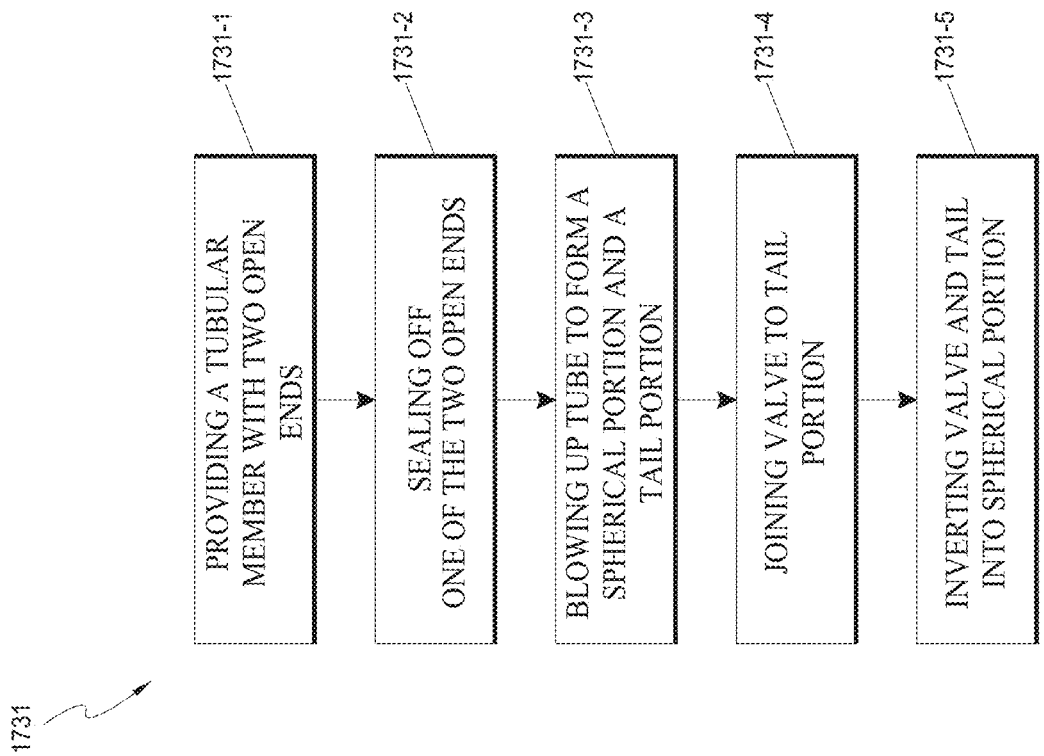
FIG. 8 is a flowchart, schematically illustrating one method of manufacturing the pressure attenuation device of FIGS. 5A through 5C.
Figure 9A:
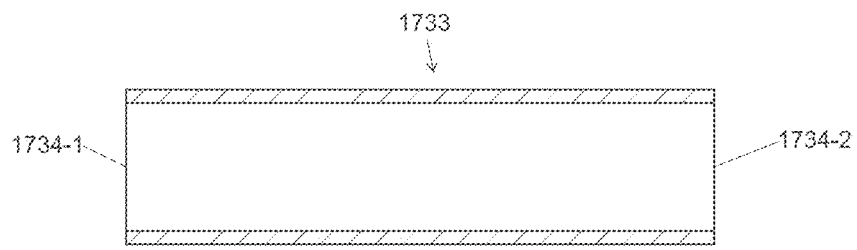
FIGS. 9A through 9D are section views, illustrating parts of certain steps of the method shown in FIG. 8.
Figure 9B:
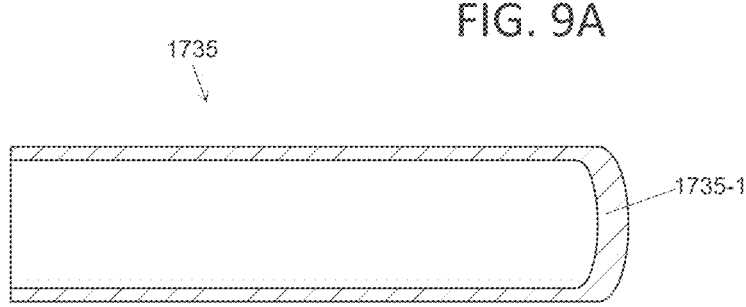
Figure 9C:
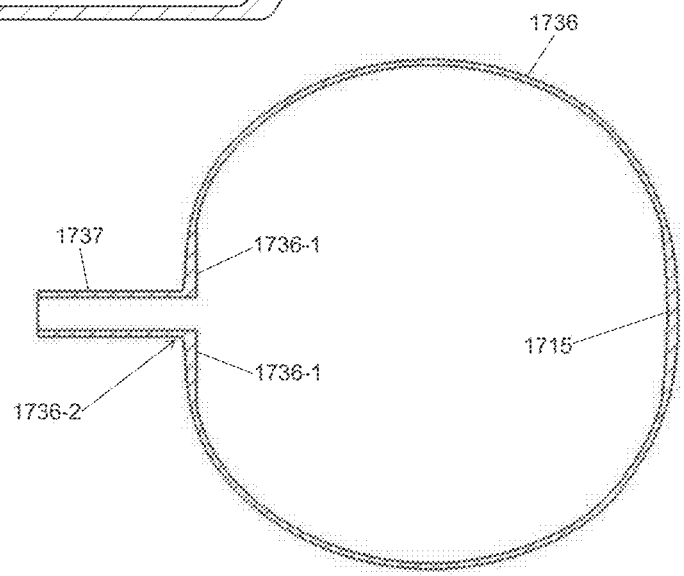
Figure 9D:
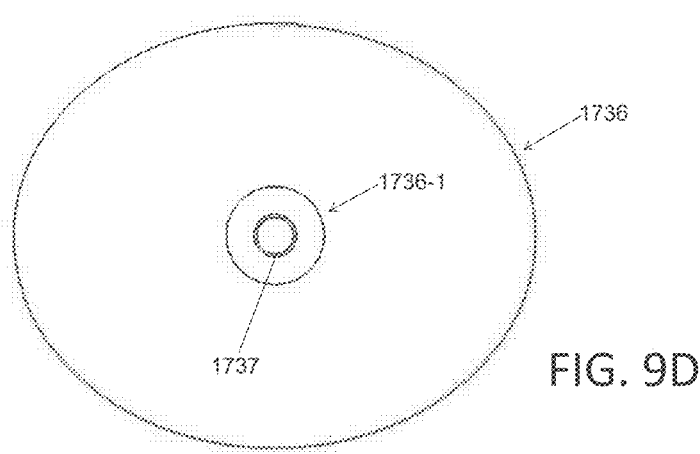

Referring now to FIG. 8, there is shown a flowchart, schematically depicting one possible method 1731 for making the device 17. Method 1731 can begin with a step 1731-1 of providing a tubular member, which can be, for example, an extruded tube 1733 of elastomeric material having a pair of open ends 1734-1 and 1734-2 (see FIG. 9A). Method 1731 can continue with a step 1731-2 of closing off end 1734-2 to form a tube 1735 having a closed end 1735-1 (see FIG. 9B). Method 1731 can then continue with a step 1731-3 of blowing up or expanding tube 1735 to form a generally spherical portion 1736 and a generally cylindrical tail portion 1737 (see FIG. 9C). (Step 1731-3 can further include pulling on the closed end 1735-1 during said expansion of tube 1735.) Method 1731 can then continue with a step 1731-4 of inserting valve 1713 into tail portion 1737 and joining, such as by either a circumferential weld or a flat weld, proximal section 1721 to tail portion 1737. Method 1731 can then conclude with a step 1731-5 of inverting the combination of valve 1713 and tail portion 1737 into generally spherical portion 1736, thereby forming the device 17. In some embodiments, to prevent the valve 1713 and tail portion 1737 from reversing this inverting step 1731-5 during use, the valve and tail portion can be anchored to the balloon wall in any method known in the art including but not limited to use of an adhesive or welding the distal end of the valve to the balloon wall, for example. An embodiment is to fabricate the balloon to provide increased resistance to the reversal of inverting step 1731-5 with one or more of the following features: 1) an increase in wall thickness or stiffness on the balloon near the area of the balloon where the tail protrudes (for example, a circumferential increase in balloon thickness 1736-1 that measures more than two times the diameter of the tail, and more preferably more than 1.5 times the diameter of the tail, and more preferably more than 1 time the diameter of the tail, and this circumferential wall thickness is less than 0.075 inches, and more preferably less than 0.050 inches, and more preferably less than 0.025 inches; 2) a wall thickness of the tail 1737 that is at least 1 time the wall thickness of the balloon 1736, more preferably at least 1.5 times the wall thickness of the balloon 1736, more preferably at least two times the wall thickness of the balloon 1736, more preferably at least three times the wall thickness of the balloon 1763; 3) a balloon with a measured angle between the wall of the balloon near the tail opening and the tail 1736-2 of at least 45 degrees, more preferable greater than 70 degrees, more preferable greater than 80 degrees, and more preferable approaching 90 degrees; and 4) a measured radius where the tail 1737 interfaces with balloon 1736 of less than 0.5 inches, more preferably less than 0.1 inches, more preferably less than 0.075 inches, more preferably less than 0.035, and preferably 0.015 inches. Preferably, device 17 is dimensioned so that spherical portion 1736, when expanded, has a diameter that is approximately 6-20 times the diameter of the entry port defined by the interface of spherical portion 1736 and inverted tail portion 1737. In some embodiments, the shape, thickness and material of closed end 1735-1 forms the integral retaining member 1715 in the wall of the balloon. In some embodiments, the valve is not inverted and only the tail is inverted such that the tail is inverted and both the tail and valve are moved into the spherical portion.

The balloon 1711 can alternatively be made using a dip process. For example, Brash et al., "Development of block copolyether-urethane intra-aortic balloons and other medical devices," *Journal of Biomedical Research*, 7(4):313-34 (1973), which is incorporated herein by reference, describe a manufacturing process that can be used to manufacture the balloon 1711. A mandrel is formed from expendable wax, and then dipped using commonly known balloon dipping methods to form a balloon. Upon cure of the balloon material, the wax is melted and removed, resulting in the desired balloon.

One advantageous feature of device 17 is that it can be devoid of seams on its exterior surface. The absence of such seams can be desirable since such seams can rub up against and cause irritation with the bladder or other anatomical structure in which device 17 is positioned. In addition, such seams can become encrusted, over time, with biological sediment from the anatomical structure in which device 17 is positioned, which encrustation can exacerbate irritation or can otherwise be regarded as unhygienic or undesirable.

Embodiments of balloon have been described as having certain properties and characteristics as described in relation to specific test procedures. In some embodiments, the balloon can be substantially homogeneous such that the entirety of the balloon exhibits the properties. For example the balloon wall thickness can be substantially homogenous over the surface of the balloon. In some embodiments, the balloon wall thickness varies throughout balloon. In some embodiments, a portion of the inflatable the balloon that is less than the entirety of the balloon can exhibit the properties. For example a portion of the inflatable the balloon wall could exhibit the characteristics described.

As discussed herein, in some embodiments, the balloon/ can have a substantially uniform wall thickness. In some embodiments, the average wall thickness of the outer wall of the balloon is between 0.0003 and 0.005 inches, or between 0.0008 and 0.0025 inches and in certain embodiments between 0.002 and 0.0035 inches, and certain embodiments between 0.001 and 0.00175 inches. In some embodiments, the minimum wall thickness of the balloon is between 0.0008 and 0.00325 inches, and in certain embodiments between 0.002 and 0.0035 inches, and certain embodiments between 0.001 and 0.00175 inches. In some embodiments, the thinnest location of the balloon also referred to as the location of minimum wall thickness is at an equator of the balloon. In some embodiments, the balloon wall thickness varies based on materials and manufacturing processes. In some embodiments, the balloon wall thickness is not homogenous and can be varied. In some embodiments, the wall thickness can be varied dependent upon geometric configurations of the balloon. In some geometric configurations the balloon can be configured so that different portions of the balloon have different thicknesses and exhibit different properties based on how the balloon is configured to be placed within the patient. In some embodiments, the minimum wall thickness also referred to herein as the thinnest thickness of the inflatable balloon 1711 is measured from the thinnest portion of the balloon, which in some examples is at the equator of the balloon. In some embodiments, the equator of a balloon is the widest diameter of the balloon along an axis that is perpendicular to the longitudinal axis of the balloon. In some embodiments, the equator of a balloon is the widest diameter along an axis that is perpendicular to the transverse axis of the balloon. One can measure the thickness of the balloon by measuring the outer wall. One can measure the thickness of the balloon by pinching a deflated balloon and measuring two walls (double wall thickness) of the balloon together and dividing the value by two. In some embodiments, the average thickness of the inflatable balloon 1711 is an average of thickness from various regions of the inflatable the balloon, such as at the equator, regions near the poles, and etc. In some embodiments, the double wall thickness is used as a measurement for thickness of the inflatable the balloon. In some embodiments, the wall thickness at the equator of the balloon is the thinnest portion having the minimum wall thickness and can determine the stress and strain of the inflatable the balloon 1711.

Figure 10A:
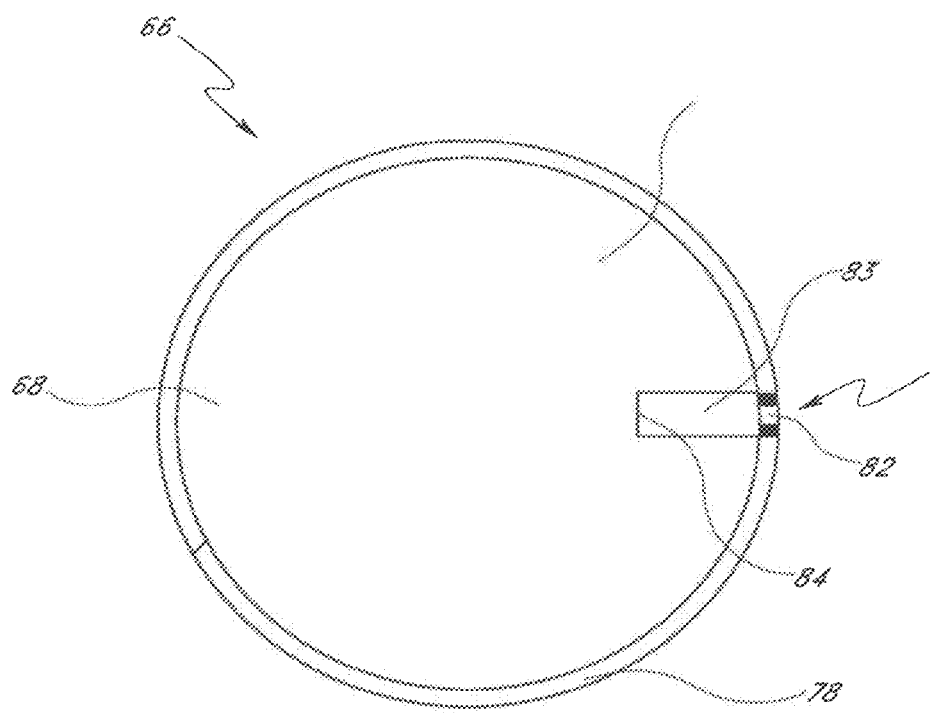
FIG. 10A is a schematic top plan view of a pressure attenuation device.
Figure 10B:
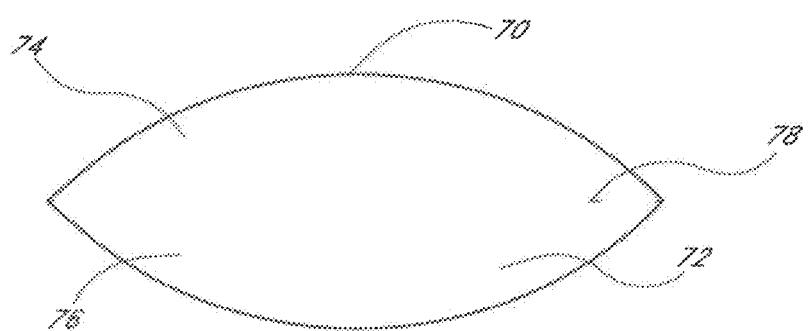
FIG. 10B is a side elevational view of FIG. 10A.

Referring to FIGS. 10A and 10B, additional embodiments of a pressure attenuation device 66 are illustrated in which the device 66 constructed in a different manner. In the illustrated embodiment of FIGS. 10A and 10B, the inflatable balloon 68 is illustrated as having a generally circular profile, although other profiles can be used.

The balloon 68 illustrated in FIGS. 10A and 10B comprises an outer wall 70, for separating the contents of the device 66 from the external environment. Outer wall 70 can comprise a first component 74 and second component 76 bonded together such as by a seam 78. In the illustrated embodiment, the first component 74 and second component 76 are essentially identical, such that the seam 78 is formed on the outer periphery of the balloon 68. Seam 78 can be accomplished in any of a variety of manners known in the medical device bonding arts, such as heat bonding, adhesive bonding, solvent bonding, RF or laser welding, or others known in the art.

The outer wall 70, formed by a bonded first component 74 and second component 76, defines an interior cavity or interior chamber 72. As is discussed elsewhere herein, interior chamber 72 preferably comprises a media that can include a compressible component, such as gas, or foam. Other media or structures capable of reduction in volume through a mechanism other than strict compression can also be used. For example, a material capable of undergoing a phase change from a first, higher volume phase to a second, lower volume phase under the temperature and pressure ranges experienced in the bladder can also be used. In some embodiments, the media comprises a liquid that forms a solid or foam after implantation. In some embodiments, the media comprises a solid.

To facilitate filling the interior chamber 72 following placement of the device 66 within the bladder, the balloon 68 is preferably provided with a valve 80. In the illustrated embodiment, the valve 80 is positioned across the seam 78, and can be held in place by the same bonding techniques used to form the seam 78. The valve 80 can be omitted in an embodiment in which the attenuation device 66 is self-expandable.

The valve 80 generally comprises an aperture 82, for receiving a filling tube therethrough. The aperture 82 is in fluid communication with the interior chamber 72 by way of a flow path 83. At least one closure member 84 is provided for permitting one way flow through flow path 83. In this manner, a delivery system and filling device can be used to displace closure member 84 and introduce compressible media into the interior chamber 72. Upon removal of the filling device, the closure member 84 prevents or inhibits the escape of compressible media from the interior chamber 72 through the flow path 83.

Thus, the closure member 84 is preferably movable between a first orientation in which it obstructs effluent flow through the flow path 83 and a second position in which it permits influent flow through the flow path 83. Preferably, the closure member 84 is biased in the first direction. Thus, forward flow can be accomplished by either mechanically moving the closure member 84 into the second position such as using a filling tube, or by moving the closure member 84 into the second position by exerting a sufficient pressure on the compressible media in flow path 83 to overcome the closure bias. Any of a wide variety of valve designs, including those discussed elsewhere herein, can be used in the device 66 or device 17 described above.

In order to minimize trauma during delivery of embodiments of the device 17, 66 described herein, the device 17, 66 is advantageously expandable from a first, reduced cross-sectional configuration to a second, enlarged cross-sectional configuration. The device 17, 66 can thus be transurethrally deployed into the bladder in its first configuration, and enlarged to its second configuration once positioned within the bladder to accomplish a pressure attenuation function. Preferably, a crossing profile, or a greatest cross-sectional configuration, of the attenuation device 17, 66 when in the first configuration is no greater than about 30 French in certain embodiments, 24 French (8 mm) in certain embodiments, and, no greater than about 30 French in certain embodiments, no greater than about 24 French in certain embodiments, no greater than about 18 French (6 mm) in certain embodiments, and in certain embodiments no greater than about 14 French. This can be accomplished, for example, by rolling a deflated balloon about a longitudinal axis, while the interior chamber is evacuated. Once positioned within the bladder, the interior chamber 72 can be filled with an inflation media, such as a high vapor pressure media or such as a high vapor pressure media in combination with other gases, to produce a pressure attenuation device 17, 66.

Various coatings can be used to enhance the biocompatibility of the implantable devices 17, 66 and associated insertion or removal devices described herein. Lubricating coatings, substances, and substrates can be used to facilitate insertion or removal. In some embodiments, the device incorporates biocompatible coatings or fillers to minimize irritation to the bladder wall and mucosa and/or to inhibit the formation of mineral deposits (encrustation) or biofilm formation. Such device treatments can also inhibit films, deposits or growths within or on the surface of the device. Materials can be coated onto the surface or incorporated within the wall of the device. Biocompatible lubricating substances can be used to facilitate the placement of the attenuation device/fill tube within a lumen of an introducer.

As shown in FIGS. 13A-C, the human urinary bladder 5 is a solid, muscular, and distensible organ that sits on the pelvic floor. It collects urine excreted by the kidneys prior to disposal by urination. Urine enters the bladder 5 via the ureters (not shown) and exits via the urethra 7.

The walls of the bladder 5 are mostly comprised of muscle tissue. This muscle tissue is known as the detrusor muscle, and is a layer of the urinary bladder wall made of smooth muscle fibers arranged in spiral, longitudinal, and circular bundles. When the bladder 5 is stretched, nerves are activated which signals to the parasympathetic nervous system to contract the detrusor muscle. This encourages the bladder 5 to expel urine through the urethra 7. For the urine 104 to exit the bladder, both the internal sphincter and the external sphincter need to open. The urinary bladder 5 can contain a wide range of urine volumes, from 0 to as much as about 600 ml of urine. Typically, in a female, bladder urine volumes range from 0 to about 300 ml. Typically, in a female, a full bladder will contain about 250 to 300 ml.

The neck of the bladder is the area immediately surrounding the urethral opening; it is the lowest and most fixed part of the organ. In the male it is firmly attached to the base of the prostate, a gland that encircles the urethra. The bladder neck is commonly more or less funnel-like in shape. The angle of inclination of the sides of this funnel varies based on the degree to which the bladder is full, and also varies during filling and emptying of the bladder. A very full distended bladder will have a bladder neck with more oblique walls, and a bladder that is emptying or empty will be more acute. The posterior portion of the bladder neck that is contiguous with the base of the bladder has a region containing a high density of sensory nerves. This region is triangular in shape and is known as the trigone region. This inverted triangle defined by the urethra (the vertex of the triangle) and the ureteral orifices at each corner of the base of the triangle. The ureteral orifices are the locations where the ureters enter the bladder.

The highest concentration of sensory nerve receptors in the bladder can be found in the trigone region. Anything that causes pressure, friction, or irritation on this region can cause a number of morbidities, including urgency, frequency, pain and/or irritation. The bladder neck contains stretch receptors, and anything that lodges in or otherwise stretches the bladder neck will likewise be very uncomfortable. When designing a device that is to reside in whole or in part in the bladder, the comfort of that device will be significantly impacted by the device's ability to minimize or avoid contact with these two particularly sensitive areas.

In addition, the bladder does not contract or expand uniformly. For example, when the bladder is full it is quasi-spheroid or ovoid in shape. Its muscular walls are stretched out. During micturition, as the bladder empties, the superior and inferolateral walls contract. Wrinkles, or rugae, form in these walls as they shrink. The bladder neck and trigone area is more firmly anchored to underlying tissue and does not shrink as significantly or form rugae. Consequently the shrinkage of the bladder is not uniform and most of the reduction in size comes from the shrinkage of the superiolateral and inferolateral walls, and from the superior wall, or dome, becoming convex as it collapses towards the trigone and bladder neck area.

Accordingly, intravesical implants can preferably be configured to avoid, or not be capable of entering the bladder neck and trigone area. This can reduce or eliminate irritation to these sensitive areas containing the majority of the pain receptors in the bladder. Also, recognizing the non-uniform contraction of the bladder as it empties, other embodiments can include devices that reside in the folded perimeter of the bladder and/or comprise an open center (such as a toroid) or perforated center (i.e., a central region that permits flow through) that does not contact the sensitive trigone area, and optionally can remain in a relatively fixed location.

If the implant gets too large, then it can diminish the urine storage capacity of the bladder to the point where the patient may need to urinate more frequently. Accordingly, one or more embodiments of devices are adapted to not occupy more than 10% of a typical functional capacity of the bladder. In other embodiments, the volume of the implant can be as high as 20%-50% of functional capacity. In other embodiments, the volume of the implant can be as high as 50%-over 100% of functional capacity.

In certain embodiments, the pressure attenuation devices provided herein can be suitable for providing a platform for an intravesical device comprising a drug delivery device, data collection device, attenuation device, nerve stimulation device, wave producing device, vibration producing device, pressure sensing device, chemical sensing device, volume sensing device, pH sensing device, or a therapeutic device. Such functions may be in addition to or as an alternative to the pressure attenuation functions described herein.

As discussed previously, the pressure attenuation device 17, 66 can be at least partially expandable. Expansion facilitates delivery by allowing the device 17, 66 to assume a first delivery profile for passage through the urethra or surgical opening in the bladder and to assume a second expanded profile operable to prevent the implant from entering the trigone region. In some embodiments, the expanded device 17, 66 can be characterized by one or more dimensions greater than the smallest cross-section distance of the trigone region. FIG. 13B schematically illustrates an embodiment of a pressure attenuation device 17, 66, which can be configured according to the embodiments described herein, positioned within the bladder 5.

Attenuation

Figure 11A:
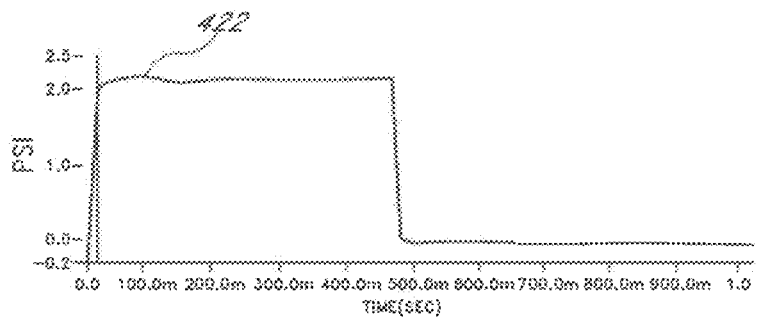
FIGS. 11A-11D present graphs of attenuation/pressure reduction vs. time for various pressure attenuation device air volumes.
Figure 11B:
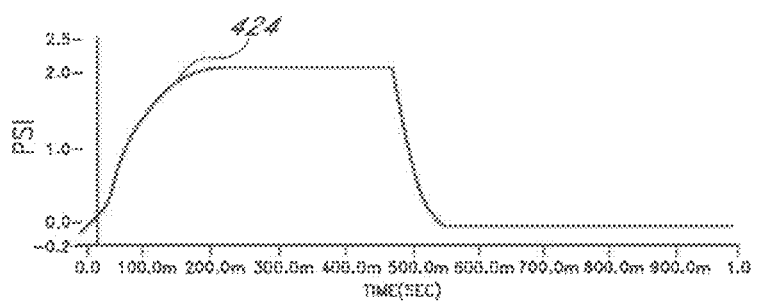
Figure 11C:
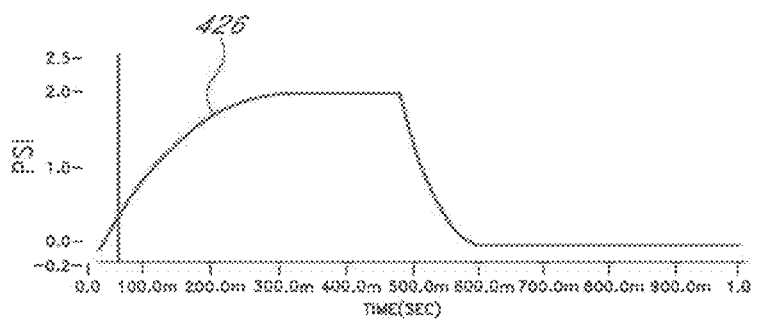
Figure 11D:
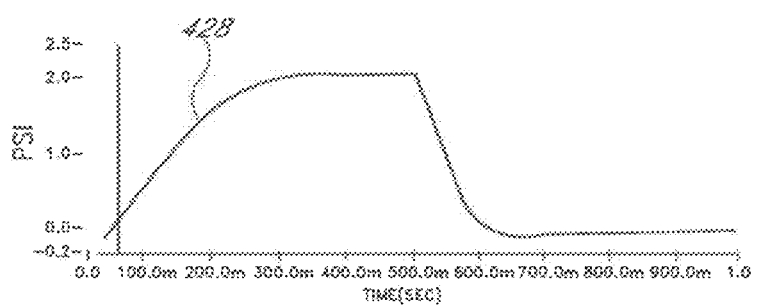

FIGS. 11A-11D illustrate the principle of attenuation (i.e., pressure reduction) with various attenuation device air volumes. The data for these graphs were generated using a bench top bladder simulation program. Here, the maximum spike pressure is 2.0 psi. The spike event duration is approximately 40 ms, which is approximately equivalent to the duration of a coughing or sneezing event. With reference to FIG. 11A, a test was conducted with a 250 ml rigid plastic container filled with synthetic urine or water. A regulated pressure of 2.0 psi was introduced into the container via a controlled solenoid valve. A pressure transducer detected the pressure rise. Here, the pressure rise time (Tr) of the container pressure 422 to reach 2.0 psi was approximately 40 msec. With reference to FIG. 11B, a similar test was conducted on a 250 ml rigid plastic container. Here, an attenuation device filled with 15 ml of air was placed inside the container filled with synthetic urine. Here, the Tr of the container pressure 424 to reach 2.0 psi was approximately 195 msec. Thus, the attenuation device slowed the rise time by 4.8×. During the spike event (i.e., when time equaled 40 msec), the pressure inside the container reached 0.7 psi (vs. 2 psi), resulting in a 65% reduction of pressure vs. baseline. With reference to FIG. 11C, a similar test was conducted; the only difference being that the attenuation device was filled with 25 ml of air. Here, the Tr of the container pressure 426 to reach 2.0 psi was approximately 290 msec. Thus, the attenuation device slowed the rise time by 7.25×. During the spike event (i.e., when time equaled 40 msec), the pressure inside the container reached 0.5 psi (vs. 2 psi), resulting in a 75% reduction of pressure vs. baseline. With reference to FIG. 11D, a similar test was conducted; the only difference being that the attenuation device was filled with 30 ml of air. Here, the Tr of the container pressure 428 to reach 2.0 psi was approximately 340 msec. Thus, the attenuation device slowed the rise time by 8.5×. During the spike event (i.e., when time equaled 40 ms), the pressure inside the container reached 0.4 psi (vs. 2 psi), resulting in an 80% reduction of pressure vs. baseline.

Figure 12A:
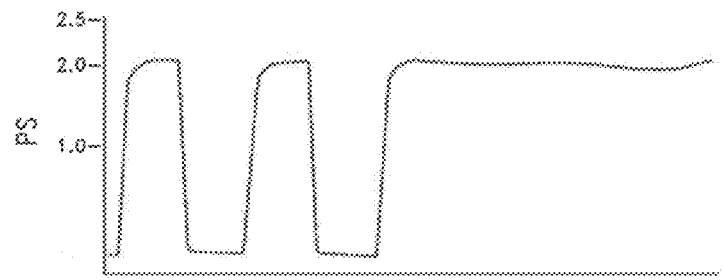
FIGS. 12A-12D show pressure vs. time curves generated by a bench top bladder simulator.
Figure 12B:
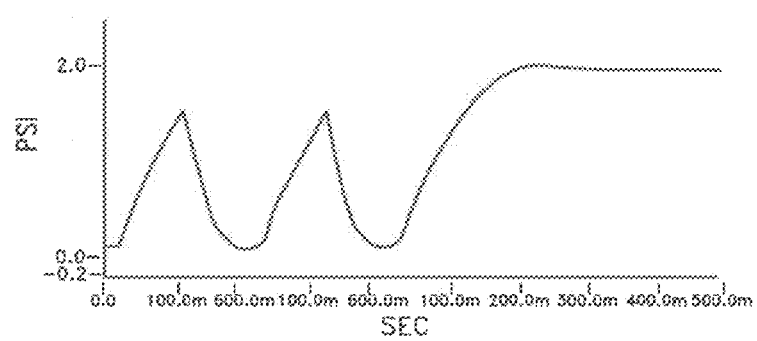
Figure 12C:
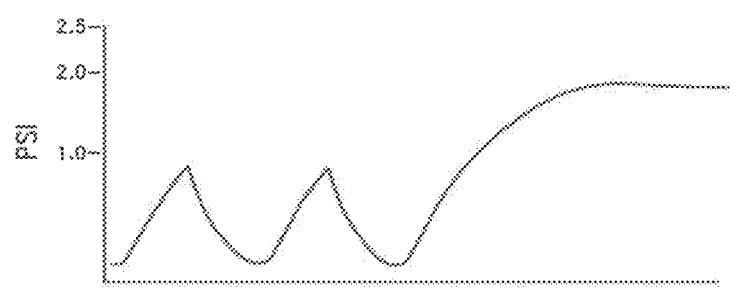
Figure 12D:
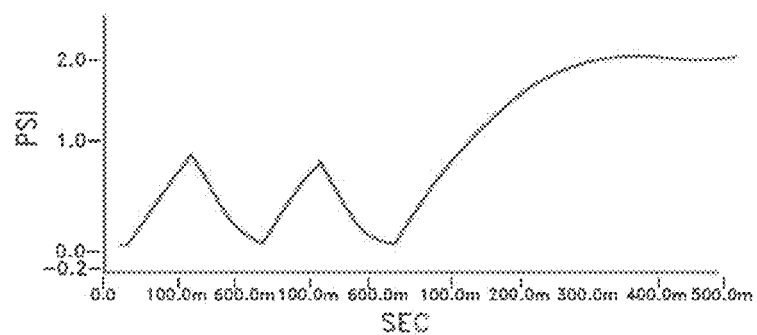

FIGS. 12A-12D show pressure vs. time curves generated by a bench top bladder simulator. FIG. 12A shows the baseline pressure-time curve without an attenuation device. FIG. 12B shows the pressure-time curve with an attenuation device having a 15 cc air volume. FIG. 12C shows the pressure-time curve with an attenuation device having a 25 cc air volume. FIG. 12D shows the pressure-time curve with an attenuation device having a 30 cc air volume.

Embodiments of the pressure attenuation devices 17, 66 discussed herein can have the ability to treat and/or prevent stress urinary incontinence by attenuating pressure within the bladder in a manner as described above. For example, a method of preventing stress urinary incontinence can include providing a pressure attenuation devices 17, 66 operable to reversibly occupy intravesical space in response to a pressure increase event within a bladder said response operable to impede the rate of an intravesical pressure increase event during an initial period. The initial period can be around 0 milliseconds to 1 second from the event. This can beneficially allow time for neurological signaling of a guarding reflex to increase the outlet resistance of an external urinary sphincter sufficient to prevent leakage of urine through said sphincter after said initial period. The selected treatment period can beneficially facilitate rehabilitation of a neuromuscular system of the bladder and restoration of continence.

Pressurized Implants

All liquids (and for that matter solids) will evaporate at a given temperature until they saturate the space above the liquid with their vapor. The pressure exerted by that saturated vapor is the vapor pressure. The vapor pressure goes up with temperature and when a liquid is heated until its vapor pressure is greater than one atmosphere, it boils while trying to maintain the space above it at its vapor pressure, now more than one atmosphere. Likewise if the vapor of a liquid is concentrated (e.g., compressed) to be present at a partial pressure (concentration) greater than its vapor pressure, it condenses. Some liquids have very low vapor pressures (e.g., cooking oil, high molecular weight PFCs) and some have high vapor pressures (e.g., alcohol, gasoline, lower molecular weight PFCs). Within this document the abbreviation, PFC, is used for perfluorocarbon.

Partial pressure is both a measure of pressure (force/area) and a unit of gas concentration (at constant temperature, proportional to moles/volume). A "p" placed in front of the chemical symbol of a gas generally denotes it as the partial pressure of that gas, e.g., $pCO_2$. The total of all partial pressures inside a container is the gas pressure measured inside that container. Diffusion is controlled by the difference in concentration across a boundary or membrane and thus for gases the rate is proportional to the difference in partial pressures of the gas on both sides of a membrane.

Gas tension is a measure of the amount of a gas dissolved in a liquid (e.g., $O_2$ or $CO_2$ in blood, urine). It is a preferred measurement for the liquid systems described here. Gas tension is defined as the partial pressure of a gas that would equilibrate with the liquid sample causing it to contain the same quantity (g/ml or moles/liter) of that gas as is in the test sample. It is expressed as a partial pressure with units of mm Hg, torr, or cm $H_2O$.

Many of embodiments of the devices described herein rely on compliance to attenuate or buffer pressure spikes, such as in the bladder. Compliance is the change in volume (V) of a device per unit change in applied pressure (P) on the device (dV/dP). This is the slope at any point in a plot of volume (V) of the device vs. pressure (P) applied to the device. For example, compliance is often calculated from V vs. P curves of the lung to indicate the effort needed to breathe. In our case it is a measure of how capable a device is of dampening a pressure spike. High compliance means a large device volume reduction to relieve a given pressure spike. Since the V vs. P curve is often non-linear, the slope, dV/dP=compliance, is not constant throughout the working region of a device. Internal gas pressures, geometry of the device, volume of the device and elasticity of the skin of the device can be chosen to maximize compliance under the conditions expected for each application.

Tables and charts are readily available which show the vapor pressure of a given PFC as a function of temperature and can be useful in designing a device with certain pressure properties, as shown herein.

For liquids, the amount of dissolved gas is stated as a gas tension. This is the equilibrated partial pressure of the gas that results in the amount of dissolved gas. Since this is the liquid concentration that is relevant for diffusion across biological membranes, it is commonly used in medicine for gases in the blood e.g., $pO_2$ or $pCO_2$ and has units of pressure, e.g., mm Hg, or cm $H_2O$. Gas tensions are actually a measure of saturation level rather than true concentrations. Thus, a sample of blood with an $N_2$ tension of 593 mm Hg or $O_2$ tension of 160 mm Hg would be saturated with those gases when exposed to a gas mixture containing partial pressures of 593 mm Hg of $N_2$ or 160 mm Hg of $O_2$. This is regardless of how many moles or milligrams per ml were dissolved in the sample. Unlike gaseous systems where compression of the system elevates the gaseous partial pressures in the system, gas tensions of gas molecules dissolved in an incompressible liquid are not affected by hydrostatic pressures.

Another factor to consider is the fact that a vessel/balloon containing a gas and/or a liquid could be constructed of an elastic material. As the pressure of gas inside the balloon increases relative to the pressure outside the vessel, the vessel can seek to expand to neutralize the difference in pressure between inside and outside the vessel. As the vessel expands it will stretch and exert a force which countermands the force of the gas pressure within. This is sometimes known as skin tension causing skin pressure. Thus, an equilibrium state could exist where the pressure outside such an elastic vessel is 760 mm Hg, the pressure inside the vessel is 780 mm Hg, and the skin tension of the vessel exerts a force on the gas within it that is equal and opposite to the expansionary force of the extra 20 mm Hg within the vessel.

It is important to consider the gases and the concentrations of those gases which can be found within the body when placing an implant therein. Generally, there is a close relation to the gases found in the ambient atmosphere outside the body, and those within. In normal air, the largest component is nitrogen. The components of a gas are, in fact referred to according to their partial pressures. That is, when it is said that air is 78% nitrogen, it means that this is the percentage of the total gas pressure due to nitrogen. The second most common component is oxygen, whose partial pressure contributes 21% of total atmospheric pressure. Other gases make up the remaining 1% (e.g., $CO_2$ is 0.04% and thus can be neglected in most calculations discussed herein) of the total pressure. Also, the body does not metabolize nitrogen, and it is present within the body's fluids, and its partial pressure contribution is related to its contribution outside the body, limited by its solubility in the respective fluids. Thus, if the ambient pressure is 760 mm Hg, then the total pressure is 760 mm Hg, the partial pressure of nitrogen is 593 mm Hg or 78%. The partial pressure of oxygen, expressed as $pO_2$, is 160 mm Hg, or 21%. The partial pressure of the remaining gases would be about 8 mm Hg, or about 1%.

The nitrogen concentration in blood is related to nitrogen's solubility in blood but, since it is not metabolized, its gas tension is essentially equal to the nitrogen partial pressure in air. The oxygen concentration in blood is more complex, since oxygen is actively bound to hemoglobin in the blood—boosting blood's capability to carry oxygen. Also, unlike nitrogen, oxygen is metabolized in the body, so its concentration can vary significantly within the body. The amount of oxygen present in blood varies and is reported as "oxygen saturation," or the % of the maximum oxygen that blood can carry or the oxygen tension $pO_2$. For a healthy person, this is typically in the range of 95 to 98%. Venous blood is typically in the range of 60 to 80%. When considering the diffusion of oxygen across membranes the preferred measurement is the oxygen tension or $pO_2$. Oxygen concentration in fluids such as cerebrospinal fluid, vitreous humor and bladder urine also varies.

In the article "Noninvasive Oxygen Partial Pressure Measurement of Human Body Fluids in Vivo Using Nuclear Magnetic Imaging" by Zaharchuk et al. (Acad. Radiol. 2006; 13:1016-1024), a table of gas tensions of oxygen in various body fluids is detailed. Information from that article is summarized in Table 1, below. The authors, Zaharchuk et al., attempted to measure partial pressure of gases in the body using MRI. In an effort to verify their measurements they performed a literature review to see what other researchers had estimated the partial pressures to be.

In Table 1, the oxygen partial pressure for particular bodily fluids is given. The middle column is Zaharchuk's measurement and the right column is what they found by studying the literature. Also, one should note that the partial pressure of oxygen in the atmosphere is 160 mm Hg and thus fully air equilibrated fluids, if there were no consumption, would have oxygen tensions of 160 mm Hg.

TABLE 1

Body Fluids and Oxygen Partial Pressure Values

| Body Fluid | Actual $pO_2$ measured by Zaharchuk et al. (mm Hg) | Literature Review "best estimate" range of $pO_2$ (mm Hg) |
| --- | --- | --- |
| Cerebrospinal fluid in Lateral ventricles | 52 +/− 14 | 30-74 |
| Cerebrospinal fluid in Cisterna magna | 62 +/− 29 | 31-74 |
| Cerebrospinal fluid in cortical sulcal | 138 +/− 46 | Not Found in the Literature |
| Cerebrospinal fluid in lumbar subarachnoid | 69 +/− 22 | 40-57 |
| Vitreous Humor | 63 +/− 34 | 9-20 |
| Bladder Urine | 63 +/− 16 | 25-80 |

Pressure within the abdomen and within the bladder is typically measured in units of "centimeters of water" or cm $H_2O$, where 1.0 mm Hg corresponds to 1.33 cm $H_2O$. So, for example, the partial pressure of oxygen in atmospheric air is about 212 cm $H_2O$, and the partial pressure of oxygen in bladder urine is approximately 84 cm $H_2O$. Hence, there is a partial pressure "deficit" of oxygen in bladder urine corresponding to approximately 128 cm $H_2O$.

Provided herein are improved pressurizable, compressible, and/or expandable devices for attenuating pressure waves or spikes in the body and for preventing or relieving various pathological conditions and improving surgical outcomes.

Several of the therapeutic devices herein are comprised of implantable balloons, vessels, enclosures, envelopes, pistons, or hydraulic devices that contain gas or gas/liquid mixtures. Such devices can define a range of permeability. Examples of such devices can be found in U.S. Pat. No. 7,347,532 and US Publication No. 2007-0156167 herein incorporated by reference. Various embodiments herein provide for rapid, delayed, or controlled in situ inflation or deflation. In other embodiments, the devices are further comprised of relatively soft, distensible, thin, and consequently gas permeable membranes. Over time these devices will deflate and become ineffective or fail unless fitted with a "gas generator" of a selected high vapor pressure media. Certain other methods and devices provided herein include the maintenance of inflation for a selected period of time by providing the pressure attenuation device with a high vapor pressure media.

In some embodiments, the pressure attenuation device 17, 66 as described herein is placed in the bladder to attenuate pressure spikes that would otherwise cause urinary incontinence. As shown in FIGS. 13A and 13B, pressure "P" on the bladder, for example from physical activity can cause urine leakage 104 in those who suffer from urinary incontinence. Embodiments of the implant 17, 66 (schematically illustrated in FIG. 13B as positioned within the bladder) can be positioned within the bladder to absorb the pressure in the bladder so that there is no urine leakage.

The pressure within the bladder is typically a little bit higher than atmospheric pressure, since it typically contains urine which displaces the bladder's muscular walls. The walls of the bladder, through their muscle tone and mass, exert force on the urine inside, resulting in typical pressures that can be around 15 cm $H_2O$ above atmospheric in some patients. For the sake of simplifying discussion in this document, we will simply use this number as an approximation of average bladder pressure. If the balloon is under-filled with air such that there is no skin pressure to consider, then there will be a situation immediately before the balloon is placed in the bladder where the pressure within the bladder is atmospheric plus 15 cm $H_2O$, and the pressure within the balloon is atmospheric pressure. When the balloon is placed within the bladder, the balloon will instantaneously compress, so that its contents are at the same total pressure as the hydraulic pressure with which the urine in the bladder is pressing on the balloon. That is, the now slightly compressed gas will press outwards on the walls of the balloon with the same force that the liquid in the bladder will push inwards. This "force equilibrium" of exactly equal and opposite forces exerted from within the balloon outwards, and outside the balloon inwards is one equilibrium that should be considered in this example.

In the force equilibrium, the liquid or hydraulic pressure within the bladder pushes on the balloon, and the now slightly compressed gas within the balloon pushes outwards on the liquid. The inwardly pushing forces should balance with the outwardly pushing forces or the balloon will either burst or collapse.

The second equilibrium to be considered is partial pressure equilibrium. The partial pressures of the individual gas constituents within the balloon will seek to equilibrate with the gas tensions of the dissolved gas in the liquid outside the balloon.

In this example, first assume that initially, before the balloon was inserted, that the proportions of gas in atmospheric air were in the balloon, and that the same proportions of dissolved gas existed in the urine. The balloon was compressed slightly when it was inserted, so all of the partial pressures of the gas constituents increased by an amount proportional to the decrease in volume due to the compression. This results in a situation where there will be higher partial pressures of the individual gas components inside the balloon versus the gas tensions of the same gases outside the balloon. This will result in diffusion of these gases out of the balloon into the urine. As the gases leave the balloon, the balloon will shrink to maintain the force balance. In this example, this net out-of-the-balloon gas diffusion will continue until the balloon is completely empty. The rate of deflation will be a function of the permeability of the membrane to the gases held within and the difference between the hydrostatic pressure in the bladder and the total gas tension of gases dissolved in the urine.

In one aspect of certain embodiments of the disclosure is the addition of a high vapor pressure media such as PFC to the contents of the balloon. Since some selected or preferred PFCs have high vapor pressures, the partial pressure of the PFC will add to the existing partial pressures of the other gases to increase the overall gas pressure in the device. A small amount of liquid high vapor media such as PFC within the balloon serves as a reservoir or generator and will offset losses due to slow diffusion and maintain a constant PFC partial pressure.

The stable size of the balloon depends on the maintenance of a supply of liquid high vapor pressure media such as PFC inside the balloon, the balance of force as regulated by balloon size, and the balance of partial pressures. If any of these key factors moves out of balance the balloon will either grow or shrink.

Selection and Determination of the Vapor Pressure or Partial Pressure PFC Element In a simplified embodiment involving an air-filled balloon placed into the bladder or other liquid filled bodily organ one will note that the device will float in the bladder and rest near the top of the bladder. It will not deflate; therefore there is equilibrium between the air inside the balloon and the liquid pressing upon it. The gas molecules inside the balloon provide an internal force ($F_{HA}$) that presses outwards, and the hydraulic pressure of the urine provides an external force ($F_{ext}$) that presses inward on the balloon. For the balloon to exist, the forces should be in balance as illustrated here, that is $F_{int}=F_{ext}$. The internal force is created by the pressure of the gas inside the balloon.

In this example, the gas inside the balloon was normal atmospheric air, at sea level, when it was inserted. So its total pressure before insertion was approximately 760 mm Hg which is approximately equal to 1000 cm $H_2O$. This total pressure of 1000 cm $H_2O$ is, as described by Dalton's law, equal to the sum of the partial pressures of its gas components. Normal atmospheric air is comprised of approximately 78% nitrogen, 21% oxygen, and 1% other gases. Since the total pressure is 1000 cm $H_2O$, we can surmise that the partial pressure of nitrogen or $P_{N2}$ is equal to 780 cm $H_2O$, the partial pressure of oxygen or $P_{O2}$ is roughly 210 cm $H_2O$, and the partial pressure of other gases or $P_{OG}$ is 10 cm $H_2O$. The partial pressures and total pressure of the balloon outside the bladder are shown in Table 2.

TABLE 2

| Internal Balloon Pressure When Outside the Bladder | | |
|---|---|---|
| | $P_{N2}$ = | 780 cm $H_2O$ |
| | $P_{O2}$ = | 210 cm $H_2O$ |
| + | $P_{OG}$ = | 10 cm $H_2O$ |
| Balloon total pressure = | | 1000 cm $H_2O$ |

As soon as the balloon is inserted into a urine filled bladder or organ, it will be subjected to hydraulic pressure due to the muscle tone of the abdomen and bladder pressing on the urine within. This is a frequently measured physiological parameter, and 15 cm $H_2O$ is a typical value, so we will use this in our example. Now, the patient into whom the balloon has been inserted is residing at sea level, so this "inside the bladder" (or intravesical) pressure is equal to the sum of atmospheric pressure plus the 15 cm $H_2O$, or 1015 cm $H_2O$. This means that in order to satisfy the force equilibrium, the total pressure inside the balloon changes so that it equals 1015 cm $H_2O$ also. It does this by compressing and getting smaller. The balloon will instantaneously compress as it is inserted into the bladder. According to Boyle's law, the pressure and volume of a gas are directly proportional according to the relationship: $P_1V_1=P_2V_2$. This means that in order for the gases' volume to decrease, its pressure increases, in this case by 15 cm $H_2O$ or by 1.5%.

The total pressure of the gas inside the balloon has now changed, due to the compression, but the molar quantities and proportions of the gases within has not changed. Table 3 shows the partial pressures and total pressure of the balloon inside the bladder are (with rounding).

TABLE 3

| Internal Balloon Pressure When Inside the Bladder | | | |
|---|---|---|---|
| | $P_{N2}$ = | 780 + 1.5% = | 792 cm $H_2O$ |
| | $P_{O2}$ = | 210 + 1.5% = | 213 cm $H_2O$ |
| + | $P_{OG}$ = | 10 + 1.5% = | 10 cm $H_2O$ |
| Balloon total pressure = | | | 1015 cm $H_2O$ |

In this example, gas diffusion equilibrium should also be considered. Urine in the body, like other body fluids, contains dissolved gas. The amount of gas dissolved in these fluids is governed by the gases' solubility in the fluid, and whether or not it reacts chemically or biologically with the fluid. For example, blood can contain a much higher percentage of oxygen than water, due to the fact that the oxygen is bound to the hemoglobin in red blood cells. The gas tensions of gases in urine will be different than the partial pressures of gases found in atmospheric air (most likely lower). The gas tensions will also not be governed by the hydraulic pressure of the fluid, since these fluids are, relative to gas, incompressible and hydraulic pressure does not affect their solubility.

In an embodiment wherein the balloon is constructed of a material that is permeable to gas, the gas will seek to diffuse from the high partial pressures in the balloon into the liquid where the gas tensions are lower. For example, consider the fact that the partial pressure of oxygen in bladder urine could be around 84 cm $H_2O$ (as described previously) and in this example, the partial pressure of oxygen is 213 cm $H_2O$ in the balloon. This gradient will result in oxygen exiting the balloon at a rate determined by the gas permeability of the wall of the balloon. As the oxygen exits, the balloon will shrink to maintain the force equilibrium. This exiting of oxygen, and balloon shrinkage will be echoed by nitrogen and the other gases present, although at varying rates. The end result will be complete deflation of the balloon over time.

A means to maintain balloon inflation, as described herein, is to provide a supply of liquid PFC inside the balloon. The liquid PFC will rapidly vaporize, and provide a supply of PFC gas whose partial pressure is "locked" at the vapor pressure of the PFC. This PFC will not diffuse out of the balloon as it is not soluble in water or urine. Let's consider a balloon containing a PFC whose partial pressure is 120 cm $H_2O$, plus normal air, inserted into the bladder as before. Table 4 shows the partial pressures, if the balloon was hypothetically filled outside the bladder at atmospheric pressure, before the PFC has a chance to vaporize.

TABLE 4

Internal Balloon Pressure Before Vaporization

|   | | |
|---|---|---|
| | $P_{N2}$ = | 780 cm $H_2O$ |
| | $P_{O2}$ = | 210 cm $H_2O$ |
| | $P_{OG}$ = | 10 cm $H_2O$ |
| + | $P_{PFC}$ = | 0 cm $H_2O$ |
| Balloon total pressure = | | 1000 cm $H_2O$ |

In an example embodiment, outside the bladder situation, as the PFC vaporizes, the balloon will expand to maintain the force equilibrium. The gas quantities and proportions other than the PFC will remain constant, so they are, in effect, diluted by the PFC whose partial pressure will be fixed at its vapor pressure of 12-cm $H_2O$. Thus, moments later, the partial pressures in the now expanded balloon will be as shown in Table 5. The balloon will have expanded 12%, the partial pressures of the constituent gases other than PFC will maintain their proportions since the moles of gas are the same; however they will reduce proportionally as shown:

TABLE 5

Internal Balloon Pressure After Vaporization

|   | | |
|---|---|---|
| | $P_{N2}$ = | 686 cm $H_2O$ |
| | $P_{O2}$ = | 185 cm $H_2O$ |
| | $P_{OG}$ = | 9 cm $H_2O$ |
| + | $P_{PFC}$ = | 120 cm $H_2O$ |
| Balloon total pressure = | | 1000 cm $H_2O$ |

If this balloon is placed into the bladder, then the bladder pressure, 15 cm $H_2O$, should equilibrate to a new total pressure of 1015 cm $H_2O$ as before. The balloon will shrink by 1.5% and the new partial pressures are shown approximately in Table 6.

TABLE 6

Internal Balloon Pressure After Vaporization When Inside the Bladder

|   | | |
|---|---|---|
| | $P_{N2}$ = | 697 cm $H_2O$ |
| | $P_{O2}$ = | 189 cm $H_2O$ |
| | $P_{OG}$ = | 9 cm $H_2O$ |
| + | $P_{PFC}$ = | 120 cm $H_2O$ |
| Balloon total pressure = | | 1015 cm $H_2O$ |

If the gas tension of dissolved gas in the urine is lower than the new partial pressures in the balloon, gas will be driven out of the balloon at a rate which is regulated by the gas permeability of the balloon, and the balloon will shrink. If the partial pressure of the dissolved gas in the urine is higher than these new partial pressures, then gas will be drawn into the balloon at a rate which is regulated by the gas permeability of the balloon, and the balloon will grow. However, the partial pressure of the PFC will remain fixed. Note that for simplicity, this example excluded the impact of the skin tension of the balloon. The next example will consider skin tension.

The partial pressure of the PFC can be selected by tuning its vapor pressure. In order to maintain a balloon whose volume is stable, the PFC should be selected so that a diffusion balance is maintained. The formula can be derived as follows. First, the pressure inside the balloon equals the pressure outside the balloon, or else the balloon will collapse or burst.

$$P_{Inside\ Balloon} = P_{Bladder\text{-}avg} + P_{Skin\text{-}tension} \quad (1)$$

As discussed herein, $P_{Inside\ Balloon}$ (the pressure inside the balloon) is equal to the sum of the partial pressures of the gases within the balloon. As shown here, it is also equal to the hydraulic pressure pushing upon it plus the pressure due to the balloon skin. The term, $P_{Bladder\text{-}avg}$, comprises the hydraulic pressure pushing upon the balloon due to abdominal pressure, bladder muscle tension and other factors. The skin pressure, P skin-tension, is the inward force exerted by the stretching material of a balloon's walls, or in other cases, simply the weight exerted on the gas within by a flaccid under inflated balloon. This equation is simply another version of the "force equilibrium" equation described earlier.

At the same time, recall that the total pressure within the balloon is equal to the sum of the partial pressures of the gases it contains:

Note: All pressures below are absolute pressures $$P_{Inside\ Balloon} = P_{N2\text{-}balloon} + P_{O2\text{-}balloon} + P_{other\ gases\text{-}balloon} + P_{PFC} \quad (2)$$

Since the partial pressure of the other gases is only 1% of the sum of all the non PFC gases, this can be approximated as being zero, so:

$$P_{Inside\ Balloon} = P_{N2\text{-}balloon} + P_{O2\text{-}balloon} + P_{PFC} \quad (3)$$

Equation (1) from the force equilibrium was as follows:

$$P_{Inside\ Balloon} = P_{Bladder\text{-}avg} + P_{Skin\text{-}tension} \quad (1)$$

Therefore combining equations (1) and (3) gives:

$$P_{Bladder\text{-}avg} + P_{Skin\text{-}tension} = P_{N2\text{-}balloon} + P_{O2\text{-}balloon} + P_{PFC} \quad (4)$$

Over time, gas diffusion will occur, and $P_{N2\text{-}balloon}$ and $P_{O2\text{-}balloon}$ will equilibrate to values that approximate the partial pressures of oxygen and nitrogen dissolved in the urine (their gas tensions). Therefore:

$$P_{N2\text{-}balloon} + P_{O2\text{-}balloon} = P_{Dissolved\ gas} \quad (6)$$

And by combing (4) and (6) we get:

$$P_{Bladder\text{-}avg} + P_{Skin\text{-}tension} = P_{Dissolved\ gas} + P_{PFC} \quad (7)$$

Or $$P_{PFC} = P_{Bladder\text{-}avg} + P_{Skin\text{-}tension} - P_{Dissolved\ gas} \quad (8)$$

Where:

$P_{PFC}$=The desired vapor pressure of the PFC.

$P_{Bladder-avg}$=The average bladder pressure over time (i.e., course of a day) or more generally, the anatomical environment/hydrostatic average.

$P_{dissolved-gases}$=The total gas tension of bladder urine.

$P_{skin\ tension}$=The inward force exerted by the skin of the balloon.

More generally, the equation for selecting a PFC suitable for maintaining a pressurized device according to one or more aspects of the disclosure in a given anatomical environment is:

$$P_{PFC}=P_{anatomical\ environment/hydrostatic-avg}+P_{Skin-tension}-P_{Dissolved\ gas} \quad (9)$$

In another embodiment the selection for the high vapor pressure element can be described as:

$$\text{atmospheric pressure}+P\text{pfc}=\text{external pressure or loads on implant} \quad (10)$$

Where the external loads include: tension generated by skin of the balloon, normal somatic pressure during fill and void of organ (if applicable), transient somatic pressure, e.g., abdominal, patient generated valsalva, bodily weight on organ e.g., abdominal weight on bladder or on bladder wall/balloon when the bladder is empty, differential between gas tensions in body fluid and partial pressures within balloon.

Having shown how to determine an appropriate vapor pressure for the PFC element, one can now select an appropriate mixture of PFCs to approximate this value. The $P_{PFC}$ can be selected by mixing PFCs of different vapor pressures, and calculating the composite vapor pressure based on the proportions of the moles of the individual PFCs.

One consideration is the average pressure within the desired area of the body ($P_{anatomical\ environment/hydrostatic-avg}$). In the example of a device implanted in the bladder, the average pressure within the area of the body would be a time average of the pressure in the bladder ($P_{Bladder-avg}$). This would encompass the average of: the low pressure of slowly filling bladder; pressure spikes from events such as laughs, coughs or sneezes; higher pressures achieved during micturition, or during valsalva. Other hollow organs and tissue sites would similarly vary in pressure ranges, from which an average value could be calculated.

Another consideration is the total gas tension of the bodily fluid in the particular area of the body ($P_{Dissolved\ gas}$) to be treated. This includes all the dissolved gases in the bodily fluid such as oxygen, nitrogen, carbon dioxide, or other gases. In the bladder, the bodily fluid is urine. The total gas tension in urine can vary based on the patient's diet, presence of substances in the urine that bind oxygen or other gases, or the gases that the patient is inhaling. For example, a patient breathing pure oxygen would have a higher oxygen gas tension. It is also worth noting that gas tension will almost always be less than the hydrostatic, anatomical pressure, or bladder/organ/implantation site pressure. Also note that the driving force for deflation is that the concentration of gases inside the device is higher than the total gas tension outside the device.

Several of these parameters will vary from patient to patient. For example, average bladder pressure in men is generally higher than that of women. Average bladder pressure can vary from person to person within a gender based on how full each individual lets their bladder get before voiding. Also, average bladder pressure can vary due to pathology, for example, due to a condition known as detrusor instability which causes undesired contractions of the bladder's muscular walls. Bladder pressure can also vary due to physical activity. One would expect that the average bladder pressure of a weight lifter would be higher during a weight lifting competition than it is for a sedentary individual. As mentioned herein, the bladder gas tensions can vary based on diet, lung function, metabolic rate, and other factors.

An additional consideration is the skin tension of the balloon. The skin tension of the balloon can vary based on many factors, including the material of the balloon, the thickness of the material, and its means of construction. It can also vary based on how "stretched" it is. For example, a balloon that has a volume of 3 ml when empty and is filled with 15 ml will be much more stretched than the same balloon filled to 5 ml.

It is conceivable that a balloon that has a stable volume over time could be created by measuring each of the above parameters and selecting the PFC based on that. Also, an individual could be "titrated" so that various PFCs are tried and one that is stable over time is selected. A combination of the two methods could be used as well—for example, gross measurement of physical parameters followed by "trying" PFCs of different partial pressures.

Various means could be used to achieve this measurement and/or titration. For example, a pressure sensor that resides in the bladder and either transmits data out of the bladder telemetrically, or stores it for later retrieval, could be used to determine average bladder pressure. Pressure information of other hollow organs such as the eye, heart, cranium, lungs, stomach, liver, gall bladder, etc. or bodily sites could similarly be obtained. Sensors, such as those used for blood gas measurement could be used to measure the total gas tension of urine in the bladder and the individual tensions of the constituent gases. Finally, balloons can be selected or filled in order to achieve a desired skin tension. Test device involving balloons with strain gauges and pressure gauges to record or transmit data for short time could also be used to determine pressures and skin tension values.

Two examples of how the gas pressures in urine could be measured include the use of a blood gas analyzer, such as those available from Radiometer America Inc. or the MRI approach described by Zaharchuk et al., referenced herein.

A blood gas analyzer can be used to sample gases in the urine. A patient's bladder would be allowed to fill normally. A catheter or tube would be inserted into the patient's bladder. Urine would be extracted into a syringe or vial. The vial would be inserted into the machine, and standard readouts can be obtained. $PO_2$ (partial pressure of oxygen in the sample) is an example.

The blood gas analyzer runs the risk of inaccuracies related to how quickly the measurement is performed. The sample can become contaminated in the time between taking the sample and sending to the lab. Also, the measurement may not be as accurate as needed since there is measurement error in the machine. A difference of 10 cm $H_2O$ can be enough to make the difference with regard to a balloon inflating or deflating thus, these inaccuracies can be make the error too great to be useful.

Concerning MRIs, MRI machines are big, and expensive. Thus, it is not practical to place every patient inside an MRI machine. Furthermore the accuracy of the method ranges from +/−14 mm Hg to +/−46 mm Hg. 14 mm Hg corresponds to +/−18.6 cm $H_2O$, too broad a range for most applications described herein.

A preferred method is to "titrate" the PFC. First, based on the information described herein the Physician can estimate the relative gas partial pressures in urine and the needed partial pressure of the PFC. For example, the estimate can be in the range of 100 to 130 cm H₂O. A clinical study can be performed in which a series of patients are studied using balloons containing PFC with a partial pressure of 110 cm H₂O. The state of these patient's balloons upon removal would be monitored carefully. One possible result is that on average the balloons could be decreasing slightly in size over a 3 month period. Continuing the example, another series of patients could be studied using a PFC with a vapor pressure of 120 cm H₂O. Upon examining their balloons after 3 months, one possible result is that their balloons could be growing slightly in size over 3 months. This result would tell us that the ideal vapor pressure would be in between 110 and 120 cm H₂O. The next step would be to try a series of patients with a vapor pressure of 115, and so on.

One advantage of the titration method is that the desired outcome is the best partial pressure on average over time. The partial pressure of oxygen in urine, for example, will change over the course of the day. It is likely to be different during sleeping and waking hours. It can also be affected by diet, for example, eating foods rich in ascorbic acid (vitamin C) can affect oxygen partial pressure. The titration method yields the value that is optimum for the long term successful inflation of the balloon. Other methods that provide an instantaneous measurement (such as blood gas monitors or MRI) would not provide this benefit. It would be impractical to make such measurements many times over the course of a day, days, or even weeks or months.

Setting the Vapor Pressure of the Selected PFC Element

The PFC vapor pressure of the PFC element or additive can be set by choosing the molecular weight/number of carbons and isomer form of the PFC (rings, branched, linear) or using hetero-atoms such as Br or H. These pure compounds will have a constant vapor pressure throughout the life of the device as it very slowly looses PFC through the aqueous fluid surrounding the device.

Intermediate vapor pressures can also be produced by using mixtures of PFCs, though these mixtures will change component ratios after initial vaporization and slowly through the life of the device. If mixtures are used, an excess quantity of PFC should be put in the device to minimize the vapor pressure changes (unless we want the vapor pressure and thus inflation pressure to slowly decrease). The vapor pressure of a liquid mixture can be predicted by Raoult's Law where the total vapor pressure is the sum of each component PFC vapor pressure times its mole fraction in the liquid. This means the most volatile component leaves faster and the vapor pressure of the remaining PFC mixture slowly drifts toward the vapor pressure of the least volatile component in the mixture. This effect is exacerbated as the higher vapor pressure PFCs also are in general lower in molecular weight so they also diffuse faster and have higher water solubilities.

Examples of PFCs suitable for use as a high vapor pressure media in various devices described herein include: perfluoropropane, perfluorobutane, perfluoropentane, perfluorohexane, perfluoroheptane, perfluorooctane, perfluorononane, perfluorodecane, perfluorooctylbromide, perflubron, and perfluorodecylbromide. As explained herein, two or more PFCs can be combined to form a liquid mixture with a particular vapor pressure according to their mole fraction in the liquid. A preferred range of vapor pressures for a PFC element in one or more embodiments is around 50-200 cm H₂O. In other embodiments the preferred range of selected vapor pressures for a PFC element is around 100-150 cm H₂O. In other embodiments, for example in the bladder, the preferred range of selected vapor pressures for a PFC element is around 115-130 cm H₂O, around 120 cm H₂O or around 115-117 cm H₂O. For example, in some embodiments a mixture of about 0.5 mole perfluorooctane and about 0.5 mole perfluoroheptane can result in a vapor pressure of between around 115 and 130 cm H₂O at 37° C. In another example, a mixture of 0.545 mole perfluorooctane and 0.455 mole perfluoroheptane can result in a vapor pressure of about 120 cm H₂O. The preferred range of selected vapor pressures for a PFC element can be based in part on pO₂ of the anatomical structure. Thus, for example, areas of the body with a pO₂ similar to that of the bladder can also use a similar PFC pressure range. As pO₂ increases the desired PFC vapor pressure range decreases.

Volumes of the PFC element are generally limited by the volume of the organ or tissue site in which the implant containing the PFC element is implanted and by the duration in which the pressurization is intended to be maintained. A preferred range of volumes for a PFC element within an implant according to one or more embodiments is around 0.1-10 ml and more preferably around 0.2-0.6 ml in certain applications involving the eye or the bladder. Total volumes of implants such a balloons or the balloons according to one or more embodiments can vary from 0.1 ml to 1.0 L.

The preferred volume for an implant will vary based on a variety of factors. The following example demonstrates some of the considerations for the total volume of an implant in a particular application. A pressurized implant is added to the bladder in order to attenuate pressure pulses in the bladder associated with stress urinary incontinence leakage. The clinical efficacy (preventing leakage) is increased by increasing the volume of the implant. In testing, it has been determined that efficacy increases proportionally to size.

The functional capacity of a typical urinary bladder is commonly in the range of 200 to 300 ml. This depends on many characteristics such as gender, age, health status, etc. If the implant is too large it will impact the bladder's ability to perform its primary function of storing urine. "Residual volume" is a parameter that is commonly measured by urologists and it describes the measured quantity of urine remaining in a patient's bladder after they have completed voiding (i.e., they think they are empty). Based on the experience of urologists it has been determined that a balloon as large as 30 to 40 ml will not likely be noticed by patients, specifically with regard to increasing their frequency of urination. Thus, a preferred balloon volume for the bladder is between 20 and 30 ml.

Selection of a PFC and Enclosure Skin Tension System

As discussed herein, one equation for the desired PFC vapor pressure is:

$$P_{PFC} = P_{anatomical\ environment/hydrostatic\ avg} + P_{Skin-tension} - P_{Dissolved\ gas} \quad (9)$$

It is possible that a skin tension and PFC could be chosen so that the two associated parameters for these characteristics are much, much larger than the other two parameters (for example between 5 and 20 times and preferably 10 times). For example in the bladder, if $P_{Bladder-average}$ is on the order of 15 cm H₂O above atmospheric pressure, or about 1015 cm H₂O absolute pressure; $P_{dissolved-gases}$ is on the order of 880 cm H₂O; then a balloon could be selected so that its skin tension pressure is 10,000 cm H₂O or greater, and a PFC could be chosen with a vapor pressure that is approximately the same amount. Then, in theory, a system could be designed that is relatively independent of the average anatomical environment pressure, here bladder pressure, and independent of the gas tension of dissolved gases. This is because, in this example, $P_{PFC}$ and $P_{skin-tension}$ are approximately equal, and much larger than the other two terms. Similarly, devices used in other anatomical environments and applications such as ophthalmic, vascular, cardio-vascular, renal, pulmonary, intracranial, etc., could be designed with similarly appropriate and corresponding skin tension and $P_{PFC}$ values.

Implant Compliance

An objective of certain devices according to one or more aspects of the disclosure is to supply compliance, dV/dP or a maximum change in volume with an elevation of pressure ($P_h$, hydrostatic pressure). The presence of an elastic skin only slightly reduces the compliance of the device. Since the compliance (dV/dP) of a gas obeying Boyle's law, $P_1/P_2=V_2/V_1$, is inversely proportional to the absolute pressure of the gas inside the device ($P_g$); as long as the added skin pressure ($P_{skin}$) is significantly less than one atmosphere (760 mm Hg, 1,033 cm $H_2O$), the compliance of the gas is only slightly reduced with an elastic skin (a skin pressure of 5% of an atm, 50 cm $H_2O$, has 95% of the dV/dP of gas without a skin).

The other cause for a reduction in compliance is that, as the device volume reduces under an external pressure increase, the pressure caused by the skin goes down, relieving some of the added pressure and reducing some of the volume change. This effect is controlled by the slope of the volume vs. pressure curve (V/P curve) of the device, which in turn is determined by the skin materials and geometry. In the case of an inelastic bag, the V/P curve starts at zero pressure at zero volume and then jumps vertically to the volume when the bag is full (a full inelastic bag does not stretch with more gas pressure inside) for any measurable pressure. This bag has no compliance at pressures that completely fill it, as the slope of the V/P curve is zero. On the other hand, a skin that is very stretchy/elastic (e.g., thin silicone) has a very gradual change in skin pressure as the volume changes (can be designed to have a large V/P slope at the operating volume) and only slightly reduces the device compliance. The small magnitudes of these effects are seen in a toy latex balloon that changes diameter/volume nearly as much as a free gas when the barometric pressure or altitude is changed.

The compliance reducing effects of the skin are reduced and in some cases overcome by the compliance increasing effects of the presence of PFC vapors, e.g., their ability to condense when compressed.

The vapor pressure of the PFC can be chosen to inflate the device at equilibrium to a volume where the V/P curve of the device has a very large positive slope or in other cases just below where the slope decreases, thereby limiting maximum volume.

The V/P curve of a device can be calculated from the known elastic properties of the material (stress/strain relationship) and mechanical principles (the law of Laplace, $P_{skin}$=2 times the skin tension over device radius). In many cases it can be better to measure the V/P curve of a device by inflating it with any fluid (e.g., air or air plus PFC) and then adjusting it. The device V/P curve can be adjusted, for example, by lowering the V/P slope using a thicker or stiffer skin material. Modifying the geometry of the device can also adjust the curve, e.g., the 1/radius law discussed herein, means that a long small radius cylinder will have a shallower, lower slope V/P curve than a sphere of the same volume.

The V/P curves of the various devices described herein can be modified in many ways using unique geometry, so that even essentially inelastic materials can have an elastic V/P curve.

Providing Skin Tension Bias to Sustain Implant Volume in Changing Pressure Environment Various embodiments of devices described herein comprise balloons, or enclosures comprising a porous vessel where internal gases and external gases dissolved in the body fluid interchange over time. Such balloons will tend to expand or contract as the result of an imbalance between the outside "loads" and the internal forces supporting the balloon. With correct PFC vapor pressure selection a small bias can be created where the balloon will grow until the tension in the skin, e.g., polymer skin, counteracts the bias of the PFC. The bias can be defined as the sum of all the partial pressures inside the balloon (PFC+air) minus the external sum of gas tensions or load in the surrounding environment. Turning to the equilibrium equation discussed previously, the PFC element in this embodiment should be greater than or equal to the other factors:

$$P_{PFC} \geq P_{anatomical\ environment/hydrostatic\ avg} + P_{Skin-tension} - P_{Dissolved\ gas} \quad (11)$$

A balloon's internal pressure verses volume can be plotted as shown in FIG. 14. In the region from about 0 to 14 ml of volume, designated as up to "A", the "balloon" is essentially a bag of air with zero skin tension. When in this "bag region" the balloon can have markedly decreased patient tolerability. At about 14 ml the bag becomes a balloon. Increasing amounts of volume put stress on the skin of the balloon and exert pressure on the internal gases (as in the region around "B"). Depending upon the balloon material and construction, this region of the graph showing the additional volume being gained will be fairly linear. This is analogous to the elastic region of a stress vs. strain curve, which will remain linear until either the elastic limit of the material is reached or the material fails.

As the volume increases, the balloon continues to stretch until the wall thickness decreases such that the balloon no longer exerts increasing levels of force on the internal gases. At this point the balloon continues to increase in size, however, the pressure inside the balloon levels off and eventually drops before the balloon fails. This area is designated with the letter "C". In balloons that yield, either due to molecular motion or thinning of the wall, this region of the graph can show slower growth or even diminishing pressure with added volume. The actual shape of the curve is material dependent. The shape shown, for example, is consistent with the behavior of silicone. Similar graphs can be made for other materials.

In the region before "A" and the region designated by "C" the balloon is unstable and tends to change volume as the result of gaseous interchange across the skin barrier. In the region designated by "C," the balloon can expand and becomes unstable, then shrink (e.g., when pressure goes back down). In the region designated by "A," the balloon can be considered "underinflated," a condition that can negatively affect implant tolerability. Balloon stability is created when a positive bias exits where the sum of the internal partial pressures is greater than the external gas tensions by an amount less than the height of the curve at "C", approximately 30 cm $H_2O$ in this example. The positive bias will increase the balloon's volume until the skin tension increases the internal pressure to offset the bias. At this point the balloon will be stable. It would take more internal pressure than exists within the balloon to further increase in volume, and it is not able to shrink as the positive bias forces the balloon volume higher than the bag region (before "A").

In this way a balloon can be engineered to remain stable in volume (as opposed to completely shrinking or expanding until failure) over extended periods of time while experiencing changes in pressure. This can be done by selecting a PFC with a slight bias over the anticipated load but, counteracted by the skin tension profile of the balloon for that pressure range.

One method of controlling the size of an air and high vapor pressure media filled porous balloon in situ uses the skin tension in the balloon wall to offset a purposely created difference between the external load and the internal resistance. This would be unnecessary if it were possible to perfectly set the PFC vapor pressure to offset the external load. However, because the pressure in the bladder fluctuates and different patients have different average bladder pressures it can be useful for a device to have some tolerance to naturally occurring fluctuations and/or to be able to be used in different patients. By using the skin tension in the manner prescribed here tolerance can be added to the naturally occurring variations in average external load on the balloon.

It has been shown that in the initial under-filled or "bag" region "A" of the curve or in the post-yield region "C", it is extremely difficult to control the balloon volume over time. In order to control the balloon volume over time in these regions, the PFC vapor pressure would have to be set precisely and the variation within and between patients would need to be very small. Conversely, by using the increasing pressure with volume nature of the "elastic" region "B" of the curve the balloon can find its own equilibrium and become stable in volume.

For example, if the average external load across a population were 100 cm $H_2O$ and the average external load across the patient population varied from 90 to 110 cm $H_2O$ then the PFC can be blended to yield a vapor pressure of 120 cm $H_2O$. Assuming the balloon is not initially over-filled, the balloon would gain volume by sucking dissolved gasses from the surrounding liquid environment. As the balloon increased in volume the pressure would go up due to the tension created in the balloon wall. This wall stress will offset the excess vapor pressure of the PFC blend and the balloon will stop growing and be at equilibrium.

Another advantage to designing the system to equalize on this part of the curve is that the balloon volume changes little with changes in the external load. This is because in order to offset small changes in external load a relatively large change in pressure is required.

The slope of the pressure vs. volume curve in this region is the result of the elastic modulus of the material and the geometry of the balloon. The acceptable limits of this curve are bounded by comfort and irritation which can be affected by high sloped (or stiff) balloons and poor volume control from balloons with low slopes in this region of the curve. Slopes of between 1 and 20 cm $H_2O$/ml of volume have been shown to provide bounds to these criteria. Slopes between 3 and 8 cm $H_2O$/ml of volume can be advantageous. As previously mentioned the slope can be designed into the balloon by the selection of material (elastic modulus) and geometry (shape and wall thickness).

Attenuation Device with Improved Performance at Various Elevations

As discussed herein, the partial pressure of oxygen in atmospheric air is about 212 cm $H_2O$, and the partial pressure of oxygen in bladder urine is approximately 54-120 cm $H_2O$. Hence, there is a partial pressure "deficit" of oxygen in bladder urine corresponding to approximately 129 cm $H_2O$. However, one aspect of the disclosure herein is the recognition that depending on a number of factors, one of which may be elevation (altitude) the partial pressure of oxygen in atmospheric air can change and alter the partial pressure deficit of oxygen in the bladder urine. Depending on the external environment, this can have little effect. However, in some external environments, the partial pressure deficit of oxygen can have a meaningful effect on the system balance. The embodiments of the pressure attenuation device 17, 66 and associated balloons 1711, 68 described herein can be configured as discussed in this section to address this system balance and provide improved performance and device robustness across a range of elevations (altitudes) and/or across a range of urine $pO_2$ values. According to certain embodiments, the balloons described herein can advantageously be configured to elastically expand through large ranges of pressure and a large number of cycles between such ranges of pressure. In this manner, an advantage of such embodiments is that if a patient travels from, for example, sea level to a high elevation and then returns back sea level, the balloon advantageously remains elastic and does not plastically deform when the patient returns to sea level.

The oxygen concentration in bodily fluids, unlike the concentration of nitrogen, is relatively complex, since oxygen is actively metabolized in the body. An aspect of this disclosure is the recognition that the concentration of oxygen can vary significantly within the body. The amount of oxygen present in blood varies and is reported as "oxygen saturation," or the % of the maximum oxygen that blood can carry or the oxygen tension $pO_2$. For a healthy person, this is typically in the range of 95 to 98%. Venous blood is typically in the range of 60 to 80%. When considering the diffusion of oxygen across membranes the preferred measurement is the oxygen tension or $pO_2$. Oxygen concentration in fluids such as cerebrospinal fluid, vitreous humor and bladder urine also varies. The partial pressure of oxygen in the urine is generally about 54-120 cm $H_2O$.

Turning, once again, to equation 8, shown below, the forces that can impact balloon volume include, but are not necessarily limited to balloon skin tension (which, as discussed herein, depends on or is a function of balloon volume), average detrusor pressure, and the partial pressure of dissolved gases in the bladder.

$$P_{PFC}=P_{Bladder-avg}+P_{Skin-tension}-P_{Dissolved\ gas} \qquad (8)$$

Where:

$P_{PFC}$=The vapor pressure of the PFC.

$P_{Bladder-avg}$=The average bladder pressure over time (i.e., course of a day) or more generally, the anatomical environment/hydrostatic average. This can be approximated as the average detrusor pressure, which, in a normal or healthy bladder is between about 6 to 15 cm $H_2O$.

$P_{dissolved-gases}$=The total gas tension of bladder urine. As discussed herein, nitrogen is not metabolized by the body and can be ignored in the above equation because the partial pressure of nitrogen in the atmosphere can be assumed to be approximately equal to the partial pressure of nitrogen in the body, including in the urine within the body. In much the same way, as the other gases in atmospheric air comprise only about 1% of the air, they can be ignored as imparting only a negligible effect. However, unlike nitrogen, oxygen is metabolized by the body. And, unlike the other gases in atmospheric air, e.g., the 1%, oxygen comprises a comparatively large percentage of the air. Therefore, the differential between the body's partial pressure of oxygen, e.g., oxygen saturation, and the atmospheric partial pressure of oxygen cannot be neglected as negligible. Therefore, the partial pressure of dissolved gases can be approximated as the partial pressure deficit of oxygen. The partial pressure of oxygen in the urine is normally about 54-120 cm $H_2O$ and the partial pressure of oxygen in the atmosphere is normally about 216 cm $H_2O$; consequently an approximate partial pressure deficit of oxygen is about 100 cm $H_2O$.

$P_{skin\ tension}$=The inward force exerted by the skin of the balloon.

Figure 15:
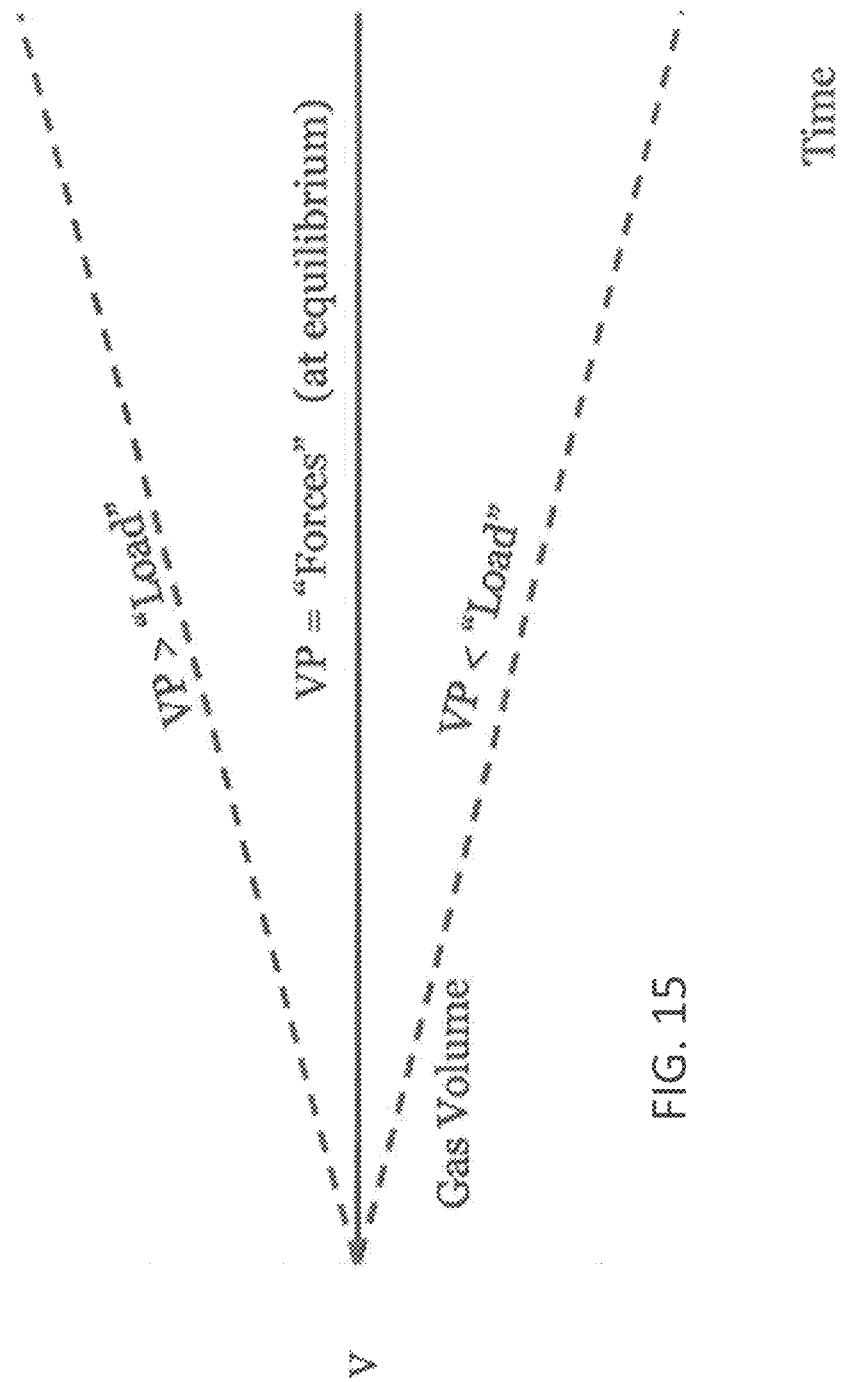
FIG. 15 shows a graph of gas volume versus time for potential balloon loading scenarios.

FIG. 15 illustrates a simplified graph of gas volume versus time for potential balloon loading scenarios (e.g., three different ratios of total internal loads to total external loads). The middle, solid line, represents a balloon having a total internal vapor pressure that is equal to the total external forces. When the total external loads are equal to the total internal loads, the balloon with neither shrink nor expand, e.g., the gas volume remains constant because the balloon is at equilibrium. The lower dashed line represents a balloon having a total internal vapor pressure that is less than the total external forces. When the total external loads on the balloon are greater than the total internal vapor pressure, the gas volume of the balloon will decrease over time. Finally, the upper dashed line represents a balloon having a total internal vapor pressure that is greater than the total external forces. When the total external loads on the balloon are less than the total internal vapor pressure, the gas volume of the balloon will increase over time.

The vapor pressure of the gases contained within the balloon, e.g., PFC, relative to the "load" exerted on the gas in the balloon determines the stability of the balloon's volume. As applied to a balloon implanted within the body, e.g., within the bladder, maintaining a substantially constant volume can be desirable. As discussed herein, increasing volume of the balloon can sometimes be undesirable. For example, overly increasing the balloon volume can compromise the balloon, causing it to become unstable, plastically deform, and experience other, undesirable, effects. In much the same way, decreasing the volume can cause be undesirable under certain circumstances. For example, overly decreasing the balloon volume can decrease the attenuating effects of the balloon and can allow the underinflated balloon to settle in the trigone region of the bladder, causing discomfort to the patient, among other, undesirable, effects.

One or more environmental conditions can affect the force balance of Equation (8) and, consequently, the performance of an implanted balloon. For example, the partial pressure of oxygen in the atmosphere is elevation dependent. High elevations can have a number of effects on a pressure attenuation device. For example, a pressure attenuation device could expand comparatively rapidly when exposed to increasingly elevation. Expansion can be due, among other things, to the wall of the balloon being too weak to limit growth of the device. As the wall of the inflatable implant expands, it can thin, e.g., it can thin significantly. Thinning of the membrane wall can compromise the integrity of the balloon. For example, when the membrane wall is thinned sufficiently it can lose its ability to elastically deform and can plastically deform. Plastic deformation of the balloon can deleteriously affect the ability of the device to attenuate transient pressure waves. The thinning of the membrane can increase the permeability of the membrane to both gas and liquid, resulting in the increased exchange or loss of gas and/or liquid, potentially reducing the stability of the balloon or the longevity of the balloon in a patient. Furthermore, at higher elevations, increasing volumes of air components can be "pulled" out of the inflatable implant, leaving the PFC. In this case, when more than one PFC is used (e.g., when, as discussed herein, more than one PFC is used to "tailor" (i.e. "program", "determine", or "set") the vapor pressure), the higher vapor pressure component(s) will be lost at a higher rate than the lower vapor pressure components(s). One or more of these factors can contribute to reduction in implant volume, which can correspond to decreased efficacy.

As discussed herein, the partial pressure oxygen deficit is dependent on the partial pressure of oxygen in the atmosphere. Therefore, Equation (8) is dependent on elevation. While small elevational changes can have only negligible effects on Equation (8) and balloon performance, large elevational changes can have more serious consequences. Consider the following elevational data provided for sea level, 5000 ft high elevation, and on an airplane.

| Location | Sea Level | High Elevation | Airplane |
|---|---|---|---|
| Elevation | 0 ft | 5000 ft | 8000 ft |
| Atmospheric Pressure | 1030.0 cm $H_2O$ | 888.5 cm $H_2O$ | 792.5 cm $H_2O$ |
| $pN_2$ 79% | 813.7 cm $H_2O$ | 701.9 cm $H_2O$ | 626.1 cm $H_2O$ |
| $pO_2$ 21% | 216.3 cm $H_2O$ | 186.6 cm $H_2O$ | 166.4 cm $H_2O$ |

As can be seen, the partial pressure of oxygen at 5000 ft high elevation is 29.7 cm $H_{high\ elevation}$ O less than the partial pressure of oxygen at sea level. And, the partial pressure of oxygen in an airplane at 8000 ft is 49.9 cm $H_2O$ less than the partial pressure of oxygen at sea level.

Based on Equation (8), to achieve equilibrium at 5000 ft high elevation, either the external forces on the balloon must be increased or the internal forces (e.g., the internal vapor pressure) must be decreased. In some situations, a gas and/or liquid having a lower vapor pressure when implanting the device, e.g., for a resident living at 5000 ft. high elevation.

Changing the vapor pressure of the gases internal to the balloon can leave the balloon appropriate for higher elevations, but inappropriate for lower elevations, such as sea level (e.g., the balloon can impermissibly shrink because of the increased pressures at sea level). In some embodiments, should the balloon pressure become less than 0, the balloon can lodge into the trigone area of the bladder and become an irritant and negatively impact the patients ability to tolerate the balloon.

Beyond the variabilities that elevation increase can impose on the inflatable implants disclosed herein, one aspect of the present disclosure is that the partial pressure of oxygen in the urine, e.g., the $pO_2$ deficit, can contribute to system variability. The $pO_2$ of urine provided herein is, for simplicity's sake, frequently stated as 116 cm $H_2O$. However, the literature reports that, due to numerous factors (e.g., environmental and/or physiological factors, among others) the partial pressure of oxygen in the urine ranges from about 50 to about 120 cm $H_2O$. Some factors that can change, e.g., increase or decrease, the partial pressure of oxygen in the urine include: hydration, diet, kidney function, general health, and acute elevation changes. For example, air travel from seal level can increase the deficient partial pressure imbalance of oxygen by about 22 cm $H_2O$ after about 6 hours at elevation due to the change in partial pressure of oxygen in the atmosphere. Therefore, a pressure attenuation device that can adapt or compensate for variations, e.g., minor variations or major variations, in the partial pressure imbalance of oxygen in the urine can be desirable. In certain embodiments of the device and balloon disclosed herein, this deficient partial pressure imbalance of oxygen due to a change of partial pressure of oxygen in the atmosphere can be addressed by programming or setting the skin tension of the balloon in a range of elevations.

Average detrusor pressure is another variable that can vary from patient to patient. As discussed herein, the walls of the bladder, through their muscle tone and mass, exert force on the urine inside, resulting in typical pressures that can be around 15 cm $H_2O$ greater than atmospheric in some patients. And, for the sake of simplifying discussion, that value is used herein as a rough approximation of average bladder pressure. However, average detrusor pressure can vary. For example, in some patients the average detrusor pressure can be 20 cm $H_2O$, 19 cm $H_2O$, 18 cm $H_2O$, 17 cm $H_2O$, 16 cm $H_2O$, 15 cm $H_2O$, 14 cm $H_2O$, 13 cm $H_2O$, 12, 11 cm $H_2O$, 10 cm $H_2O$, 9 cm $H_2O$, 8 cm $H_2O$, 7 cm $H_2O$, 6 cm $H_2O$, 5 cm $H_2O$, or 4 cm $H_2O$.

In light of the above, an improved pressure attenuation device and/or balloon according to embodiments of the present disclosure can have balloon skin tension and balloon vapor pressure sufficient to meet a sufficient range of the variable conditions described above. For example, Table 7, below shows characteristics of a balloon (e.g., skin tension and balloon vapor pressure) according to certain embodiments that would be sufficient for the lower and upper values, e.g., average or reasonable lower and upper values, of elevation, $pO_2$, and average detrusor pressure of a wide range of conditions.

media may be, for example, one or more liquid perfluorocarbons (PFCs), preferably one or more liquid PFCs having a vapor pressure greater than 50 Pa. The one or more liquid PFCs may comprise a perfluorinated heptane, a perfluorinated octane, or one or more combinations thereof. In certain embodiments, the one or more liquid PFCs are a mixture of perfluoroheptane and perfluorooctane. In some embodiments, in addition to the high vapor pressure media, the inflation media can include other gasses in addition to the high vapor pressure media such as air, nitrogen, oxygen, argon, hydrogen, oxygen, helium, carbon dioxide, neon, krypton, xenon, radon, and etc. In certain embodiments, the high vapor pressure media inside the balloon, e.g., the PFC, can be increased, the permeability of the balloon can be decreased to slow intra-day volume changes, and/or the pressure/volume relationship of the balloon can be changed via skin tension. In some embodiments, the high vapor pressure media inside the balloon, e.g., the PFC, can have vapor pressure from 155-185 cm $H_2O$ in one embodiment, from 155-175 cm $H_2O$, in another embodiment, from 155-165 cm $H_2O$ in another embodiment and from 157-163 cm $H_2O$ in another embodiment 160 cm $H_2O$ in another embodiment 151-165 cm $H_2O$. The vapor pressure values discussed and claimed herein are gauge pressures measured at sea level at a temperature of 37° C. In some embodiments, the ranges of the vapor pressure of the high vapor pressure

TABLE 7

Representative Pressure Attenuation Device Operating Ranges

| External Loads | Sea Level Low $pO_2$ Urine | Sea Level High $pO_2$ Urine | 5000 ft High $pO_2$ Urine | Airplane High $pO_2$ Urine |
|---|---|---|---|---|
| $PO_2$ ATM | 216 cm $H_2O$ | 216 cm $H_2O$ | 186 cm $H_2O$ | 166 cm $H_2O$ |
| $PO_2$ Urine | 80 cm $H_2O$ | 100 cm $H_2O$ | 100 cm $H_2O$ | 115 cm $H_2O$ |
| → $PO_2$ Deficit | 136 cm $H_2O$ | 116 cm $H_2O$ | 86 cm $H_2O$ | 51 cm $H_2O$ |
| $P_{Bladder-avg}$ | 15 cm $H_2O$ | 6 cm $H_2O$ | 6 cm $H_2O$ | 6 cm $H_2O$ |
| Skin Tension of balloon | 9 cm $H_2O$ | 38 cm $H_2O$ | 68 cm $H_2O$ | 103 cm $H_2O$ |
| Tot. External Internal Pressure | 160 cm $H_2O$ | 160 cm $H_2O$ | 160 cm $H_2O$ | 160 cm $H_2O$ |
| Vapor Pressure of Pfc? | 160 cm $H_2O$ | 160 cm $H_2O$ | 160 cm $H_2O$ | 160 cm $H_2O$ |
| Total Internal | 160 cm $H_2O$ | 160 cm $H_2O$ | 160 cm $H_2O$ | 160 cm $H_2O$ |
| Total. Combined | 0 cm $H_2O$ (equilibrium) | 0 cm $H_2O$ (equilibrium) | 0 cm $H_2O$ (equilibrium) | 0 cm $H_2O$ (equilibrium) |

Ranging from seal level low urine $pO_2$ to airplane high urine $pO_2$, the total environmental load on the implant, including the average detrusor pressure and the $PO_2$ deficit ranges from about 57 cm $H_2O$ to about 151 cm $H_2O$. In situations where 120 cm $H_2O$ PFC is used, the balloon could deflate when the patient is at sea level with or without low $PO_2$. As will be explained below, increased vapor pressure can be used to create higher skin tensions which can advantageously allow the balloon to remain inflated at sea level.

Various modifications to the pressure attenuation devices disclosed herein can be made to account for or compensate for both patient and environmental variabilities. For example, the balloon may be inflated with an inflation media. The inflation media may include a fluid at body temperature (37 degrees Celsius) and in certain embodiments the fluid may be one or more high vapor pressure media that may serve as a pressure regulator to help keep device 17 inflated. The one or more high vapor pressure media inside the balloon described in this paragraph can be combined with the ranges, values and/or features of the balloon described herein such the natural balloon volume, percent increases in volume when the pressure within the balloon is increased a certain amount, wall thickness of the balloon, and/or the elastic deformation range of the balloon. Advantageously, vapor pressures within these ranges can be used to create higher skin tensions which can advantageously allow the balloon to remain inflated at sea level.

Figure 16:
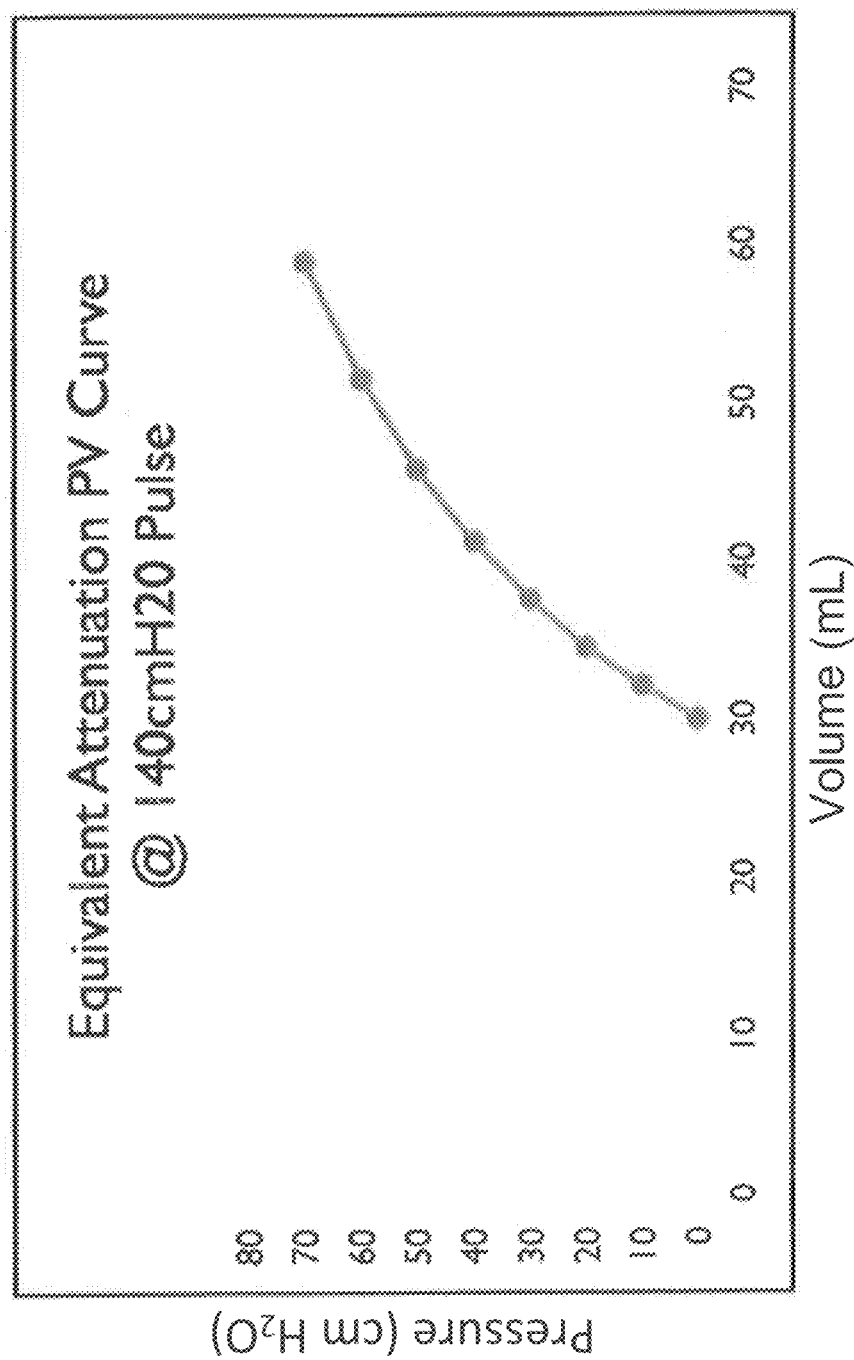
FIG. 16 shows an attenuation PV curve for an embodiment of pressure attenuation device.

FIG. 16 shows the equivalent attenuation PV curve, e.g., pressure versus volume, for an embodiment of an embodiment of a pressure attenuation device subjected a 140 cm $H_2O$ pulse. As illustrated, a pressure attenuation device can achieve an equivalent attenuation at higher internal pressures if the volume of the pressure attenuation device is increased at the high internal pressures. According, in certain embodiments, the volume of the balloon of the pressure attenuation device advantageously increases with increasing internal pressure.

As noted above, the high vapor pressure media within the balloon can be formed of various components having the desired vapor pressures. In one embodiment it can comprise one or more PFCs that can be combined to form a liquid mixture with a particular vapor pressure according to their mole fraction in the liquid. The one or more liquid PFCs may comprise a perfluorinated heptane, a perfluorinated octane, or one or more combinations thereof. The one or more liquid PFCs can be a mixture of perfluoroheptane and perfluorooctane. For example, in some embodiments a mixture of about 0.193 mole perfluorooctane and about 0.807 mole perfluoroheptane can result in a vapor pressure of around 160 cm $H_2O$ at 37° C. In another example, a mixture of about 0.1 mole perfluorooctane and 0.9 mole perfluoroheptane can result in a vapor pressure of about 170 cm $H_2O$. In some embodiments, the balloon can be inflated with and/or also contain other gasses in addition to the high vapor pressure media such as air, nitrogen, oxygen, argon, hydrogen, helium, carbon dioxide, neon, krypton, xenon, radon, and etc.

FIG. 14, which was discussed above, shows an example balloon internal pressure versus balloon volume curve. Balloon internal pressure versus balloon volume curves (P/V) can be useful to characterize the performance of attenuating balloons. As shown by region A in FIG. 14, balloon P/V curves generally begin with an initial, relatively horizontally flat region where the balloon is in a "bag" like state. The initial flat region corresponds to the initial filling of the balloon before the wall of the balloon begins to apply any load to the fluids inside the balloon. As shown by region B in FIG. 14, the point at which the initial flat region increases sharply corresponds to the balloon's initial volume or natural volume. The pressure increases rapidly after the initial volume because that is the point at which the balloon wall begins to impart a load, e.g., the load imparted by the balloon wall changes from effectively zero to a positive value. As shown by region C in FIG. 14, after reaching their initial volume, the balloons continue to grow in volume. Because the balloon wall is applying inward forces on the fluids within the balloon, the pressures increase relatively quickly after the initial volume has been exceeded. Depending on the characteristics of the balloon, including thickness, stiffness, balloon shape, balloon volume, etc., the balloon will have a range of volumes in which its wall changes size elastically without plastic deformation. Elastic deformation allows the balloon to shrink, elastically, if the pressure decreases. As shown by region C in FIG. 14, the elastic region of the curves has a relatively constant slope, e.g., the slope does not vary significantly from a given value. Most materials have a finite amount of elastic deformation after which they deform plastically, e.g., they do not regain (e.g., fully regain), their original shape after the deforming force is removed. As shown by region D in FIG. 14, the beginning of the plastic deformation region is frequently where the slope of the line changes markedly and remains substantially constant. After the plastic region is reached, the balloon will likely fail to shrink once the deforming force is removed. An aspect of the present disclosure is the recognition that plastic deformation is generally undesirable in the context of inflatable pressure attenuators, whereas elastic deformation is generally desirable in the same context.

Operating within an elastic deformation range can be desirable for a pressure attenuation device. This is because elastic deformation allows the implant to adapt to increased forces, whether inside the balloon or outside the balloon, then regain its original configuration after the forces decrease to their original levels. Therefore, the elastic region can be considered to encompass the device's operating range. Balloon embodiments having elastic regions encompassing larger ranges of volumes and larger pressures may be desirable as such balloons may be able to withstand a broader range of environmental changes.

Figure 17:
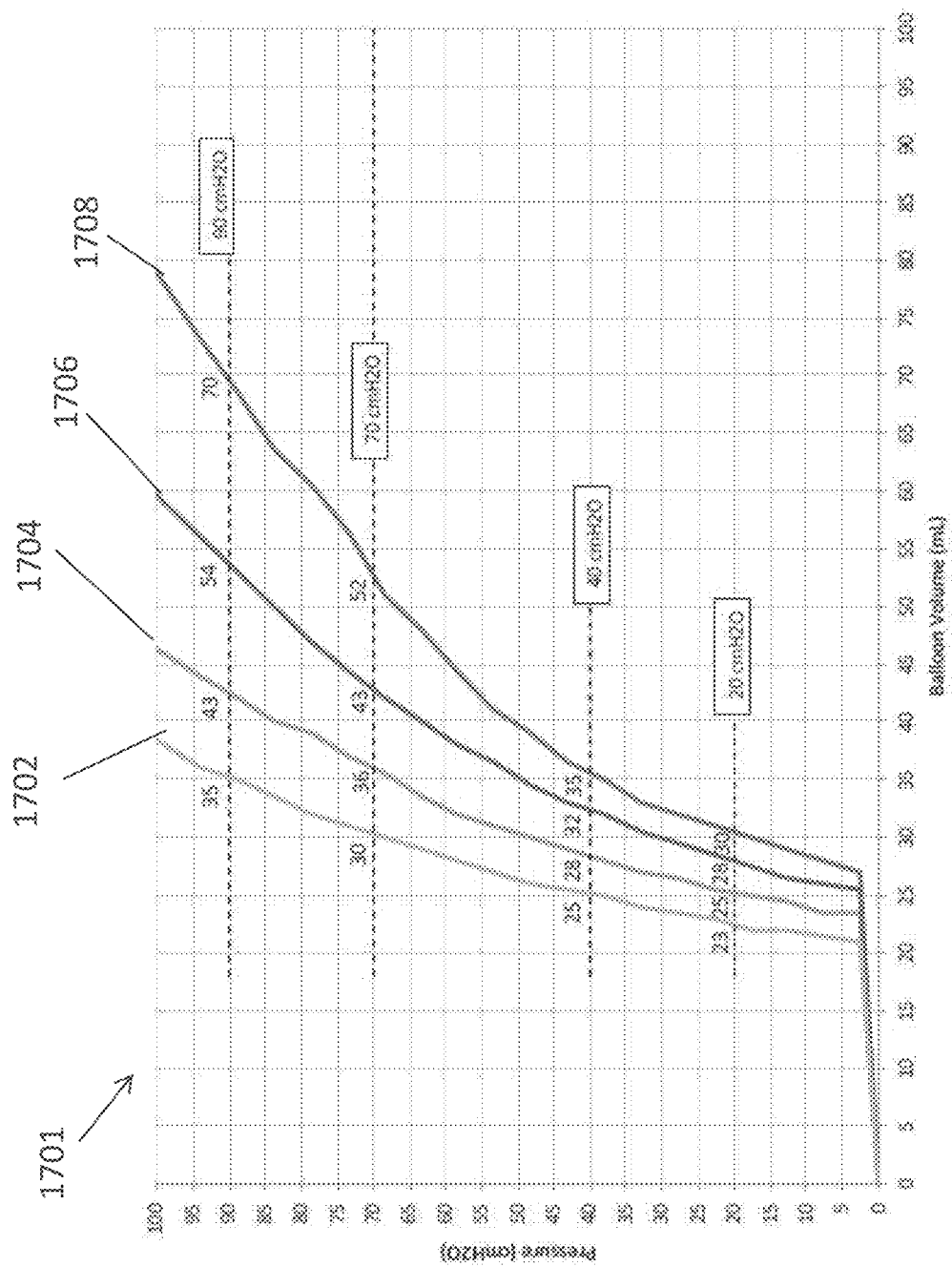
FIG. 17 illustrates P/V curves and elasticity of the balloon according certain embodiments of a pressure attenuation devices.

Balloon P/V curves may be characterized, at least partially, by the percentage of volumetric change for a given change in internal pressure within the balloon. For example, certain balloon embodiments increase by some non-zero volume (by comparison to its natural volume) when the pressure within the balloon is increased from 2.5 cm $H_2O$, e.g., transition from a bag to the balloon's natural volume, to a greater pressure. FIG. 17 illustrates P/V curves 1701 of embodiments of a balloon according certain embodiments of the pressure attenuation devices. Curve 1 1702, curve 1704, curve 1706, and curve 1708 represent different embodiments of balloons that can remain elastic between internal pressures of 2.5 cm $H_2O$ to at least 90 cm $H_2O$ and can have P/V curves according to certain embodiments. In addition, the balloons according to these embodiments can be inflated with a high vapor pressure media within the pressure ranges described herein. The balloon pressures discussed herein and also claimed (also referred to as "internal pressure" or "internal balloon pressure" or "pressure within the balloon" are gauge pressures measured at sea level at a temperature of 37° C.

With reference to FIG. 17, in some embodiments, of a pressure attenuation device, the balloon increases in volume when the internal pressure within the balloon is increased from 2.5 cm $H_2O$ to 15 cm $H_2O$ by less than 10%, less than 9.5%, less than 8%, less than 7%, less than 5.5%, or less than 4%. In some embodiments, the balloon increases in volume when the internal pressure within the balloon is increased from 2.5 cm $H_2O$ to 15 cm $H_2O$ by between 3-10%, between 4.0-9.5%, between 4.5-8%, between 4.5-7.0% or about 5%. Within these ranges, the balloon preferably elastically expands and does not plastically deform. In certain embodiments, within these ranges, the balloon can elastically expand between 2.5 to 15 cm $H_2O$ for at least 15 cycles, 25 cycles, 50 cycles, 100 cycles, or greater. In certain embodiments, these ranges of percent increases in volume when the internal pressure within the balloon is increased a certain amount, can be combined with the ranges of vapor pressures for the high vapor pressure media inside the balloon described above, the values and/or features of the balloon described below such as the natural balloon volume, wall thickness of the balloon, and/or the elastic deformation range of the balloon.

In some embodiments, the balloon increases in volume when the internal pressure within the balloon is increased from 2.5 cm $H_2O$ to 20 cm $H_2O$ by less than 15%, less than 13%, less than 12%, less than 11%, less than 10%, less 8%, less than 6%, or less than 5%. In some embodiments, the balloon increases in volume when the internal pressure within the balloon is increased from 2.5 cm $H_2O$ to 20 cm $H_2O$ by between 4-13%, between 5-12.%, between 6-11%, between 6.5-10% or between 6.5 and 8%. Within these ranges, the balloon preferably elastically expands and does not plastically deform. In certain embodiments, within these ranges, the balloon can elastically expand between 2.5 to 20 cm $H_2O$ for at least 15 cycles, 25 cycles, 50 cycles, 100 cycles, or greater. In certain embodiments, these ranges of percent increases in volume when the internal pressure within the balloon is increased a certain amount, can be combined with the ranges the vapor pressures for the high vapor pressure inside the balloon described above, the values and/or features of the balloon described herein such as additional ranges of percent increases in volume when the pressure within the balloon is increased a certain amount, the natural balloon volume, wall thickness of the balloon, and/or the elastic deformation range of the balloon.

In some embodiments, the balloon increases in volume when the internal pressure within the balloon is increased from 2.5 cm $H_2O$ to 30 cm $H_2O$ by less than 25%, less than 22.5%, less than 19%, less than 16%, less than 12%, or less than 11%. In some embodiments, the balloon increases in volume when the internal pressure within the balloon is increased from 2.5 cm $H_2O$ to 30 cm $H_2O$ by between 10-25%, between 11-22.5%, between 12-19 cm $H_2O$, or between 13-16 cm $H_2O$. In certain embodiments, within these ranges, the balloon can elastically expand between 2.5 to 30 cm $H_2O$ for at least 15 cycles, 25 cycles, 50 cycles, or 100 cycles. Within these ranges, the balloon preferably elastically expands and does not plastically deform. In certain embodiments, within these ranges, the balloon can elastically expand between 2.5 to 30 cm $H_2O$ for at least 15 cycles, 25 cycles, 50 cycles, 100 cycles, or greater. In certain embodiments, these ranges of percent increases in volume when the internal pressure within the balloon is increased a certain amount, can be combined with the ranges of vapor pressures for the high vapor pressure media inside the balloon described above, the values and/or features of the balloon described herein such as additional ranges of percent increases in volume when the pressure within the balloon is increased a certain amount, the natural balloon volume, wall thickness of the balloon, and/or the elastic deformation range of the balloon.

In some embodiments, the balloon increases in volume when the internal pressure within the balloon is increased from 2.5 cm $H_2O$ to 40 cm $H_2O$ by less than 45%, less than 40%, less than 30%, less than 27%, less than 19%, or less than 15%. In some embodiments, the balloon increases in volume when the internal pressure within the balloon is increased from 2.5 cm $H_2O$ to 40 cm $H_2O$ by between 10-45%, between 15-40%, between 18-30%, or between 19-27%. Within these ranges, the balloon preferably elastically expands and does not plastically deform. In certain embodiments, within these ranges, the balloon can elastically expand between 2.5 to 40 cm $H_2O$ for at least 15 cycles, 25 cycles, 50 cycles, 100 cycles, or greater. In certain embodiments, these ranges of percent increases in volume when the internal pressure within the balloon is increased a certain amount, can be combined with the ranges vapor pressures for the high vapor pressure media inside the balloon described above, the values and/or features of the balloon described herein such as additional ranges of percent increases in volume when the pressure within the balloon is increased a certain amount, the natural balloon volume, wall thickness of the balloon, and/or the elastic deformation range of the balloon.

In some embodiments, the balloon increases in volume when the internal pressure within the balloon is increased from 2.5 cm $H_2O$ to 70 cm $H_2O$ by less than 150%, less than 100%, less than 90%, less than 75%, less than 60%, less than 55%, less than 45%, or less than 40%. In some embodiments, the balloon increases in volume when the internal pressure within the balloon is increased from 2.5 cm $H_2O$ to 70 cm $H_2O$ by between 20-150%, between 30-100%, between 40-90%, between 40-75%, between 45-60% or between 50-55%. Within these ranges, the balloon preferably elastically expands and does not plastically deform. In certain embodiments, within these ranges, the balloon can elastically expand between 2.5 to 70 cm $H_2O$ for at least 15 cycles, 25 cycles, 50 cycles, 100 cycles, or greater. In certain embodiments, these ranges of percent increases in volume when the pressure within the balloon is increased a certain amount, can be combined with the ranges of vapor pressures for the high vapor pressure media inside the balloon described above, the values and/or features of the balloon described herein such as additional ranges of percent increases in volume when the pressure within the balloon is increased a certain amount, the natural balloon volume, wall thickness of the balloon, and/or the elastic deformation range of the balloon.

In some embodiments, the balloon increases in volume when the internal pressure within the balloon is increased from 2.5 cm $H_2O$ to 90 cm $H_2O$ by less than 190%, less than 100%, less than 90%, or less than 85%, less than 70%. In some embodiments, the balloon increases in volume when the internal pressure within the balloon is increased from 2.5 cm $H_2O$ to 90 cm $H_2O$ by at least 10% but less than 90%, or by between 50-190%, between 60-150%, between 65-100%, between 75-90% or between 80-85%. Within these ranges, the balloon preferably elastically expands and does not plastically deform. In certain embodiments, within these ranges, the balloon can elastically expand between 2.5 to 90 cm $H_2O$ for at least 15 cycles, 25 cycles, 50 cycles, or 100 cycles or greater. In certain embodiments, these ranges of percent increases in volume when the pressure within the balloon is increased a certain amount, can be combined with the ranges vapor pressures for the high vapor pressure media inside the balloon described above, the values and/or features of the balloon described herein such as additional ranges of percent increases in volume when the pressure within the balloon is increased a certain amount, the natural balloon volume, wall thickness of the balloon, and/or the elastic deformation range of the balloon.

In certain embodiments, the balloon for the pressure attenuation device for the bladder may be characterized by their ability to inflate, stay below a certain volume, withstand certain pressures, and withstand certain pressure changes while remaining elastically deformable, all while appropriately attenuating the transient pressure event, as discussed elsewhere herein.

As discussed herein, bag-like inflatable implants, e.g., implants below their natural volume, can be undesirable due to their potentially low tolerability. The balloons of certain embodiments the pressure attenuation devices disclosed herein will have varying volumes based on the balance of forces, e.g., internal forces vs. external forces. The range of volumes may be bounded by the balloon natural volume on the lower end (as volumes below the natural volume, in which the implant is "bag-like" may be undesirable) and bounded by the inflatable implant's maximum volume on the upper end.

In some embodiments, the balloon of the pressure attenuation device of the embodiments described above, has a natural volume in certain embodiments of between 0.1 and 500 cc, in certain embodiments between 1 and 180 cc, in certain embodiment, between 10 and 60 cc. In certain embodiments, the balloon has a natural volume of between 25-30 ml, between 20-35 ml, between 22.5-32.5 ml, or 27 ml. In certain embodiments, these ranges of natural volume can be combined with the percent increases in volume when the internal pressure within the balloon is increased a certain amount and/or the ranges of vapor pressure of the high vapor pressure media described above and/or the wall thickness of the balloon, and/or the elastic deformation ranges of the balloon embodiments described herein. It is also anticipated that in certain embodiments, more than one pressure attenuation device can be used within the bladder and/or pressure attenuation device with more than one balloon can be used within the bladder. In such embodiments, the total volume of the more than one pressure attenuation device and/or more than one balloon can be within the natural volume ranges described above.

In certain embodiments, the maximum volume of the balloon of the pressure attenuation device, advantageously is no more than 10% of the volume of the patient's bladder. This is because if the device gets too large, it can occupy too much of the volume of the bladder and diminish its capacity to the point where the patient will need to urinate more frequently. In some embodiments, the maximum volume of the balloon compared to the volume of the patient's bladder should be less than 50%, less than 45%, less than 40%, less than 35%, less than 30%, less than 25%, less than 20%, less than 15%, less than 10%, or less than 5%. The volume of an adult bladder is 400-600 ml. Therefore, absolute volumes may be determined by taking the disclosed percentage of 400-600 ml. For example, in an embodiment in which the balloon's maximum volume is less than 10%, the absolute maximum volume of the balloon is between 40-60 ml.

Balloon maximum value may be a function of several discussed variables, including, but not limited to, partial pressure of oxygen in the urine, balloon internal vapor pressure, elevation, etc. However, the balloons maximum volume should be independent of the balloon's natural volume. That is to say, that regardless of the initial, natural volume of the balloon advantageously does exceed the maximum volume value. This is because it can be undesirable for the balloon to occupy over a certain threshold of the bladder's volume due to commensurate decreases in the bladder's functional capacity. For example, given a maximum volume of 50 ml: a balloon having a natural volume of 10 ml could in certain embodiments have a maximum operating range of a 10-50 ml; a balloon having a natural volume of 20 ml could in certain embodiment have a maximum operating range of 20-50 ml, a balloon having a natural volume of 30 ml could have in certain embodiments a maximum operating range of 30-50 ml; etc.

Certain embodiments of the balloon 1711, 68 discussed herein are able to withstand internal pressures of at least 90 cm $H_2O$ without plastically deforming. In certain embodiments, the balloon 1711, 68 is able to withstand internal pressures of at least 100 cm $H_2O$ without plastically deforming. In certain embodiments, the balloon 1711, 68 is able to withstand internal pressures of at least 110 cm $H_2O$ without plastically deforming. In certain embodiments, the balloon 1711, 68 is able to withstand internal pressures of at least 120 cm $H_2O$ without plastically deforming.

In certain embodiments, the balloon can elastically deform when the internal pressure within the balloon is increased from 0 cm $H_2O$-90 cm $H_2O$, from 0 cm $H_2O$ to 100 cm $H_2O$, and/or from 0 cm $H_2O$-120 cm $H_2O$. Within these ranges, the balloon can elastically deform for at least 1 cycle, for at least 5 cycles, 25 cycles, 50 cycles, 100 cycles or greater between the maximum and minimum pressure within these ranges. In certain embodiments, these ranges wherein the balloon can elastically deform can be combined with the ranges of percent increases in volume when the pressure within the balloon is increased a certain amount described above and/or can be combined with the ranges of vapor pressures for the high vapor pressure media inside the balloon described above, the values and/or features of the balloon described herein such as the natural balloon volume, and/or the wall thickness of the balloon.

In certain embodiments, when the internal pressure within the balloon is increased from 0 cm $H_2O$ to 90 cm $H_2O$, from 0 cm $H_2O$ to 100 cm $H_2O$, and/or from 0 cm $H_2O$ to 120 cm $H_2O$ for at least 1 cycle, for at least 5 cycles, 25 cycles, 50 cycles, 100 cycles or greater between the maximum and minimum pressure within these ranges the volume of the balloon for a given internal pressure changes within +/−1%, +/−5%, and/or +/−10%. In certain embodiments, these ranges wherein the volume of the balloon remains remain within a certain range for a given pressure can be combined with the ranges of percent increases in volume when the pressure within the balloon is increased a certain amount described above and/or can be combined with the ranges vapor pressures for the high vapor pressure media inside the balloon described above, the values and/or features of the balloon described herein such as the natural balloon volume, and/or the wall thickness of the balloon The ability to withstand a given internal pressure without plastically deforming may be a function of how long the balloon is subjected to the increased internal pressure. In some embodiments, the balloon is able to withstand the pressures disclosed herein without plastic deformation for about 6 hours. In some embodiments, the inflatable implant is able to withstand the pressures disclosed herein without plastic deformation for at least 12 hours, 24, hours, 36 hours, 48 hours, 60 hours, or 72 hours. In some embodiments, the inflatable implant is able to withstand the pressures disclosed herein without plastic deformation for at least 1 week, at least 2 weeks, at least 3 weeks, or at least 4 weeks. In some embodiments, the balloon is able to withstand the pressures disclosed herein without plastic deformation (for at least 2 months, at least 3 months, at least 4 months, at least 5 months, at least 6 months, at least 1 year, at least 2 years, or at least 3 years. In some embodiments, the balloon remains elastic through the ranges discussed herein at after 15, 25, 50, or 100 cycles.

In some embodiments, balloons falling within the P/V performance parameters and/or plastic deformation disclosed herein also have an increased internal vapor pressure offset by an increased skin tension, e.g., due to an increased thickness or other material property(ies). In some embodiments, the balloon's internal vapor pressure is greater than 150 cm $H_2O$. In some embodiments, the balloon's internal vapor pressure is great than 155 cm $H_2O$, greater than 160 cm $H_2O$, greater than 165 cm $H_2O$, greater than 170 cm $H_2O$, or greater than 175 cm $H_2O$. In some embodiments, the balloon/s internal vapor pressure is between 155-185 cm $H_2O$. In some embodiments, the balloon's internal vapor pressure is between 155-175 cm $H_2O$, between 155-165 cm $H_2O$, or between 157-163 cm $H_2O$, and in another embodiment about 160 cm $H_2O$.

The tables below, table 8(A) and 8(B), show the volume and percent change in volume for various representative balloon embodiments (1), (2), (3), (4), (5), and (6) which are also illustrated in FIG. 17.

TABLE 8(A)

Volume for Balloon Embodiments at Set Pressures

| Pressure (cm $H_2O$) | (1) | (2) | (3) | (4) | (5) | (6) |
|---|---|---|---|---|---|---|
| 2.5 | 27 ml | 25.5 ml | 23.5 ml | 21 ml | 27.5 ml | 25 ml |
| 15 | 29.5 ml | 27 ml | 24.75 ml | 22 ml | 29.4 ml | 26.5 ml |
| 20 | 30 ml | 28 ml | 25.25 ml | 22.5 ml | 30 ml | 27 ml |
| 30 | 32.5 ml | 30 ml | 26.75 ml | 23.75 ml | 31.5 ml | 29.5 ml |
| 40 | 36 ml | 32.5 ml | 29.4 ml | 25.25 ml | 33.5 ml | 30 ml |
| 70 | 52 ml | 43 ml | 36 ml | 31.25 ml | 42 ml | 36 ml |
| 90 | 70 ml | 54 ml | 43 ml | 35.5 ml | 51 ml | 42 ml |

TABLE 8(B)

% Volume Change Compared to Initial Volume at 2.5 cm $H_2O$

| Pressure (cm $H_2O$) | (1) | (2) | (3) | (4) | (5) | (6) |
|---|---|---|---|---|---|---|
| 2.5 | 0% | 0% | 0% | 0% | 0% | 0% |
| 15 | 9% | 6% | 5% | 5% | 7% | 6% |
| 20 | 11% | 10% | 7% | 7% | 9% | 8% |
| 30 | 20% | 18% | 14% | 13% | 15% | 18% |
| 40 | 33% | 27% | 25% | 20% | 22% | 20% |
| 70 | 93% | 69% | 53% | 49% | 53% | 44% |
| 90 | 159% | 112% | 83% | 69% | 85% | 68% |

In some embodiments, the balloon does not burst when its internal pressure is less than or equal to 90 cm $H_2O$, less than or equal to 70 cm $H_2O$, cm $H_2O$, less than or equal to 40 cm $H_2O$, less than or equal to 20 cm $H_2O$, or less than or equal to 10 cm $H_2O$.

In some embodiments, the inflatable balloon can also have relatively low deflection values and have high burst test pressures. Table X below provides example data of deflection and test pressures at different volumes and pressures of cm $H_2O$ for two different embodiments of a balloon of a pressure attention device (with the first 4 rows of Table X corresponding to one embodiment and the second 4 rows of the Table X corresponding to a second embodiment). The deflection and test pressures of Table X can be determined on a balloon using the test fixture and procedures described in paragraphs [0457] to [0465] and FIGS. 146-153 of U.S. Patent Publication 2015/0216644, the entirety of which is hereby incorporated by reference herein for all purposes and included in this application. As indicated in the table below, in some embodiments, the balloon can withstand a test pressure of at least 15 cm $H_2O$ and/or 20 cm $H_2O$ without bursting and/or having a minimum deflection of 6 mm or less and/or 5 mm.

TABLE X

Pressure and Test Pressure Characteristics

| Volume ml | Pressure cm $H_2O$ | Deflection mm | $B_L$ Test Pressure cm $H_2O$ | |
|---|---|---|---|---|
| 27 | 20 | 6 | 35 | no burst |
| 30 | 40 | 6 | 27 | no burst |
| 36 | 70 | 6 | 26 | no burst |
| 42 | <90 | 5 | 31.25 | no burst |
| 30 | 20 | 5 | 25 | no burst |
| 40 | 40 | 5 | 24 | no burst |
| 42 | <70 | 5 | 28 | no burst |
| 42 | <70 | 5 | 24 | no burst |

Table 9, below, provides data for three different embodiments of a balloon of an embodiment of the pressure attenuation device. Of course, while certain parameters are shown, one or more parameters may be changed. Within these parameters, the balloon preferably elastically expands and does not plastically deform.

TABLE 9

Example Balloon Characteristics

| Performance Attribute | Embodiment 1 | Embodiment 2 | Embodiment 3 |
|---|---|---|---|
| Natural Volume (room temp.) | 26 ml | 28 ml | 25-29 ml |
| Inflated Volume (room temp.) | 30 ± 2 ml | 30 ± 2 ml | |
| Wall Thickness (2×) | 0.00205-0.00325 inches | 0.00210-0.00315 inches | 0.002-0.0035 inches |
| Volume Observed at 20 cm $H_2O$ | 27 ml | 30 ml | 26-31 ml |
| Volume Observed at 70 cm $H_2O$ | 36 ml | 43 ml | 35-44 ml |
| Volume Observed at 90 cm $H_2O$ | 42 ml | 51 ml | 41-52 ml |
| Pressure Attenuation at 2 psi | 0.67-0.78 psi | 0.60-0.75 psi | 0.5-0.9 psi |
| Volume after 67 days At 140 cm $H_2O$ | 27 ml | 30 ml | 25-30 m |

Limiting Implant Expansion

In another embodiment two or more PFCs with different vapor pressures are mixed to give an average vapor pressure based on the mole fraction of the components. As the PFC mixture diffuses out of the device over time the more volatile component will diffuse proportionately to its mole fraction in the mix, therefore the mole fraction of the higher vapor pressure component will go down and the vapor pressure of the mix will likewise be reduced. This phenomenon could be used to control the ultimate size of the balloon. As the balloon expands, the vapor pressure of the PFC mix will go down placing an upper limit on balloon volume.

In some embodiments, the skin tension of the balloon could be used advantageously to limit balloon expansion. As the balloon expands, the tension of the balloon material will increase until the excess gas pressure in the balloon will be offset by the tension in the balloon skin.

In addition, just as skin geometries and other features of the implant 66 can change the V/P curve; these same or similar features can limit expansion, deflation or the rate of change of the implant.

In some embodiments, an implant has a high surface to volume ratio to affect a rapid rate of change. The implant shape can be selected from cylindrical, spiral, or ridged. In another embodiment a slow rebound or rapid inflation is desired and thus a low surface area to volume ratio is desired and a spherical design is selected.

In a further embodiment the quantity of PFC in a balloon could be used to limit expansion. A precise quantity of PFC could be added to the balloon such that as the balloon expands the PFC would volatilize to maintain its partial pressure until the PFC liquid reservoir is depleted. The PFC gas would then dilute with further expansion and the internal pressure of the balloon would be limited.

Devices described herein containing PFC and other gases can be placed into pressure equilibrium with the environment in which they are deployed. Since no natural environment is truly at constant pressure, the balloon system would need to gain external gases during low external pressure times and lose gas during high pressure times. The loss of gas would need to balance with the gain of gas for long term stability.

Delivery of Implant and Removal of Implant

As noted above, the pressure attention devices 12, 66 according to the embodiments described herein can be transurethrally deployed into the bladder in its first configuration, and enlarged to its second configuration once positioned within the bladder to accomplish a pressure attenuation function. Preferably, a crossing profile, or a greatest cross-sectional configuration, of the attenuation device 17, 66 when in the first configuration is no greater than 24 French (8 mm), and, preferably, no greater than 18 French (6 mm). This can be accomplished, for example, by rolling a deflated balloon about a longitudinal axis, while the interior chamber is evacuated. Once positioned within the bladder, the interior chamber 72 is filled with the media to produce a pressure attenuation device 17, 66. After a certain period of time, the pressure attention devices 12, 66 can be deflated and removed from the bladder.

With reference to FIGS. 18A to 26D, further embodiments of devices and methods are disclosed which can be used to insert and/or remove the pressure attention devices 12, 66 embodiments described herein. Further details for such insertion and removal devices can be found for example, in the following documents, U.S. Patent Application Publication No. US2015/0216644A1, Cahill et al., published Aug. 6, 2015 and U.S. patent application Ser. No. 16/557,555 filed Aug. 30, 2019, the entirety of these applications are all incorporated by reference herein for all purposes.

Delivery Device

The pressure attenuation devices disclosed herein may be delivered to an anatomical structure in a compacted or deflated state and, after being delivered to the anatomical structure, may be inflated and deployed. Preferably, the delivery of the device to the anatomical structure in a deflated state is accomplished by positioning device in its deflated state within a window of a catheter, with distal end of inflation tube sealed against intermediate section of valve in the manner discussed above. The balloon may be folded within catheter in a manner complementary to the shape of window so as to maximize the likelihood that device may be retained within catheter window prior to being inflated and may be released through window once inflated.

Certain embodiments of a delivery device are described in U.S. Patent Application Publication No. 2010/0222802, incorporated by reference herein. See for example: FIGS. 6-18H, and the accompanying discussion, including at paragraphs [0153]-[0206]. Embodiments of a delivery device are also provided in U.S. Pat. No. 6,976,950, incorporated by reference herein. See for example: FIGS. 6-11A, 34A-35B and 48A-48D, and the accompanying discussion, including at columns 13-16, and 35.

Figure 18A:
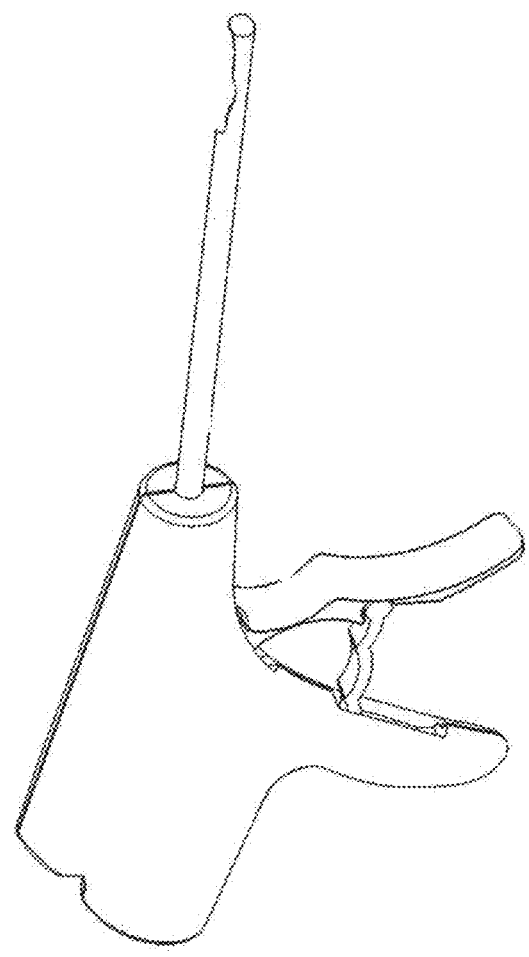
FIGS. 18A-B shows an embodiment of a delivery device that may be used to deliver a pressure-attenuating device to the target body area.
Figure 18B:
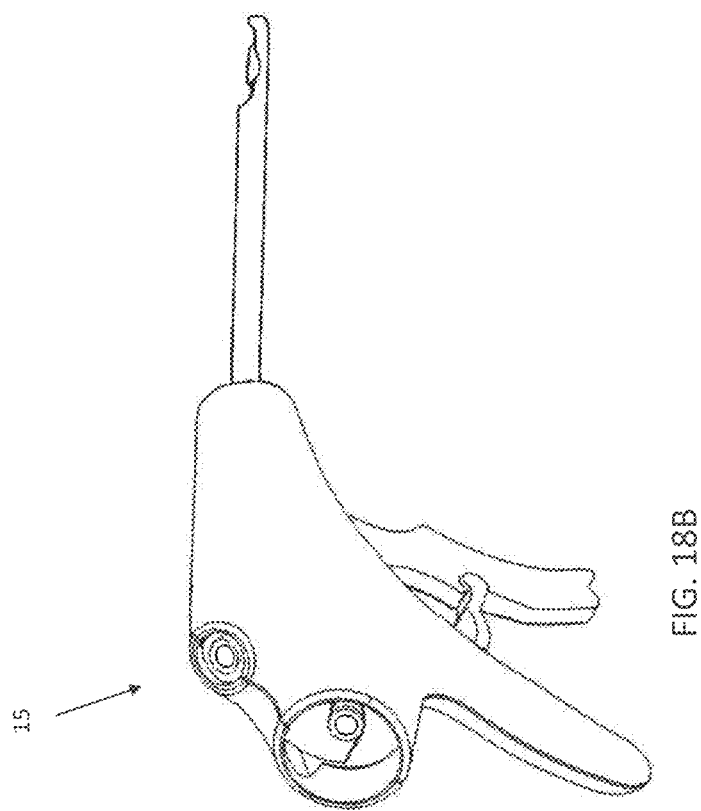

A delivery device 15 may be inserted through the passageway created by an access device. As shown in FIGS. 18A-B, the delivery device 15 may be used to deliver a pressure-attenuating device to the body, such as to the bladder. The delivery device 15 may deliver the pressure attenuation device in a compacted state which may then be inflated and released. The steps of inflation and/or release may be performed by the delivery device. The delivery device 15 can include a delivery tube, an inflation tube, a connection to inflation media and a release mechanism, among other features.

Figure 19:
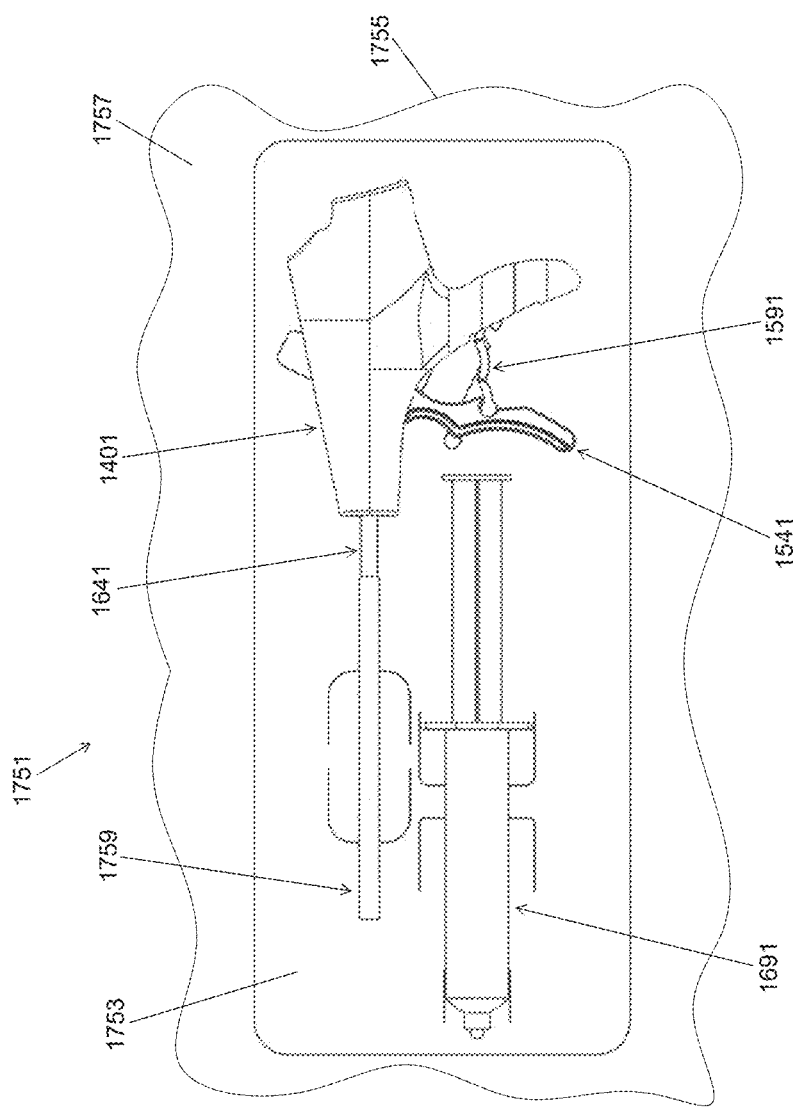
FIG. 19 shows an embodiment of a sterilizable kit comprising certain components of a delivery device.

Referring now to FIG. 19, there is shown a top view of one embodiment of a sterilizable kit comprising certain components of a delivery device 15, the sterilizable kit being represented generally by reference numeral 1751.

Kit 1751 may comprise a sheet of support material 1753, which may be a sheet of cardboard or a similarly suitable support material. Kit 1751 may further comprise a sealed pouch 1755 surrounding support material 1753, pouch 1755 defining a sealed cavity 1757. Pouch 1755 may be made of a transparent material, such as one or more transparent polymer sheets. Kit 1751 may further comprise the components of delivery device 15 nearly being fully assembled, except that an additional syringe for inflation media is not present and that syringe 1691 is not attached to the remaining components of delivery device 15. Syringe 1691 may be disposed within cavity 1757 and may be mounted on support material 1753, and the remainder of delivery device 15 may be disposed within cavity 1757 and may be mounted on support material 1753 at a distance from syringe 1691. Syringe 1691 may be opened to drawn in a volume of air corresponding to the volume of air one wishes to dispense therefrom into device 17. Although not visible in FIG. 19, kit 1751 may further comprise pressure-attenuating device 17, 66, which may be loaded within window catheter 1641 of delivery device 15 and may be coupled to inflation tube 1741 in the manner described above. Kit 1751 may further comprise a removable protective sleeve 1759, which may be inserted over catheter 1641 to ensure retention pressure-attenuating device 17 within catheter 1641 during shipping and/or storage. (Sleeve 1759 is removed from catheter 1641 prior to use; alternatively, sleeve 1759 may be replaced with cover 1703, which may be retained for use in the manner described above.) All of the components of kit 1751 are made of a material that may be sterilizable by a suitable sterilization technique, such as gamma radiation.

An advantageous feature of kit 1751 is that the air contained within syringe 1691 may become sterilized during the sterilization procedure applied to kit 1751. In this manner, one may minimize the introduction of air into pressure-attenuating device 17 that may contain undesirable microorganisms. For similar reasons, microbial filters may alternatively or additionally be appropriately positioned within fluid connector 1423 and/or check valves 1441 and 1443.

Figure 20:
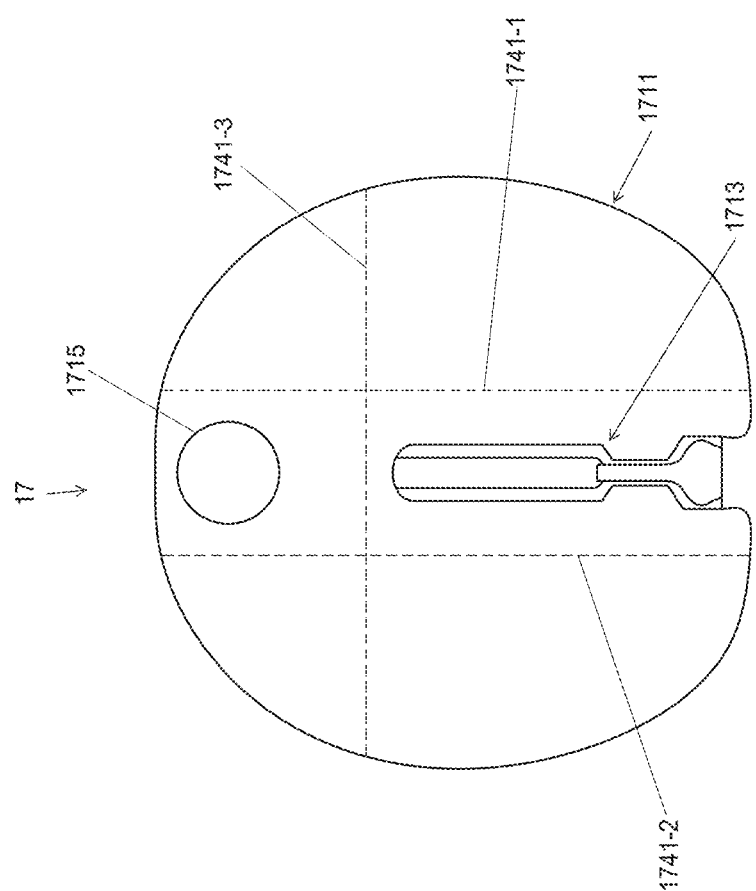
FIG. 20 shows an embodiment of a pressure-attenuating device in a deflated, flattened state.

Referring now to FIG. 20, the pressure-attenuating device 17 is shown in a deflated, flattened state with internal retention member 1715 on the lower layer of the balloon prior to being folded. A plurality of imaginary fold lines 1741-1, 1741-2, and 1741-3 are shown on balloon 1711 to depict where balloon 1711 may be folded. According to one embodiment, balloon 1711 may first be folded about line 1741-1, then about line 1741-2, and then about line 1741-3. Alternatively, balloon 1711 may be folded about line 1741-

2, then about line 1741-1, and then about line 1741-3. When device 17 is inflated, balloon 1711 may unfold in an order opposite to the order in which it had previously been folded. In an alternate embodiment, the balloon includes an integral retention member 1715, which is on top of the balloon when folded along line 1741-1 described above. The integral retention member may be circular, rectangular, oval or any shape so long as it is sufficiently wide to extend beyond the opening in the window, more preferably greater than 1.5 times the opening in the window, more preferably two times the opening in the window. This dimension permits the retention member to be tucked under the catheter on one or more sides of the window when the folded balloon is secured in the catheter.

It is to be understood that, although pressure-attenuating device 17 has been described herein as being inflatable, pressure-attenuating device 17 could be expandable in ways other than by inflation. For example, pressure-attenuating device 17 could be self-expandable, for instance, by virtue of being made of a shape-memory material.

Some of the advantageous features of using a delivery device 15 to deliver pressure-attenuating device 17 are that, due to the orientation and placement of window, there is a controlled deployment of pressure-attenuating device 17 away from the trigone of the patient and pressure-attenuating device 17 is kept away from the walls of the bladder while being inflated, such contact with the walls of the bladder possibly impeding the opening of valve to inflate device 17.

Figure 21:
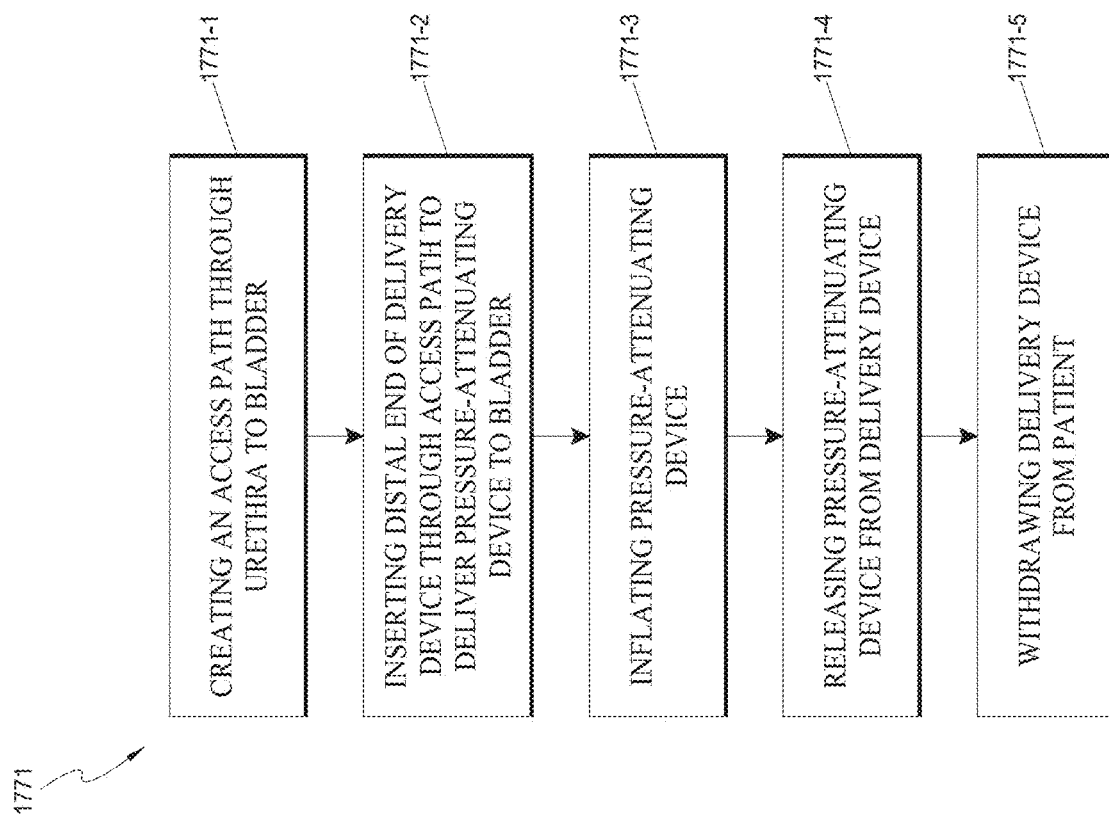
FIGS. 21-21D shows a flow chart and corresponding illustrations of how an embodiment of the balloon can be delivered according to certain embodiments.
Figure 21A:
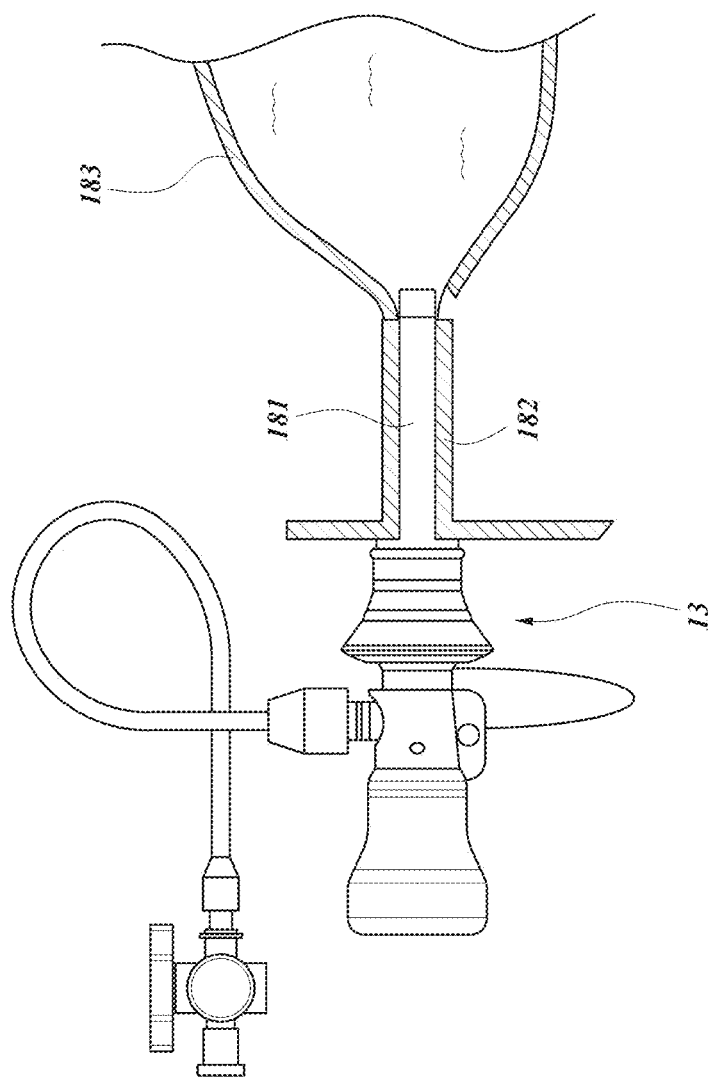
Figure 21B:
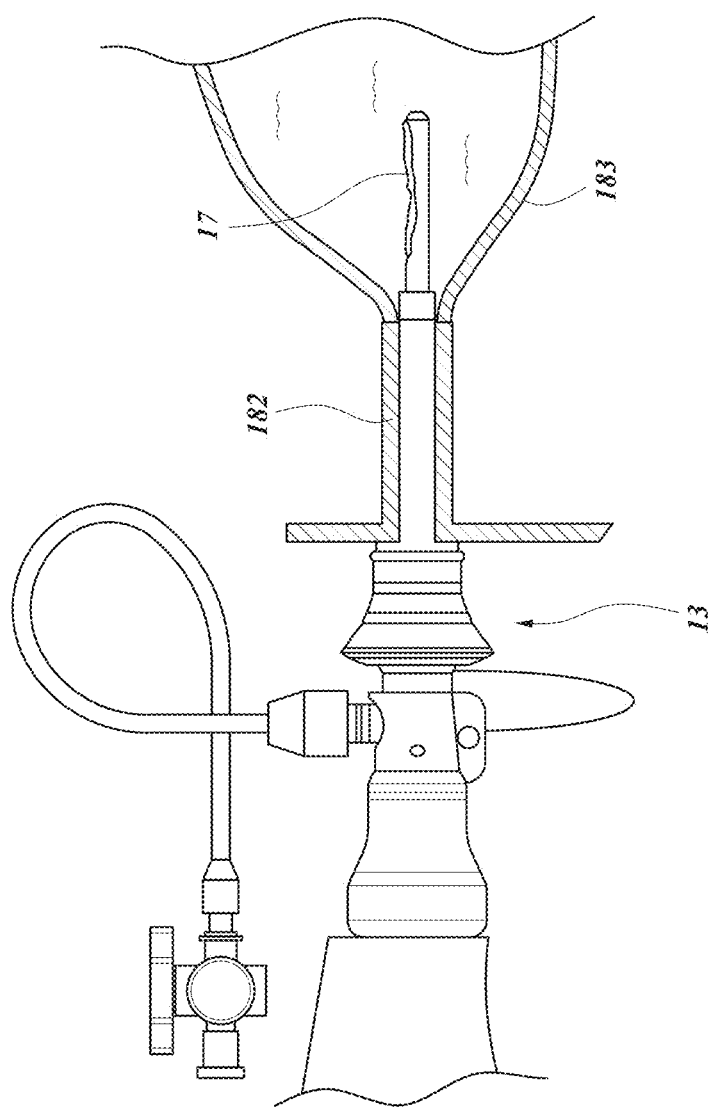

Referring now to FIG. 21, there is shown a flowchart, schematically depicting one possible method 1771 of implanting pressure-attenuating device in an anatomical structure of a patient, such as a bladder. Method 1771 may begin with a step 1771-1 of installing an access device 13 in a patient in any of the manners discussed above. Where, for example, an access device is used to provide transurethral access to the bladder, said installing step may comprise inserting a distal end of obturator, covered by sleeve 181, through the urethra 182 and into the bladder 183 and then removing obturator, whereby an access path extending across the urethra and into the bladder may be created (see FIG. 21A). Method 1771 may then continue with a step 1771-2 of inserting a distal end of a delivery device 15 through the access device 13 and into the anatomical structure of a patient. This may be done by inserting distal end of delivery device 15 through the remaining installed portion of access device 13 and into the bladder of the patient (see FIG. 21B). (Prior to insertion of delivery device 15 into an access device 13, pressure-attenuating device 17 may be loaded into delivery device 15.)

Figure 21C:
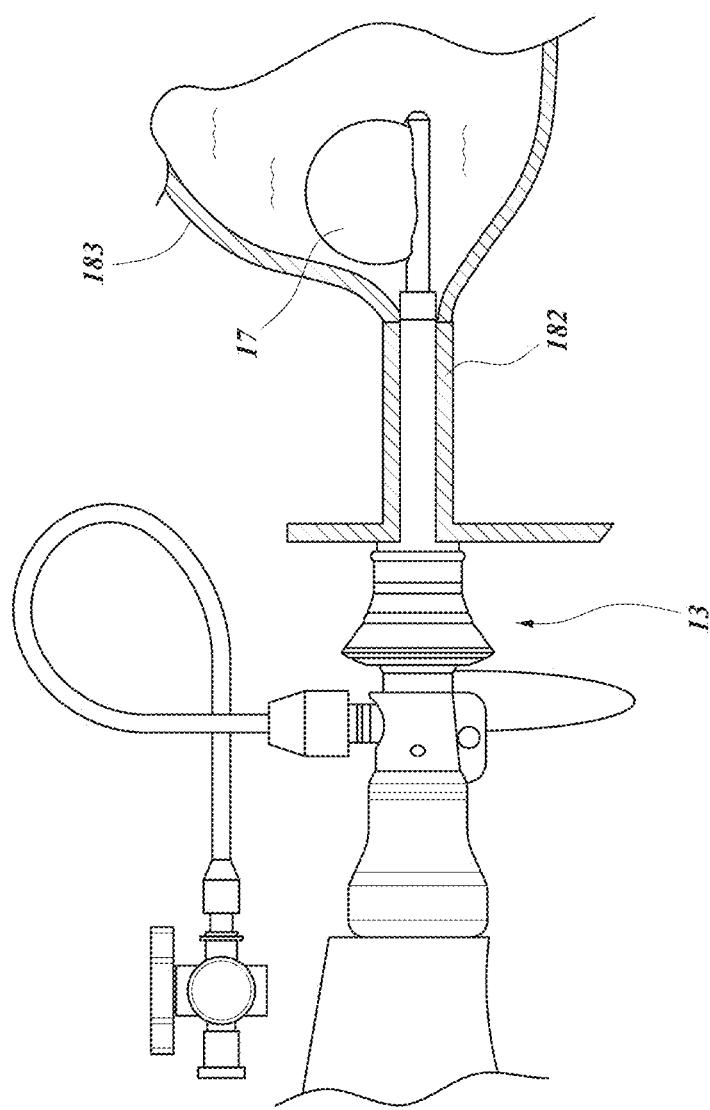
Figure 21D:
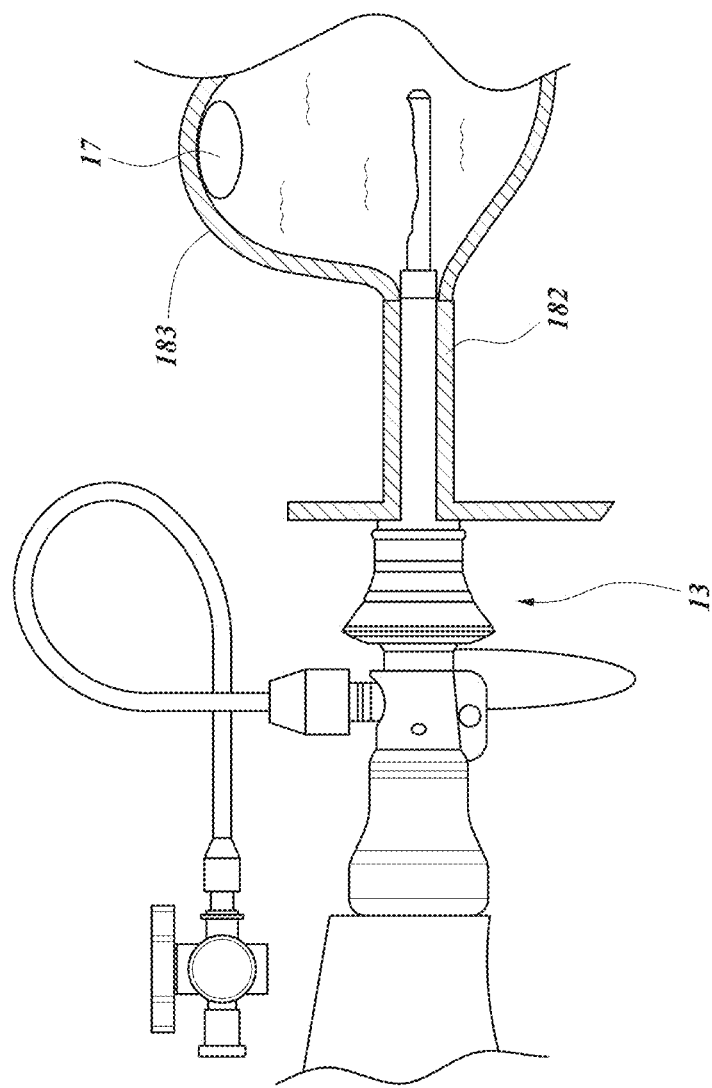

Method 1771 may then continue with a step 1771-3 of inflating pressure-attenuating device 17 (see FIG. 21C). Said inflating step may be effected by fully a depressing piston to dispense a first fluid medium from a first syringe into pressure-attenuating device 17 and then by fully a depressing piston to dispense a second fluid medium from a second syringe into pressure-attenuating device 17. Method 1771 may then continue with a step 1771-4 of releasing pressure-attenuating device 17 from delivery device 15 (see FIG. 21D), thereby allowing device 17 to float freely in the bladder or other anatomical structure. Said releasing step may be affected by a deactivating safety and then by a squeezing trigger, thereby causing a push-off member to slide distally until a push-off member pushes device 17 off of a distal end of an inflation tube. Method 1771 may then proceed with a step 1771-5 of withdrawing the delivery device from the access device 13. This may be done by withdrawing delivery device 15 from the remaining installed portion of an access device 13 while holding the remaining installed portion of access device 13 stationary in the patient. (Access device 13 may thereafter be removed from the patient or may remain in the patient to provide a conduit through which observational, removal, or other devices may be inserted.)

Removal

A removal device may be inserted through the passageway created by an access device. The removal device may be used to capture, to deflate and/or to remove the pressure-attenuating device. The removal device may also be used to view the inside of the anatomical structure, as well as the pressure-attenuating device. This viewing may be done during all or part of the capturing, deflating, and/or removing the pressure-attenuating device.

Certain additional embodiments of a removal device are described in U.S. Patent Application Publication No. 2010/0222802, incorporated by reference herein. See for example: FIGS. 19A-22B, 23H, and 24-29C and the accompanying discussion, including at paragraphs [0207]-[0274]. Additional embodiments of a removal device and/or the insertion device which can be in certain arrangements in combination with the embodiments of a pressure attenuation device herein can also be found in U.S. Provisional Application No. 62/725,210, filed Aug. 30, 2018, the entirety of which is also hereby incorporated by reference herein.

Embodiments of a removal device are also provided in U.S. Pat. No. 6,976,950, incorporated by reference herein. See for example: FIGS. 12, and 20-23, and the accompanying discussion, including at columns 18-21, and 25-26.

Figure 22:
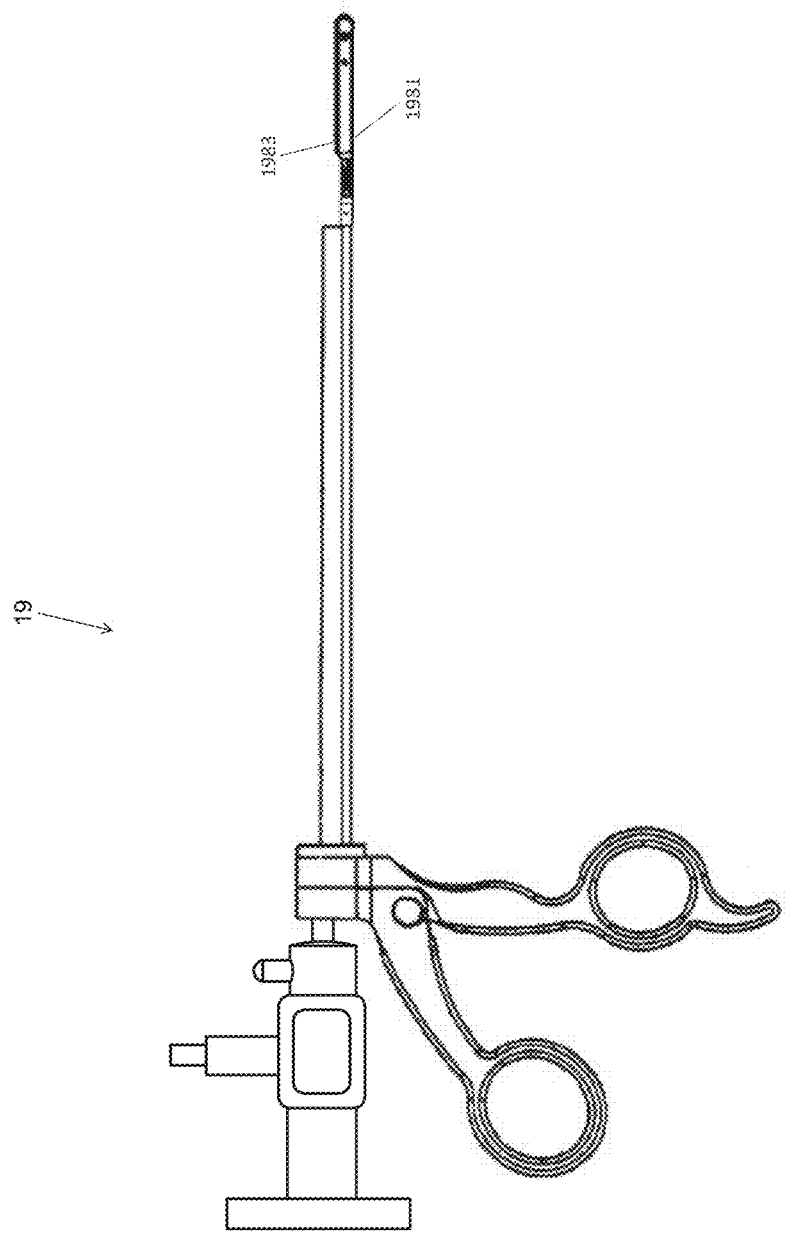
FIG. 22 shows an embodiment of a removal device.
Figure 23A:
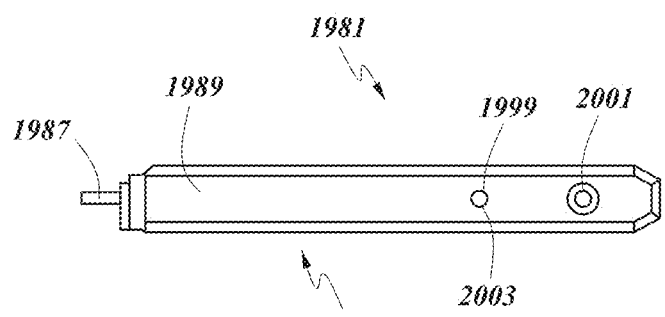
FIGS. 23A-23D, FIGS. 24A-24D, and FIGS. 25A-B show embodiments of the jaws of an removal device.
Figure 23B:
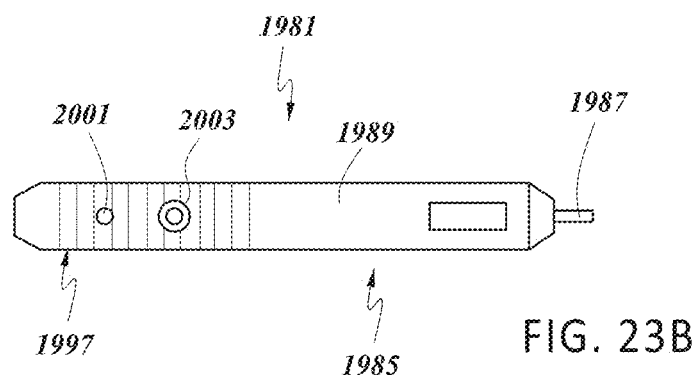
Figure 23C:
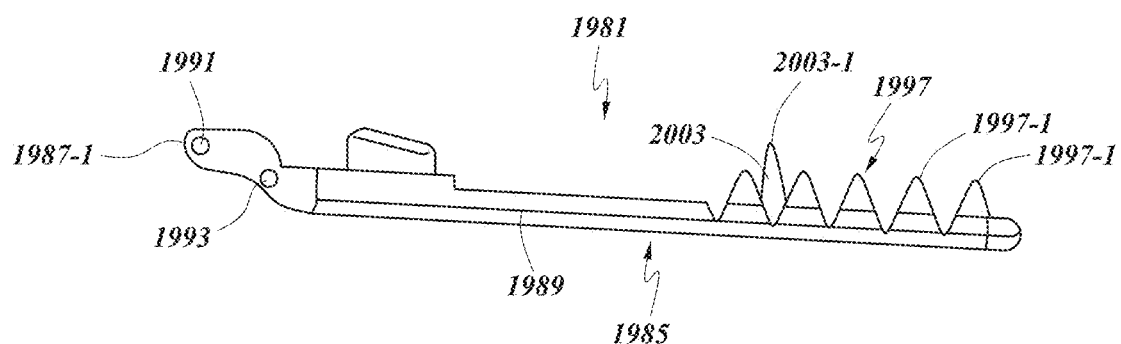
Figure 23D:
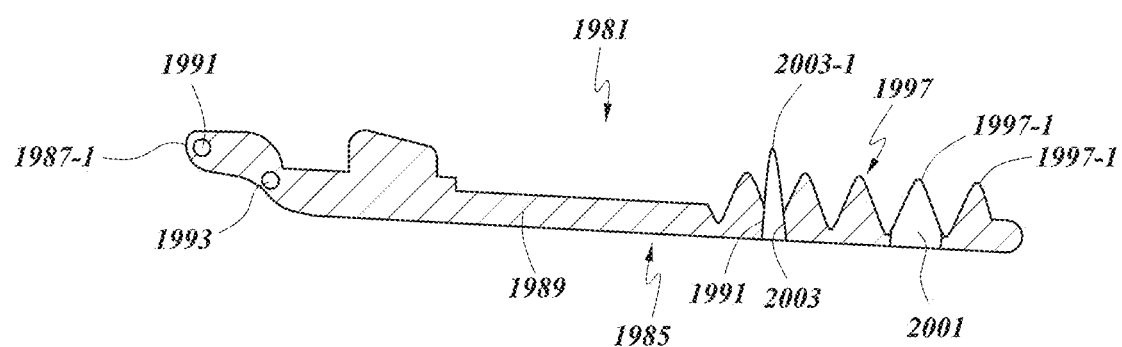
Figure 24A:
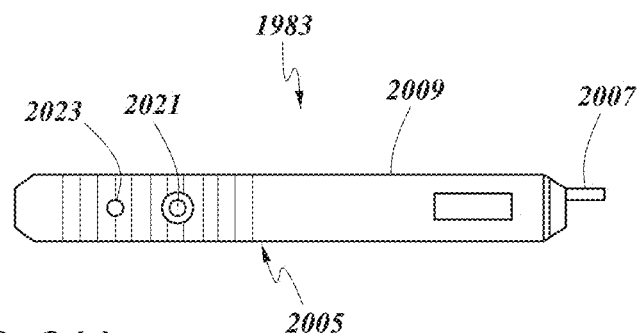
Figure 24B:
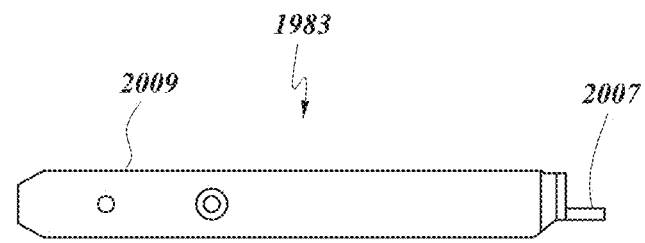
Figure 24C:
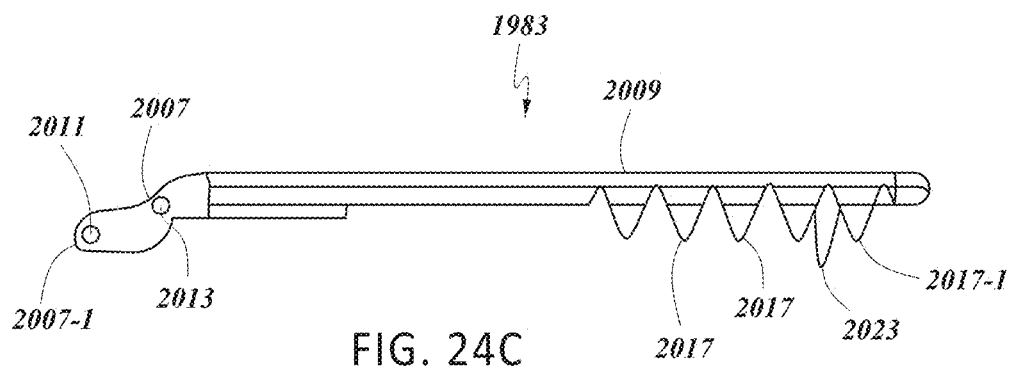
Figure 24D:
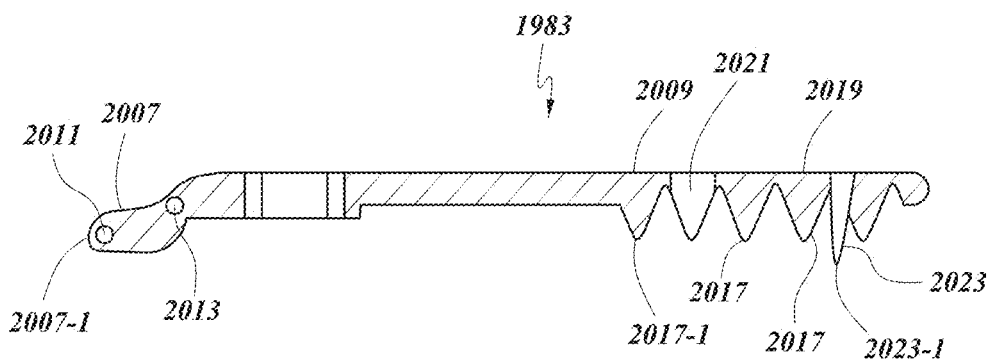
Figure 25A:
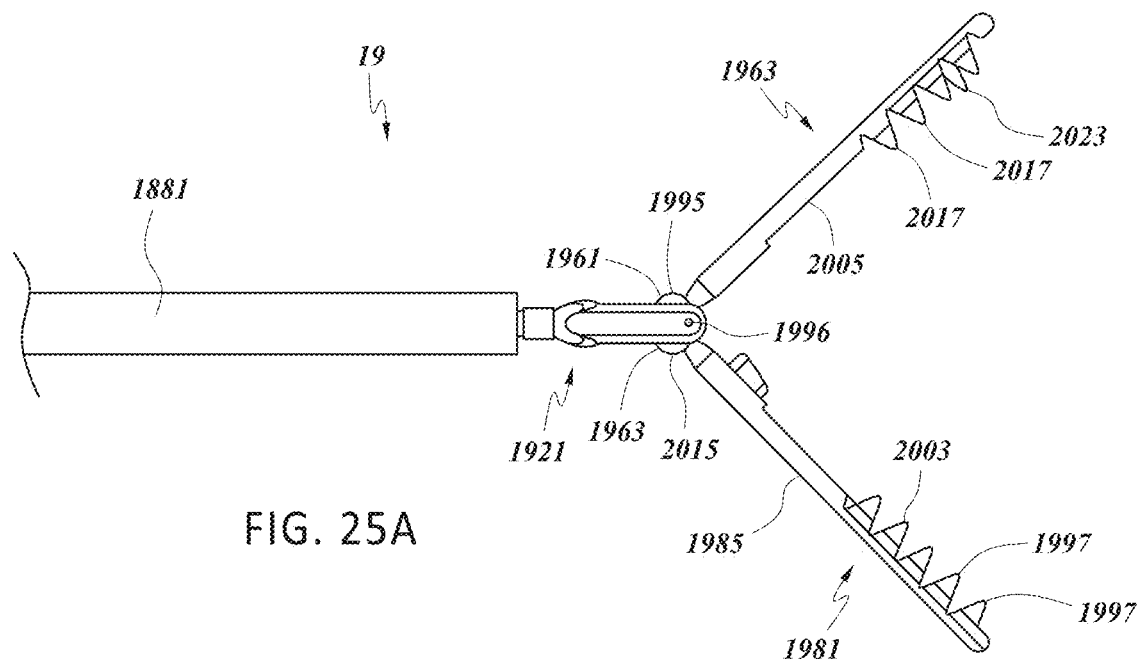
Figure 25B:
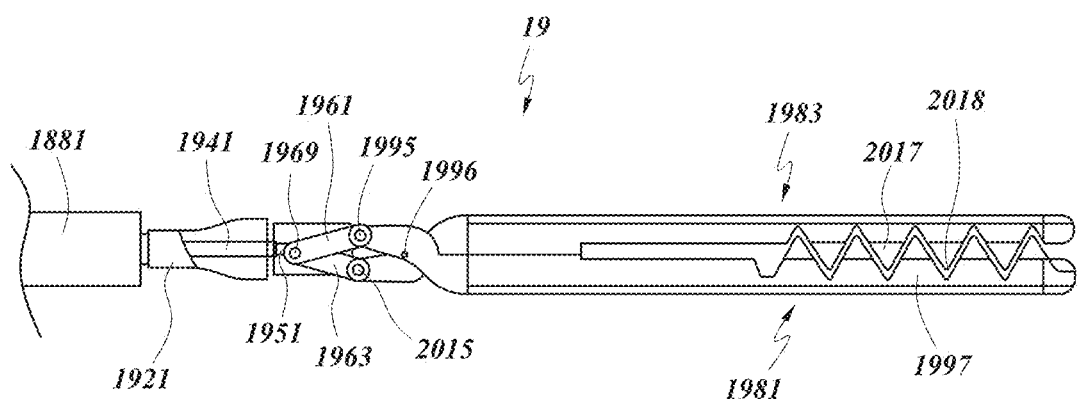

Referring now to FIG. 22, removal device 19 according to a certain embodiment is shown. The removal device 19 can include a pair of scissor-like handles that can be used to articulate a pair of jaws 1981, 1983 as will be described below. Removal device 19 may further comprise a pair of jaws 1981 and 1983 (FIGS. 23A-D, FIGS. 24A-D, FIGS. 25A-B). FIGS. 25A-B, show jaw 1983 and jaw 1981 assembled on removal device 19. The jaws can include corresponding teeth 1997, 2017 which can be used to grip or secure an implant. The jaws may also include one or more surface damaging or compromising structures. For example, the surface damaging structure 2003, 2023 can be a needle, knife, sharpened tooth, etc. In some embodiments, the surface damaging structure can be a canulated needle that can also serve to allow the media within in the implant to escape or otherwise be removed. In some embodiments, having the opening in the needle extend the entire length of the exposed needle structure permits the balloon to continue to deflate even when the needle has penetrated completely through the balloon. Additionally, the orientation of the sharp edge towards the distal end of the grasper has the advantage of preventing lacerating the balloon film during the tensile removal of the deflated or partially deflated balloon thru the sheath. Additionally, the proximity of the needle relative to adjacent teeth can improve the function of the removal system. Specifically, if the space between the tip of the needle and the tip of an adjacent tooth is between 0.05 and 10 times the difference in height between the tip of the needle and the tip of the adjacent tooth. This distance prevents the balloon from "tenting" over the needle and adjacent teeth without needle penetration of the balloon.

Jaw 1981, which is also shown separately in FIGS. 23A-D, may comprise an elongated member 1985 (which may be, for example, approximately 1.55-2.5 inches in length), preferably made of a medical-grade stainless steel or a similarly suitable material. Member 1985 may be shaped to include a proximal portion 1987 and a distal portion 1989. Proximal portion 1987, which may comprise a generally flat and arcuate arm, may be shaped to include a first transverse opening 1991 proximate to a proximal end 1987-1 of proximal portion 1987 and a second transverse opening 1993 spaced distally a short distance from first transverse opening 1991. A pivot pin 1995 may be received within opening 1991 of proximal portion 1987, as well as within opening 1967 of arm 1961, so as to pivotally couple jaw 1981 to arm 1961. A pivot pin 1996 may be received within opening 1993 of proximal portion 1987, as well as within opening 1933 of bracket 1921, so as to pivotally couple jaw 1981 to bracket 1921. Distal portion 1989 of member 1985 may be shaped to include a row of teeth 1997 facing towards jaw 1983, the row of teeth 1997 extending proximally from approximately the distal end of distal portion 1989. Each tooth 1997 may extend substantially across the width of distal portion 1989 and may have a height of, for example, approximately 1-10 mm, preferably approximately 5 mm. Each tooth 1997 may have a dulled peak 1997-1 that has a radius of, for example, 0.001-0.250 inch, preferably 0.005-0.050 inch, more preferably 0.010-0.25 inch. A first transverse opening 1999 may be provided in distal portion 1989 amongst teeth 1997, and a second transverse opening 2001 may be provided in distal portion 1989 amongst teeth 1997, first and second transverse openings 1999 and 2001 being spaced apart from one another by a short distance. A cannulated needle 2003 may be fixedly mounted in transverse opening 1999, needle 2003 having a sharpened end 2003-1 facing towards jaw 1983. Preferably, needle 2003 has a height that exceeds the height of teeth 1997 so that sharpened end 2003-1 extends beyond dulled peaks 1997-1. Needle 2003 may have an inner diameter of, for example, approximately 0.0005-0.500 inch, preferably approximately 0.005-0.250 inch, more preferably approximately 0.010-0.050 inch, and may have an outer diameter of, for example, approximately 0.001-0.750 inch, preferably approximately 0.010-0.300 inch, more preferably approximately 0.015-0.075 inch.

Jaw 1983, which is also shown separately in FIGS. 24A-D, may comprise an elongated member 2005 (which may be, for example, approximately 1.55-2.5 inches in length), preferably made of a medical-grade stainless steel or a similarly suitable material. Member 2005 may be shaped to include a proximal portion 2007 and a distal portion 2009. Proximal portion 2007, which may comprise a generally flat and arcuate arm, may be shaped to include a first transverse opening 2011 proximate to a proximal end 2007-1 of proximal portion 2007 and a second transverse opening 2013 spaced distally a short distance from first transverse opening 2011. A pivot pin 2015 may be received within opening 2011 of proximal portion 2007, as well as within opening 1973 of arm 1963, so as to pivotally couple jaw 1983 to arm 1963. Pivot pin 1996 may be received within opening 2013 of proximal portion 2007, as well as within opening 1933 of bracket 1921, so as to pivotally couple jaw 1983 to bracket 1921. In this manner, proximal movement of rod 1941, which may be caused by pivotal movement of ring portion 1807 of member 1801 towards ring portion 1823 of member 1803, may cause arms 1961 and 1963 to pivot towards each other which, in turn, may cause jaws 1981 and 1983 to pivot towards each other. On the other hand, distal movement of rod 1941, which may be caused by pivotal movement of ring portion 1807 of member 1801 away from ring portion 1823 of member 1803, may cause arms 1961 and 1963 to pivot away from one another which, in turn, may cause jaws 1981 and 1983 to pivot away from one another. Jaws 1981 and 1983 may open to an angle of, for example, approximately 20-150 degrees.

Distal portion 2009 of member 2005 may be shaped to include a row of teeth 2017 facing towards jaw 1981. The row of teeth 2017 may be staggered relative to teeth 1997 so that the peaks 1997-1 of teeth 1997 may be aligned with the spaces between teeth 2017 when jaws 1981 and 1983 are closed and so that the peaks 2017-1 of teeth 2017 may be aligned with the spaces between teeth 1997 when jaws 1981 and 1983 are closed. Each tooth 2017 may extend substantially across the width of distal portion 2009 and may be shaped and dimensioned similarly to each of teeth 1997. A first transverse opening 2019 may be provided in distal portion 2009 amongst teeth 2017, and a second transverse opening 2021 may be provided in distal portion 2009 amongst teeth 2017. Opening 2019 may be appropriately positioned and appropriately dimensioned to receive cannulated needle 2003 of jaw 1981 when jaws 1981 and 1983 are closed. (By receiving the sharpened end 2003-1 of needle 2003, opening 2019 facilitates and promotes full closure of jaws 1981 and 1983 around an inflated device 17, as opposed to having needle 2003 be deflected from the compressed and inflated device 17.) Opening 2019 may have an inner diameter of, for example, approximately 0.002-0.100 inch, preferably 0.010-0.300 inch, more preferably 0.015-0.100 inch. Opening 2021 may be aligned with opening 2001 of jaw 1981 when jaws 1981 and 1983 are closed, and a cannulated needle 2023 may be fixedly mounted in opening 2021 so as to be receivable within opening 2001 of jaw 1981 when jaws 1981 and 1983 are closed. Cannulated needle 2023 may have a sharpened end 2023-1 facing towards jaw 1981, and needle 2023 and opening 2001 may be dimensioned similarly to needle 2003 and opening 2019, respectively.

Preferably, teeth 1997 and 2017 are dimensioned appropriately so that, when jaws 1981 and 1983 are closed, a small gap 2018 (seen best in FIG. 109(*d*)) is left between the respective rows of teeth 1997 and 2017 that enables device 17 to be trapped between teeth 1997 and 2017 while minimizing any tearing of device 17 by teeth 1997 and 2017. In this manner, device 17 may be securely held or gripped between teeth 1997 and 2017 while cannulated needles 2003 and 2023 puncture device 17. Moreover, because needles 2003 and 2023 are cannulated, the fluid contents of device 17 may be quickly evacuated from device 17 through needles 2003 and 2023 without having needles 2003 and 2023 plug the same puncture holes they create.

It is to be understood that, although cannulated needles 2003 and 2023 are described herein as being used to puncture device 17, other puncturing devices, such as, but not limited to, blades, scissors, pins, hooks, or the like, may alternatively or additionally be used.

In addition, it is to be understood that, although cannulated needles 2003 and 2023 are described herein as being oriented generally perpendicular to members 1985 and 2005, respectively, cannulated needles 2003 and 2023 need not be so oriented and may be oriented, for example, so that sharpened ends 2003-1 and 2023-1 are angled towards proximal portions 1987 and 2007, respectively.

Additionally, it is to be understood that, although both jaw 1981 and jaw 1983 are described herein as being movable, one could make one of jaws 1981 and 1983 stationary and the other of jaws 1981 and 1983 movable.

Figure 26:
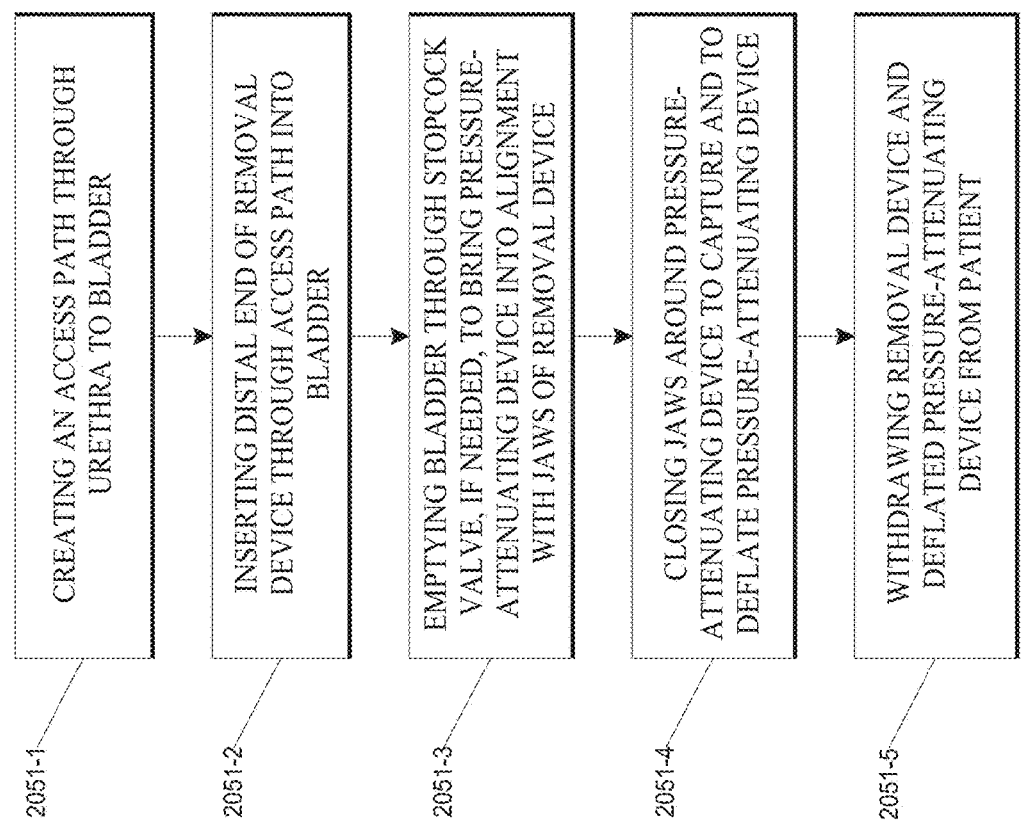
FIGS. 26-26D shows a flow chart and corresponding illustrations of how an embodiment of the balloon can be removed according to certain embodiments.
Figure 26A:
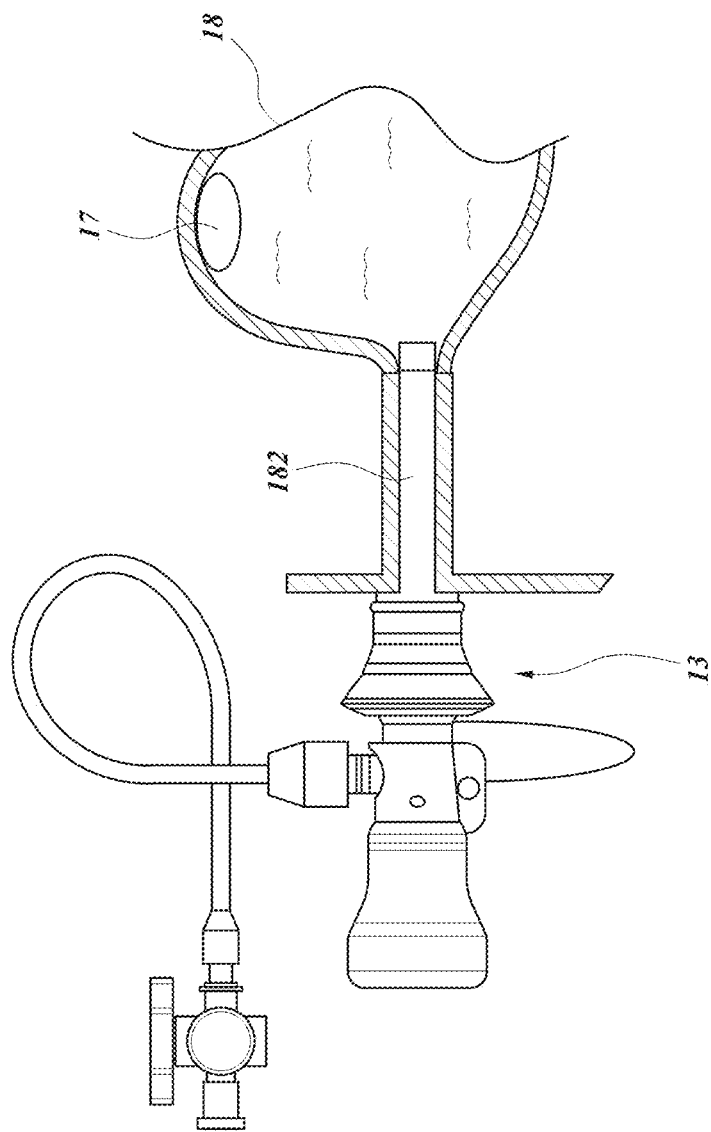
Figure 26C:
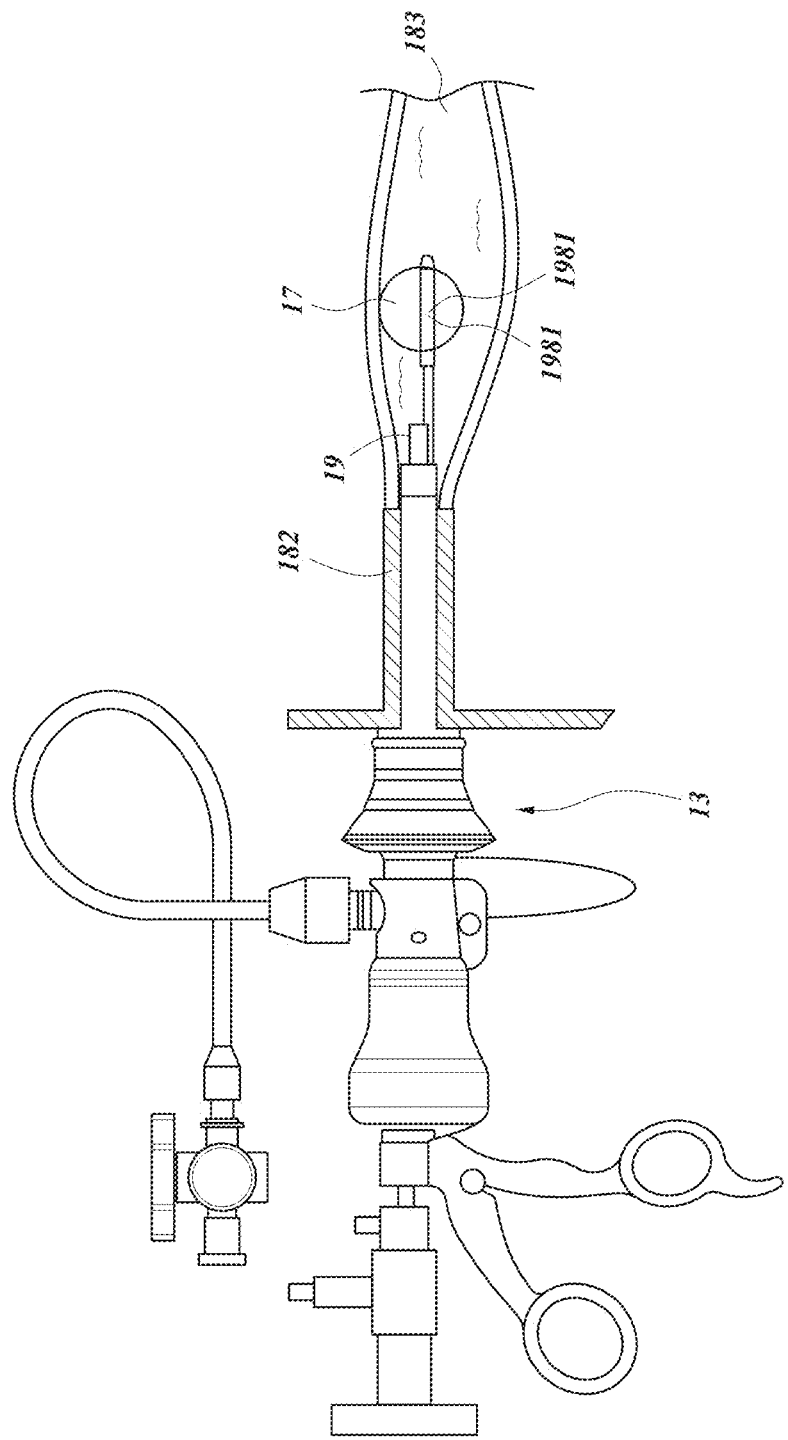
Figure 26D:
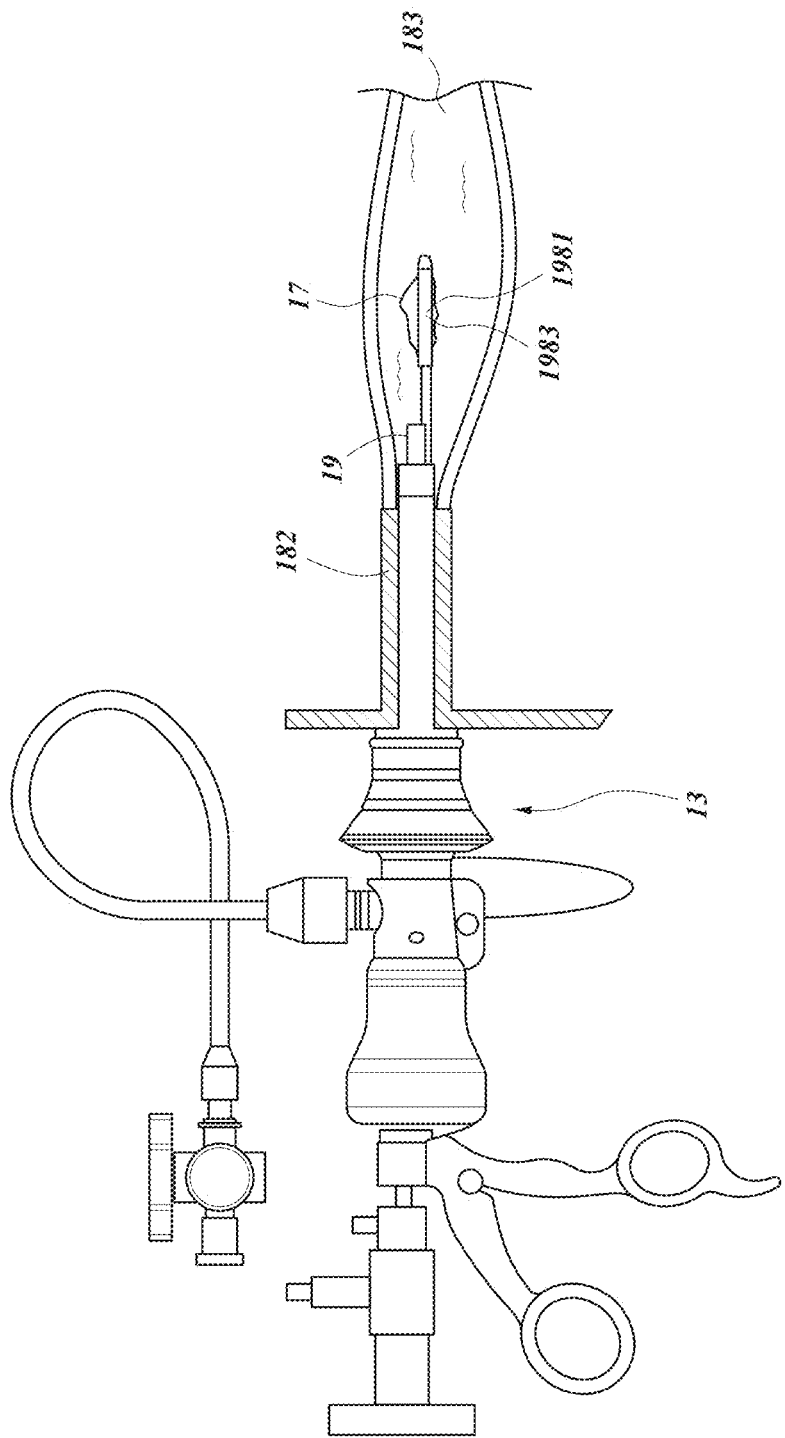

Referring now to FIG. 26, there is shown a flowchart, schematically depicting one possible method 2051 of using removal device 19 to remove an implanted pressure-attenuating device 17 from an anatomical structure of a patient, such as a bladder. Method 2051 may begin with a step 2051-1 of installing an access device 13 in a patient in any of the manners discussed above. Where, for example, an access device 13 can be used to provide transurethral access to the bladder, said installing step may comprise inserting a distal end of an obturator, which may be covered by sleeve, into the urethra 182, advancing the obturator and sheath through the urethra 182 and into the bladder 183, and then removing the obturator, whereby an access path extending across the urethra 182 and into the bladder 183 may be created (see FIG. 26A). Method 2051 may then continue with a step 2051-2 of inserting the distal end of a removal device 19 through the access device 13 and into the anatomical structure of the patient. This can be done by inserting the distal end of removal device 19 through the remaining installed portion of the access device 13 and into the bladder of the patient (see FIG. 26B). Where the method 2051 is performed in the bladder, or other fluid filled structure, the method may then continue with a step 2051-3 of emptying the structure of liquid, such as through stopcock valve 287, until the inflated pressure-attenuation device 17 comes into alignment with removal device 19. For example, urine can be removed from the bladder until the pressure-attenuation device 17 is aligned with opened jaws 1981 and 1983 as observed through a scope (see FIG. 26C). Method 2051 may then continue with a step 2051-4 of engaging the inflated pressure-attenuation device 17 with the removal device 19. This may also include deflating the inflated pressure-attenuation device 17. For example, the jaws 1981 and 1983 can close around pressure-attenuation device 17, causing pressure-attenuating device 17 to deflate over the next several seconds (see FIG. 26D). Method 2051 may then conclude with a step 2051-5 of withdrawing removal device 19, together with the deflated pressure-attenuating device 17 from the anatomical structure through the access device 13. The implanted pressure-attenuating 17 may be held between jaws 1981 and 1983 and may be removed through the remaining installed portion of access device 13 while the remaining installed portion of access device 13 is held stationary in the patient. If, for some reason, pressure-attenuating 17 has not deflated completely as it is being withdrawn from the patient, the distal end 64 of sheath 61 may advantageously serve as a fulcrum to help to compress pressure-attenuant 17 sufficiently for its facile withdrawal from the patient. (Access device 13 may thereafter be removed from the patient or may remain in the patient to provide a conduit through which observational, removal, or other devices may be inserted.)

Coatings

Despite the hydrophobic tendencies and relative insolubility of PFCs in water and bodily fluids, PFCs will diffuse out of certain enclosures. This can be minimized by various surface treatments including lubricity coatings, anti-microbial coatings, acid or basic pH coatings, drug eluting or containing coatings, roughening, or establishing a positively or negatively charged surface. Both the interior and/or the exterior of the balloons disclosed herein can be treated and each could be treated in a like or different matter. For example they can be charged+on the outside and—on the inside or rough on the outside to form and capture bubbles and smooth on the outside to be non-irritating. The inside and outside of the enclosure can be hydrophilic or hydrophobic, alternatively the inside and outside can be treated to have opposite attractiveness to water.

Examples of suitable coatings for various devices disclosed herein include: aqueous hydrogels on inside to prevent bubble formation, butyl rubbers to hold in PFCs, metal coatings, nano-crystallized silver based antimicrobial coating, polyvinylpryrrolidone based coatings, drug coatings including duloxetine hydrochloride, neurotransmitters mediating drugs, analgesics, antiseptics, antibiotics, incontinence treatment drugs, anti-cancer drugs, cystitis treating drug, and oxybutynin.

Initial and Automatic Inflation

Certain embodiments involve the inflation of implants described herein with initial infusions of various media, including gases or liquids, such as air, nitrogen, oxygen, carbon dioxide, PFC, etc. The initial infusion can be before or after the device is implanted. The initial infusing can be delivered via a syringe, tube, capsule, ampule, cannula, or other delivery device.

In another embodiment, a self-inflating implant comprising a selected PFC element and an enclosure at least partially permeable to nitrogen and oxygen is provided. After implantation, the PFC vapor will dilute any air component gases within the enclosure and cause the air component gases in the anatomical structure to diffuse into the enclosure until equilibrium is reached thereby inflating the enclosure device.

In some embodiments, a pressurized implant is adapted to inflate over time to a selected volume or pressure and then deflate in response to an elevated pressure. For example, an implant is inserted within a bladder and inflates to a first selected pressure or volume. Upon the application of an external load or pressure, such as when the patient voids the bladder, the implant reaches a second selected pressure, at which point the implant is adapted to rapidly decrease in volume as the high vapor pressure element within the implant condenses into liquid. When the external load is removed, such as, after the bladder is empty, the implant will gradually return to its first selected volume or pressure. Thus, by providing an implant operable to attenuate bladder pressure spikes within a certain range and then quickly deflate at the time of voiding, a diminished and more comfortable volume is present at the time of emptying of the bladder. Therefore, a more comfortable treatment is effected.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems and methods for inflatable implants, and pressure attenuating inflatable implants, have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems and methods for inflatable implants, and pressure attenuating inflatable implants. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

In summary, various embodiments and examples of systems and methods for inflatable implants, and pressure attenuating inflatable implants, have been disclosed. Although the systems and methods for inflatable implants, and pressure attenuating inflatable implants, have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described herein, but should be determined only by a fair reading of the claims that follow.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." In addition, it is anticipated that with numbers in the description preceded by the term such as "about" or "approximately" these numbers can be claimed with or without the term "about" or "approximately" preceding these numbers. Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. A pressure attenuation device for use in a bladder, the pressure attenuation device comprising:
   a balloon comprising an outer wall and defining an interior chamber therein, the balloon having a minimum wall thickness of between 0.001 inches and 0.00175 inches, the balloon being configured to elastically deform up to at least an internal pressure of 90 cm $H_2O$; and wherein the balloon elastically deforms and increases in volume by less than 190% when the internal pressure within the balloon is increased from 2.5 cm $H_2O$ to 90 cm $H_2O$ and the balloon further comprising a media having a vapor pressure of at least 155 cm $H_2O$ at 37 degrees Celsius.

2. The pressure attenuation device of claim 1, wherein the media has a vapor pressure of between 155 cm $H_2O$-185 cm $H_2O$ at 37 degrees Celsius.

3. The pressure attenuation device of claim 1, wherein the media has a vapor pressure of between 155 cm $H_2O$-165 cm $H_2O$ at 37 degrees Celsius.

4. The pressure attenuation device of claim 3, wherein the media is positioned within the interior chamber.

5. The pressure attenuation device of claim 4, wherein the media comprises a perfluorocarbon (PFC).

6. The pressure attenuation device of claim 1, wherein the balloon elastically deforms and increases in volume by at least 75% but less than 90% when the internal pressure within the balloon is increased from 2.5 cm $H_2O$ to 90 cm $H_2O$.

7. The pressure attenuation device of claim 1, wherein the balloon elastically deforms to at least an internal pressure of 120 cm $H_2O$.

8. The pressure attenuation device of claim 1, wherein the balloon has an unstretched volume of between 1 and 180 cc.

9. The pressure attenuation device of claim 1, wherein the balloon elastically deforms between internal pressures of 2.5 cm $H_2O$ to 90 cm $H_2O$ for at least 15 cycles.

10. The pressure attenuation device of claim 1, wherein the balloon elastically deforms between internal pressures of 2.5 cm $H_2O$ to 90 cm $H_2O$ for at least 25 cycles.

11. The pressure attenuation device of claim 1, wherein the balloon elastically deforms between internal pressures of 2.5 cm $H_2O$ to 90 cm $H_2O$ for at least 50 cycles.

12. The pressure attenuation device of claim 1, wherein the balloon elastically deforms between internal pressures of 2.5 cm $H_2O$ to 90 cm $H_2O$ for at least 100 cycles.

13. The pressure attenuation device of claim 1, wherein the balloon has an unstretched volume of between 20 and 35 milliliters (ml).

14. The pressure attenuation device of claim 1, wherein the balloon has volume at an internal pressure of 90 cm $H_2O$ that is less than or equal to 70 milliliters (ml).

15. A pressure attenuation device for use in a bladder, the pressure attenuation device comprising:
   a balloon comprising an outer wall and defining an interior chamber therein, the balloon being configured to elastically deform up to at least an internal pressure of 90 cm $H_2O$;
   a high vapor pressure media having a vapor pressure of between 155 cm-185 cm $H_2O$ at 37 degrees Celsius; and wherein the balloon elastically deforms and increases in volume by greater than 50% when the internal pressure within the balloon is increased from 2.5 cm $H_2O$ to 90 cm $H_2O$ and less than 190% when the internal pressure within the balloon is increased from 2.5 cm $H_2O$ to 90 cm $H_2O$.

16. The pressure attenuation device of claim 15, wherein the high vapor pressure media has a vapor pressure of between 155 cm $H_2O$-165 cm $H_2O$ at 37 degrees Celsius.

17. The pressure attenuation device of claim 15, wherein the high vapor pressure media is positioned within the interior chamber.

18. The pressure attenuation device of claim 15, wherein the high vapor pressure media comprises a perfluorocarbon (PFC).

19. The pressure attenuation device of claim 15, wherein the balloon elastically deforms between internal pressures of 2.5 cm $H_2O$ to 90 cm $H_2O$ for at least 15 cycles.

20. The pressure attenuation device of claim 15, wherein the balloon has an unstretched volume of between 1 and 180 cc.

21. The pressure attenuation device of claim 15, wherein the balloon has an unstretched volume of between 20 and 35 milliliters (ml).

22. The pressure attenuation device of claim 15, wherein the balloon has volume at an internal pressure of 90 cm $H_2O$ that is less than or equal to 70 milliliters (ml).

\* \* \* \* \*